United States Patent
Barbosa, Jr. et al.

(10) Patent No.: US 7,115,644 B2
(45) Date of Patent: Oct. 3, 2006

(54) HETEROCYCLIC COMPOUNDS

(75) Inventors: Antonio Jose del Moral Barbosa, Jr., Middlebury, CT (US); Daniel R. Goldberg, Redding, CT (US); Abdelhakim Hammach, Danbury, CT (US); Pingrong Liu, Southbury, CT (US); Neil Moss, Ridgefield, CT (US); Mark Stephen Ralph, Beacon Falls, CT (US); Gregory Paul Roth, Woodstock, CT (US); Christopher Ronald Sarko, New Milford, CT (US); Fariba Soleymanzadeh, Brewster, NY (US); Andre White, Newtown, CT (US)

(73) Assignee: Boehringer Ingelheim Pharmaceuticals Inc., Ridgefield, CT (US)

(*) Notice: Subject to any disclaimer, the term of this patent is extended or adjusted under 35 U.S.C. 154(b) by 134 days.

(21) Appl. No.: 10/654,452

(22) Filed: Sep. 3, 2003

(65) Prior Publication Data

US 2004/0192748 A1 Sep. 30, 2004

Related U.S. Application Data

(60) Provisional application No. 60/410,420, filed on Sep. 13, 2002.

(51) Int. Cl.
*A61K 31/4184* (2006.01)
*C07D 235/26* (2006.01)

(52) U.S. Cl. ............ 514/387; 514/254.06; 514/234.5; 514/338; 514/278; 514/322; 514/316; 514/211.03; 514/365; 544/370; 544/139; 540/524; 546/273.7; 546/199; 546/187; 546/17; 548/306.4; 548/304.7; 548/181; 548/306.1

(58) Field of Classification Search ............ 548/306.4, 548/304.7, 181, 306.1; 514/387, 254.06, 514/234.5, 338, 278, 322, 316, 211.03, 365; 544/370, 139; 546/273.7, 199, 187, 17; 540/524
See application file for complete search history.

(56) References Cited

U.S. PATENT DOCUMENTS

| | | | |
|---|---|---|---|
| 5,162,318 A * | 11/1992 | Hara et al. ............ | 514/234.5 |
| 5,200,422 A | 4/1993 | Olesen et al. | |
| 5,281,714 A | 1/1994 | Fobare et al. | |
| 5,371,094 A | 12/1994 | Heine et al. | |
| 5,534,534 A | 7/1996 | Makino et al. | |
| 6,498,275 B1 | 12/2002 | Butlin et al. | |

2003/0139605 A1 7/2003 Riedl et al.

FOREIGN PATENT DOCUMENTS

| | | |
|---|---|---|
| EP | 0 616 807 | 8/1998 |
| EP | 1036821 | 9/2000 |
| WO | WO 94/05281 | 3/1994 |
| WO | WO 99/62506 A1 | 12/1999 |
| WO | WO 00/41698 A1 | 7/2000 |
| WO | WO 0050419 | 8/2000 |
| WO | WO 01/05770 A1 | 1/2001 |

OTHER PUBLICATIONS

Morel et al., Magnetic Resonance in Chemistry (1997), 35(8), pp. 556-560.*
Viswanathan et al., Indian Journal of Chemistry, Section B: Organic Chemistry Including Medicinal Chemistry (1985), 24B(9), pp. 948-951.*
Efros et al., Zhurnal Obshchei Khimii (1957), 27, pp. 127-135.*
Chemical Abstracts, Database Accession No. 1997;539019; XP002265898; RN 195379-37-4 & Magnetic Resonance In Chemistry: vol. 35, No. 8, 1997, pp. 556-560.

* cited by examiner

*Primary Examiner*—Laura L. Stockton
(74) *Attorney, Agent, or Firm*—Michael P. Morris; Anthony P. Bottino; Philip I. Datlow

(57) ABSTRACT

Disclosed are benzimidazolone compounds of formulas (I) & (II):
wherein $R_1$, $R_2$, $R_3$, $R_4$, $R_5$, X, L, m, n and t are defined herein. The compounds inhibit production of cytokines involved in inflammatory processes and are thus useful for treating diseases and pathological conditions involving inflammation such as chronic inflammatory disease. Also disclosed are processes for preparing these compounds and pharmaceutical compositions comprising these compounds

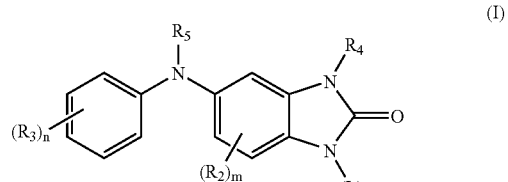

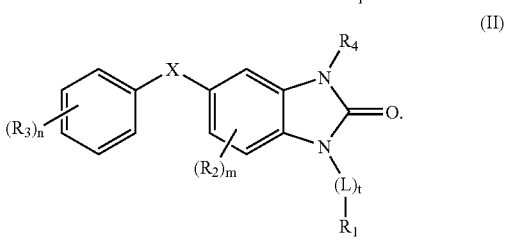

16 Claims, No Drawings

HETEROCYCLIC COMPOUNDS

APPLICATION DATA

This application claims benefit to U.S. provisional application No. 60/410,420 filed Sep. 13, 2002.

TECHNICAL FIELD OF THE INVENTION

This invention relates to benzimidazolone compounds of formulas (I) and (II):

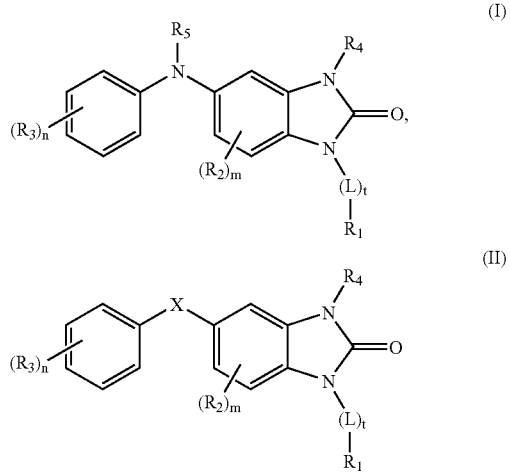

wherein $R_1$, $R_2$, $R_3$, $R_4$, $R_5$, X, L, m, n and t are defined below. The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Compounds useful as p38 MAP kinase inhibitors are known and have been shown to be useful for inhibiting cytokine production. Pargellis C, et al. 2002 Nat Struct Biol. 9:268–272.

Tumor necrosis factor (TNF) and interleukin-1 (IL-1) are important biological entities collectively referred to as proinflammatory cytokines which play a role in cytokine mediated diseases. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, Rev. Infect. Disease 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, J. Invest. Med. 43: 28–38). Studies suggest that inflammatory changes mediated by cytokines may be involved in endothelial cell pathogenesis including restenosis after percutaneous transluminal coronary angioplasty (PTCA) (Tashiro, H., et al., 2001 March, Coron Artery Dis 12(2):107–13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, British J. Rheum. 35: 334–342 and Stack, W. A., et al., 1997, Lancet 349: 521–524). The monoclonal antibody is thought to function by binding to both soluble TNFα and to membrane bound TNF.

A soluble TNFα, receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, Nature Biotechnology 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, Inflamm. Res. 46: S143).

IL-1 has been implicated as an immunological effect or molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, Nutrution 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, Biomed Pharmacother. 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, J Bone Miner Res. 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, Proc Soc Exp Biol Med. 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther*. 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol*. 109, 54). IL-1 and TNF are both involved in periodontal disease. The destructive process associated with periodontal disease may be due to a disregulation of both IL-1 and TNF (Howells, 1995, *Oral Dis*. 1, 266).

Proinflammatory cytokines such as TNFα and IL-1α are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J*. 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol*. 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J.*, 15, 281). Circulating TNFα may also contribute to weight loss associated with this disease (N. Takabatake et al., 2000, *Amer. J. Resp. & Crit. Care Med.*, 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3-12), kidney (Lemay et al., 2000, *Transplantation*, 69, 959), and the nervous system (Mitsui et al., 1999, *Brain Res.*, 844, 192).

TNFα is also a potent osteoclastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867). IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res*. 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat*. 7, 177). Data obtained from IL-1 knock out mice indicates the critical involvement in fever for this cytokine (Kluger et al., 1998, *Clin Exp Pharmacol Physiol*. 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr*. 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol*. 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's cisease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther*. 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050). GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol*. 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and post-menopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilboum, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the THI phenotype (Sartor 1996, *Aliment Pharmacol Ther.* 10 Suppl 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivoponto-cerebellar atrophy, neuropathic pain syndromes, diabetic neuropathy, HIV-related neuropathy, MERRF and MELAS syndromes, Leber's disease, Wemicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNFα anatagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res 2000 May 15 90(2)95–101; Shock 1998 Sep. 10(3): 160–75. p38MAP kinase pathway plays an role in B.burgdorferi-elicited infammation and may be useful in treating inflammation induced by the Lyme disease agent. Anguita, J. et. al., *The Journal of Immunology*, 2002,168:6352–6357.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis. Di-substituted aryl and heteroaryl compounds are also disclosed in U.S. Pat. Nos. 6,080,763; 6,319,921; 6,297,381 and 6,358,945. The compounds in the patents are alleged to possess anti-cytokine activity and are therefore useful in treating diseases associated with inflammation.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production by inhibiting p38 MAP kinase with small molecule compounds will be beneficial in the treatment of various disease states.

It is therefore an object of the invention to provide benzimidazolone compounds of formulas (I) & (II):

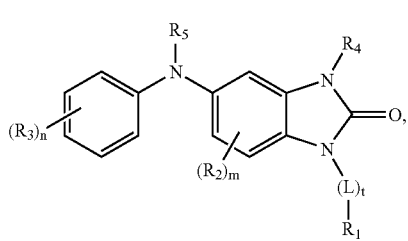

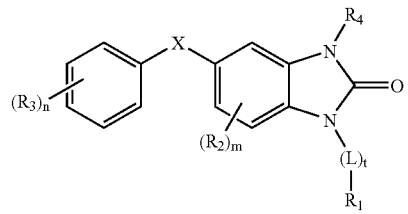

wherein $R_1$, $R_2$, $R_3$, $R_4$, $R_5$, X, L, m, n and t are defined below.

It is a further object of the invention to provide methods for treating cytokine mediated diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

In one broad generic aspect of the invention, there are provided compounds of the formula (I):

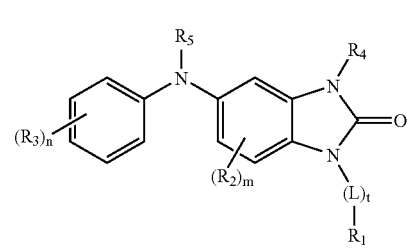

m and n are independently 0, 1 or 2;
t is 0–10;
L is —CH$_2$— optionally substituted by alkyl or alkoxy;
$R_1$ is chosen from amino, alkyl, $C_{3-7}$ cycloalkyl, aryl, heteroaryl and heterocyclyl each optionally substituted by one to four $R_a$;
$R_2$ is chosen from mono-or-di-alkylamino, alkylthio, alkoxy, $C_{3-7}$ cycloalkyl, aryl, heteroaryl and heterocyclyl each optionally substituted by one to four $R_b$;
each $R_a$ and $R_b$ are independently chosen from alkyl, alkenyl, alkynyl, cycloalkyl, aryl, heteroaryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, oxo, halogen, trifluoromethyl, nitro, nitrile and amino or guanidino each optionally mono-or-di-substituted by alkyl, acyl or alkoxycarbonyl, wherein any of the above $R_a$ or $R_b$ are optionally halogenated where possible;
each $R_3$ is chosen from alkyl, alkenyl, alkynyl, cycloalkyl, aryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-or-di-substituted by alkyl, acyl or alkoxycarbonyl, wherein any of the above $R_3$ are optionally halogenated where possible; and $R_4$ and $R_5$ are independently chosen from hydrogen and $C_{1-3}$ alkyl;

or the pharmaceutically acceptable acids and salts or isomers thereof.

In a second embodiment there are provided compounds of the formula (I) and wherein:

t is 0–5;

L is —$CH_2$— optionally substituted by methyl, ethyl or propyl;

$R_1$ is chosen from amino, $C_{1-6}$ alkyl, $C_{3-7}$ cycloalkyl, indanyl, indenyl, phenyl naphthyl, heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl and heterocyclyl chosen from aziridinyl, pyrrolidinyl, pyrrolinyl, morpholinyl, thiomorpholinyl, tetrahydrofuranyl, dioxalanyl, pyranyl, piperidinyl and piperazinyl, each optionally substituted by one to three $R_a$;

$R_2$ is chosen from mono- or di-$C_{1-5}$ alkyl amino, $C_{1-5}$ alkylthio, $C_{1-5}$ alkoxy, $C_{3-7}$ cycloalkyl, aryl, heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl and heterocyclyl chosen from aziridinyl, pyrrolidinyl, pyrrolinyl, morpholinyl, thiomorpholinyl, tetrahydrofuranyl, dioxalanyl, pyranyl, piperidinyl and piperazinyl, each optionally substituted by one to three $R_b$;

each $R_a$ and $R_b$ are independently chosen from $C_{1-5}$ alkyl, $C_{2-5}$ alkenyl, $C_{2-5}$ alkynyl, $C_{3-7}$ cycloalkyl, aryl, arylalkyl, aryloxy, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_a$ or $R_b$ are optionally halogenated where possible;

each $R_3$ is chosen from hydrogen, $C_{1-5}$ alkyl, $C_{2-5}$ alkenyl, $C_{2-5}$ alkynyl, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_3$ are optionally halogenated where possible; and $R_4$ and $R_5$ are independently chosen from hydrogen and methyl.

In a third embodiment there are provided compounds of the formula (I) as described immediately above and wherein:

m is 0 or 1;

n is 0, 1 or 2;

t is 0–3;

L is —$CH_2$— optionally substituted by methyl;

$R_1$ is chosen from $C_{3-6}$ alkyl, amino, $C_{3-7}$ cycloalkyl, indanyl, indenyl, phenyl, naphthyl, heteroaryl chosen from isoxazolyl, oxazolyl, thiadiazolyl, tetrazolyl, pyrazolyl, pyrrolyl, imidazolyl, pyridinyl, pyrimidinyl, pyrazinyl, pyridazinyl, quinoxalinyl, indolyl, benzimidazolyl, benzoxazolyl, benzothiazolyl, quinolinyl, quinazolinyl and indazolyl and heterocyclyl chosen from pyrrolidinyl, pyrrolinyl, morpholinyl, thiomorpholinyl, tetrahydrofuranyl, dioxalanyl, tetrahydropyranyl, piperidinyl and piperazinyl, each optionally substituted by one to two $R_a$;

$R_2$ is chosen from heteroaryl chosen from pyridinyl, pyrimidinyl, pyrazinyl and pyridazinyl and heterocyclyl chosen from morpholinyl, thiomorpholinyl, pyranyl, piperidinyl and piperazinyl, each optionally substituted by one to two $R_b$;

each $R_a$ and $R_b$ are independently chosen from $C_{1-5}$ alkyl, aryloxy, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_a$ or $R_b$ are optionally halogenated where possible;

each $R_3$ is chosen from $C_{1-5}$ alkyl, $C_{1-5}$ alkoxy, $C_{1-5}$ alkylthio, $C_{1-5}$ acyl, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-3}$ alkyl, wherein any of the above $R_3$ are optionally halogenated where possible;

$R_4$ is hydrogen; and and $R_5$ is hydrogen or methyl.

In a fourth embodiment there are provided compounds of the formula (I) as described immediately above and wherein:

t is 0–2;

$R_1$ is chosen from $C_{4-6}$ alkyl, amino, $C_{5-7}$ cycloalkyl, indanyl, indenyl, phenyl, naphthyl, tetrahydronaphthyl, pyridinyl, pyrimidinyl, pyrazinyl, pyridazinyl, pyrrolidinyl, pyrrolinyl, tetrahydrofuranyl, piperidinyl and dioxalanyl, each optionally substituted by one to two $R_a$;

$R_2$ is chosen from heteroaryl chosen from pyridinyl, pyrimidinyl, pyrazinyl and pyridazinyl and heterocyclyl chosen from morpholinyl, thiomorpholinyl, pyranyl, piperidinyl and piperazinyl, each optionally substituted by $R_b$;

each $R_a$ and $R_b$ are independently chosen from $C_{1-5}$ alkyl, aryloxy, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_a$ or $R_b$ are optionally halogenated where possible;

each $R_3$ is chosen from $C_{1-5}$ alkyl, $C_{1-5}$ alkoxy, $C_{1-5}$ alkylthio, $C_{1-5}$ acyl, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-3}$ alkyl, wherein any of the above $R_3$ are optionally halogenated where possible.

In a fifth embodiment there are provided compounds of the formula (I) as described immediately above and wherein:

t is 0or 1;

$R_1$ is chosen from $C_4$ alkyl, amino, $C_{5-6}$ cycloalkyl, indanyl, indenyl, phenyl, naphthyl, tetrahydronaphthyl, pyridinyl, tetrahydrofuranyl and piperidinyl, each optionally substituted by one to two $R_a$;

$R_2$ is chosen from morpholinyl, thiomorpholinyl, pyranyl, piperidinyl and piperazinyl, each optionally substituted by $R_b$;

each $R_a$ and $R_b$ are independently chosen from $C_{1-5}$ alkyl, $C_{1-5}$ alkoxy, $C_{4-6}$ alkoxycarbonyl, hydroxy, halogen, trifluoromethyl, nitro, nitrile and amino wherein any of the above $R_a$ or $R_b$ are optionally halogenated where possible;

each $R_3$ is chosen from $C_{1-3}$ alkyl, $C_{1-3}$ alkoxy, hydroxy, halogen, trifluoromethyl, nitro, nitrile and amino wherein any of the above $R_3$ are optionally halogenated where possible.

In a sixth embodiment there are provided compounds of the formula (I) as described immediately above and wherein:
n is 1 or 2;
m is 0;
$R_1$ is chosen from amino, cyclohexyl, indanyl, indenyl, phenyl, naphthyl, tetrahydronaphthyl, pyridinyl, tetrahydrofuranyl and piperidinyl, each optionally substituted by one to two $R_a$.

In a seventh embodiment there are provided compounds of the formula (I) as described immediately above and wherein:
each $R_a$ and $R_b$ are independently chosen from methyl, methoxy, tert-butoxycarbonyl, fluoro, trifluoromethyl and amino; and
each $R_3$ is chosen from methyl, methoxy, fluoro, ifluoromethyl and amino.

In an eight embodiment there are provided compounds of the formula (I) as described immediately above and wherein:
$R_1$ is chosen from t-butyl, amino, cyclohexyl and phenyl, the phenyl is optionally substituted by one to two $R_a$ and $R_3$ is chosen from methyl and fluoro.

In a ninth embodiment there are provided compounds of the formula (I) as described in the fifth embodiment above and wherein:
t is 0;
m is 0 or 1;
$R_1$ is chosen from cyclopentyl optionally substituted by one to two $R_a$.

In a tenth embodiment there are provided compounds of the formula (I) as described immediately above and wherein:
each $R_a$ and $R_b$ are independently chosen from methyl, methoxy, tert-butoxycarbonyl, fluoro, trifluoromethyl and amino.

In an eleventh embodiment there are provided compounds of the formula (I) as described second embodiment above and wherein:
$R_2$ is mono-or di $C_{1-5}$ alkyl amino further substituted by mono-or di $C_{1-5}$ alkyl amino.

In an twelfth embodiment there are provided compounds of the formula (I) as described second embodiment above and wherein:
$R_2$ is chosen from $C_{1-3}$ alkylthio or $C_{1-3}$ alkoxy each further substituted by mono-or di $C_{1-5}$ alkyl amino.

The following are representative compounds of the formula (I):

TABLE I

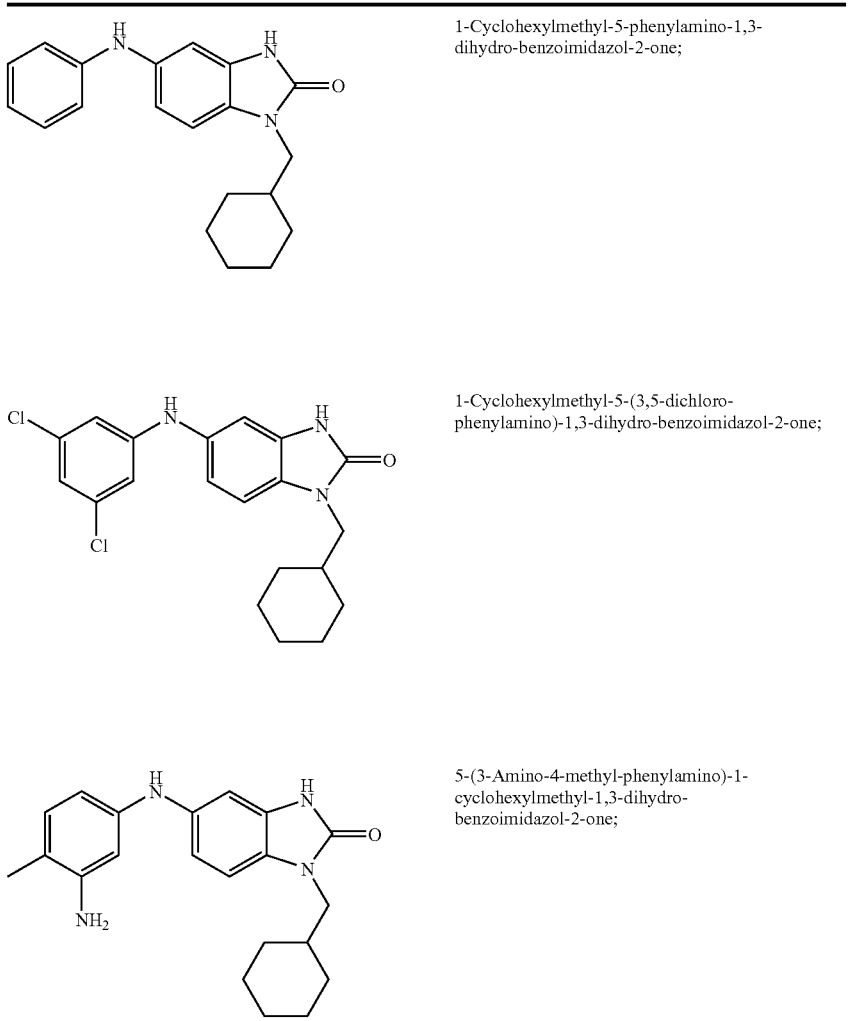

1-Cyclohexylmethyl-5-phenylamino-1,3-dihydro-benzoimidazol-2-one;

1-Cyclohexylmethyl-5-(3,5-dichloro-phenylamino)-1,3-dihydro-benzoimidazol-2-one;

5-(3-Amino-4-methyl-phenylamino)-1-cyclohexylmethyl-1,3-dihydro-benzoimidazol-2-one;

TABLE I-continued
| | |
|---|---|
| 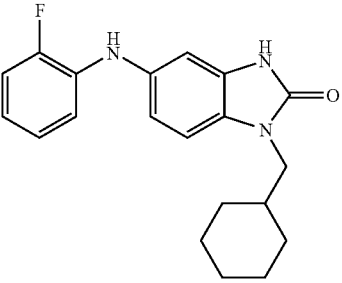 | 1-Cyclohexylmethyl-5-(2-fluoro-phenylamino)-1,3-dihydro-benzoimidazol-2-one; |
| 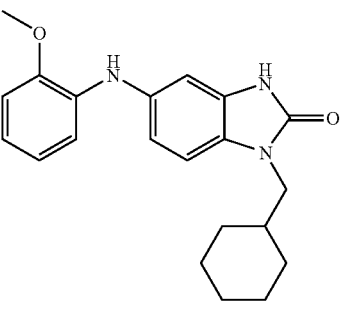 | 1-Cyclohexylmethyl-5-(2-methoxy-phenylamino)-1,3-dihydro-benzoimidazol-2-one; |
| 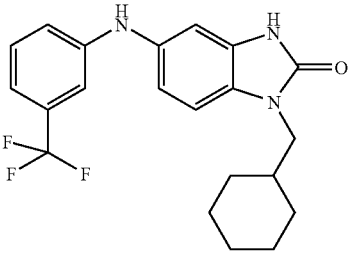 | 1-Cyclohexylmethyl-5-(3-trifluoromethyl-phenylamino)-1,3-dihydro-benzoimidazol-2-one; |
| 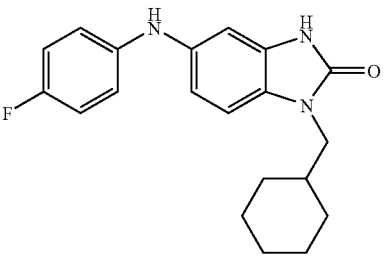 | 1-Cyclohexylmethyl-5-(4-fluoro-phenylamino)-1,3-dihydro-benzoimidazol-2-one; |
| 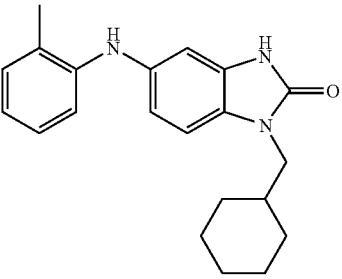 | 1-Cyclohexylmethyl-5-o-tolylamino-1,3-dihydro-benzoimidazol-2-one; |

TABLE I-continued
| | |
|---|---|
| 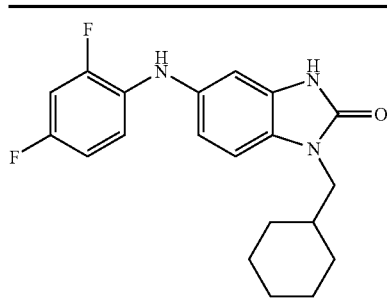 | 1-Cyclohexylmethyl-5-(2,4-difluoro-phenylamino)-1,3-dihydro-benzoimidazol-2-one; |
| 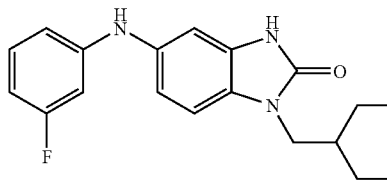 | 1-Cyclohexylmethyl-5-(3-fluoro-phenylamino)-1,3-dihydro-benzoimidazol-2-one; |
| 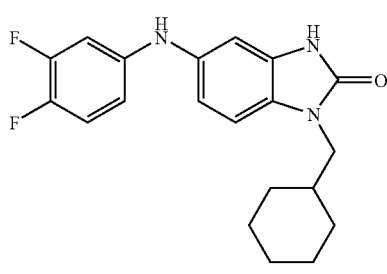 | 1-Cyclohexylmethyl-5-(3,4-difluoro-phenylamino)-1,3-dihydro-benzoimidazol-2-one; |
| 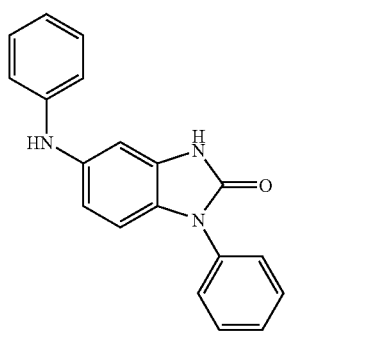 | 1-Phenyl-5-phenylamino-1,3-dihydro-benzoimidazol-2-one; |
| 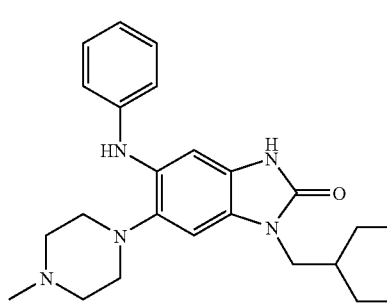 | 1-Cyclohexylmethyl-6-(4-methyl-piperazin-1-yl)-5-phenylamino-1,3-dihydro-benzoimidazol-2-one; |

TABLE I-continued
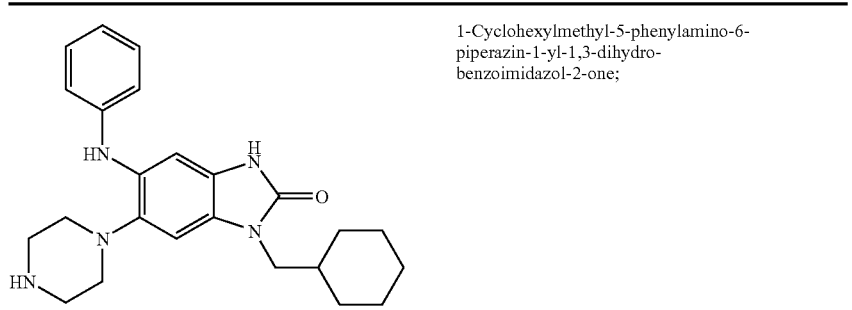
1-Cyclohexylmethyl-5-phenylamino-6-piperazin-1-yl-1,3-dihydro-benzoimidazol-2-one;
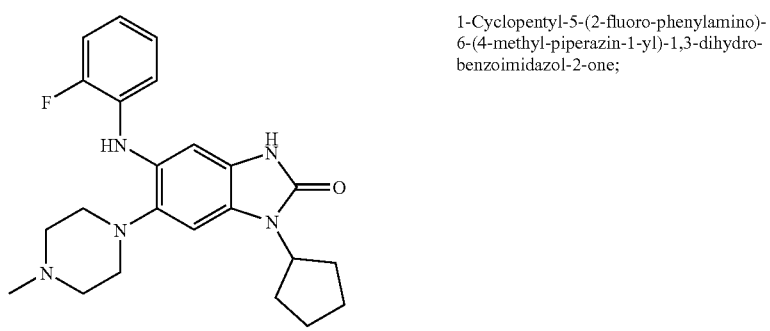
1-Cyclopentyl-5-(2-fluoro-phenylamino)-6-(4-methyl-piperazin-1-yl)-1,3-dihydro-benzoimidazol-2-one;
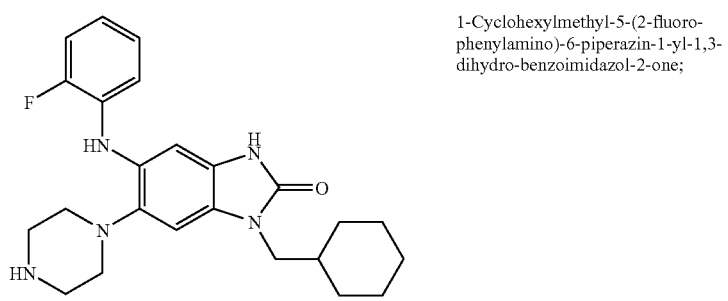
1-Cyclohexylmethyl-5-(2-fluoro-phenylamino)-6-piperazin-1-yl-1,3-dihydro-benzoimidazol-2-one;
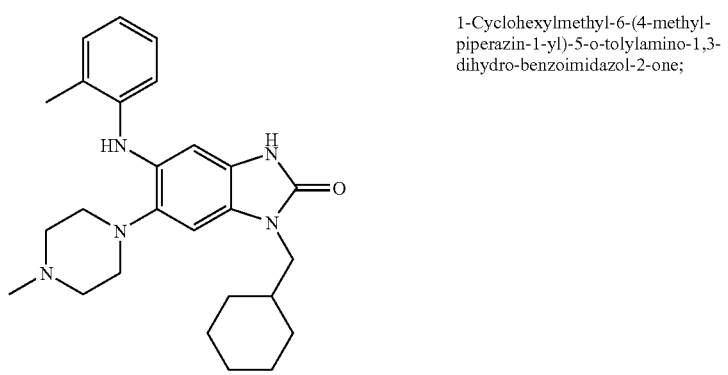
1-Cyclohexylmethyl-6-(4-methyl-piperazin-1-yl)-5-o-tolylamino-1,3-dihydro-benzoimidazol-2-one;

TABLE I-continued
| | |
|---|---|
| 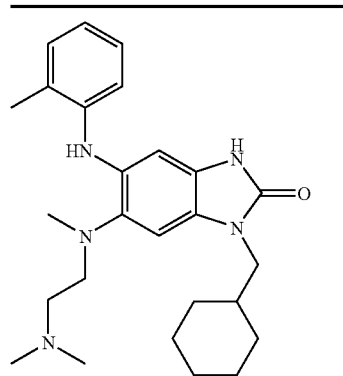 | 1-Cyclohexylmethyl-6-[(2-dimethylamino-ethyl)-methyl-amino]-5-o-tolylamino-1,3-dihydro-benzoimidazol-2-one; |
| 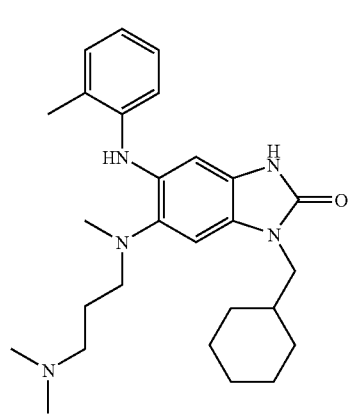 | 1-Cyclohexylmethyl-6-[(3-dimethylamino-propyl)-methyl-amino]-5-o-tolylamino-1,3-dihydro-benzoimidazol-2-one; |
| 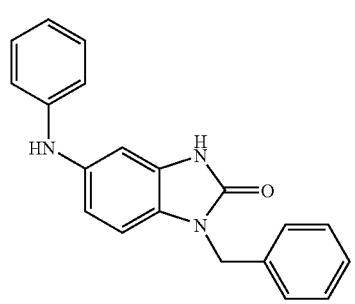 | 5-anilino-1-benzyl-1,3-dihydro-2H-benzimidazol-2-one; |
| 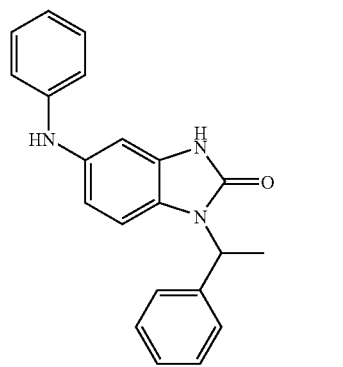 | 5-anilino-1-(1-phenylethyl)-1,3-dihydro-2H-benzimidazol-2-one; |

TABLE I-continued
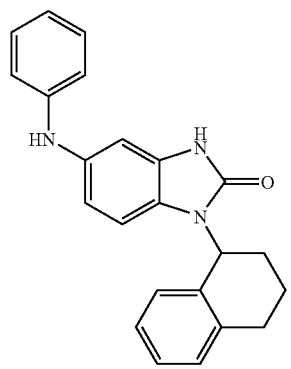
5-anilino-1-(1,2,3,4-tetrahydronaphthalen-1-yl)-1,3-dihydro-2H-benzimidazol-2-one;
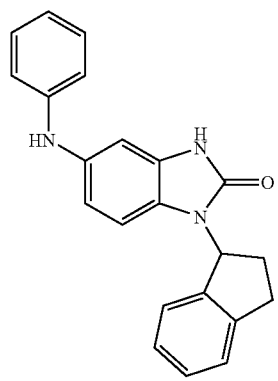
5-anilino-1-(2,3-dihydro-1H-inden-1-yl)-1,3-dihydro-2H-benzimidazol-2-one;
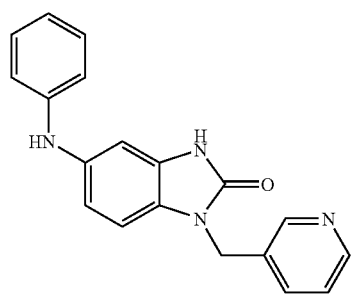
5-anilino-1-(pyridin-3-ylmethyl)-1,3-dihydro-2H-benzimidazol-2-one;
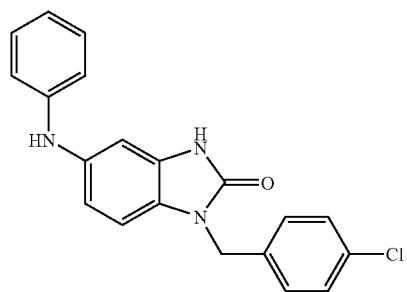
5-anilino-1-(4-chlorobenzyl)-1,3-dihydro-2H-benzimidazol-2-one;

TABLE I-continued
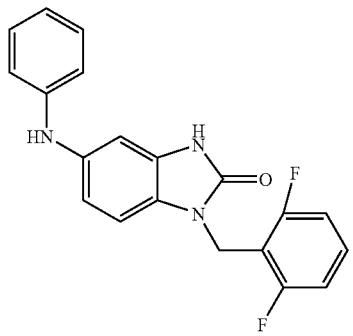
5-anilino-1-(2,6-difluorobenzyl)-1,3-dihydro-2H-benzimidazol-2-one
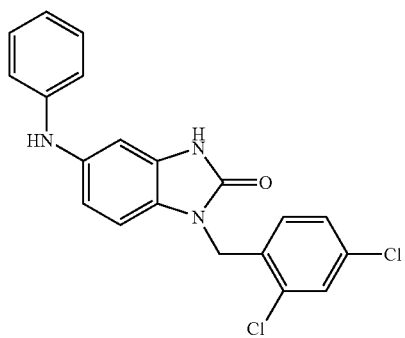
5-anilino-1-(2,4-dichlorobenzyl)-1,3-dihydro-2H-benzimidazol-2-one;
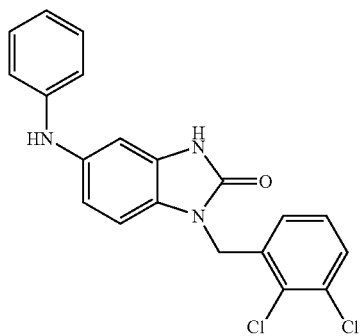
5-anilino-1-(2,3-dichlorobenzyl)-1,3-dihydro-2H-benzimidazol-2-one;
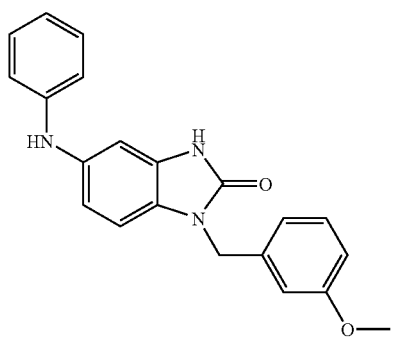
5-anilino-1-(3-methoxybenzyl)-1,3-dihydro-2H-benzimidazol-2-one;

TABLE I-continued
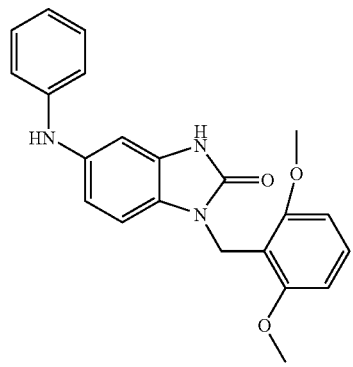
5-anilino-1-(2,6-dimethoxybenzyl)-1,3-dihydro-2H-benzimidazol-2-one;
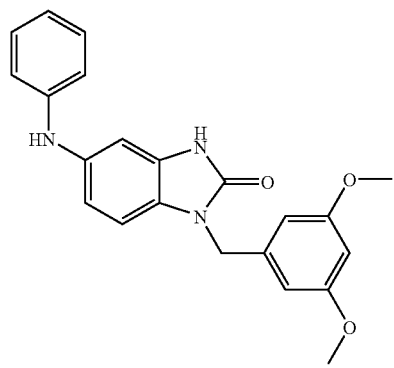
5-anilino-1-(3,5-dimethoxybenzyl)-1,3-dihydro-2H-benzimidazol-2-one;
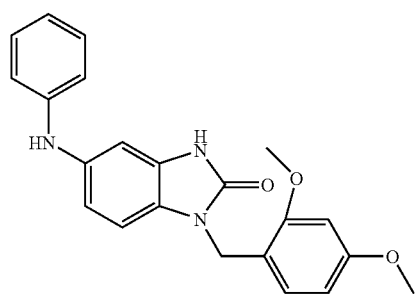
5-anilino-1-(2,4-dimethoxybenzyl)-1,3-dihydro-2H-benzimidazol-2-one;
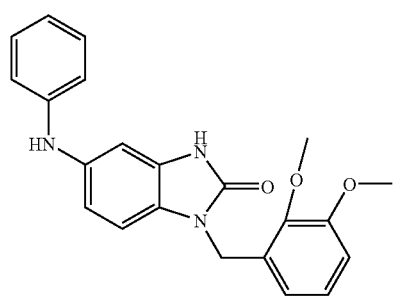
5-anilino-1-(2,3-dimethoxybenzyl)-1,3-dihydro-2H-benzimidazol-2-one;

TABLE I-continued
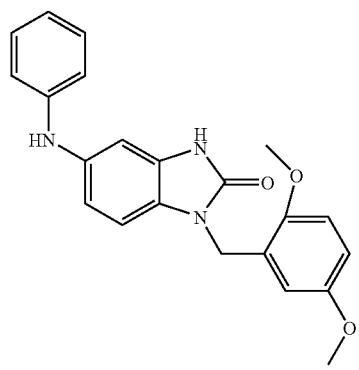
5-anilino-1-(2,5-dimethoxybenzyl)-1,3-dihydro-2H-benzimidazol-2-one;
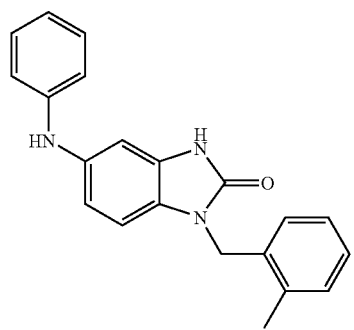
5-anilino-1-(2-methylbenzyl)-1,3-dihydro-2H-benzimidazol-2-one;
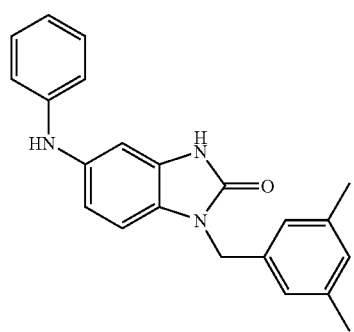
5-anilino-1-(3,5-dimethylbenzyl)-1,3-dihydro-2H-benzimidazol-2-one;
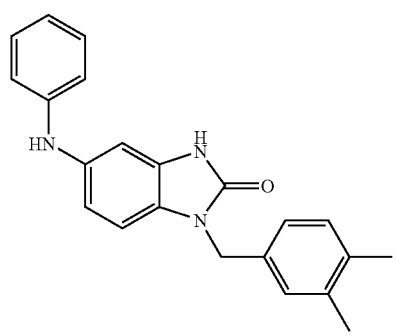
5-anilino-1-(3,4-dimethylbenzyl)-1,3-dihydro-2H-benzimidazol-2-one;

TABLE I-continued
| | |
|---|---|
| 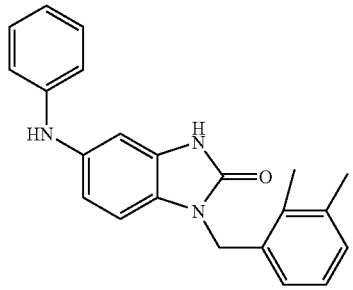 | 5-anilino-1-(2,3-dimethylbenzyl)-1,3-dihydro-2H-benzimidazol-2-one; |
| 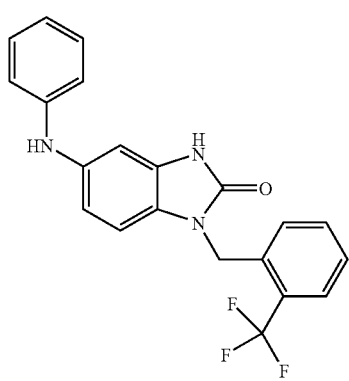 | 5-anilino-1-[2-(trifluoromethyl)benzyl]-1,3-dihydro-2H-benzimidazol-2-one; |
| 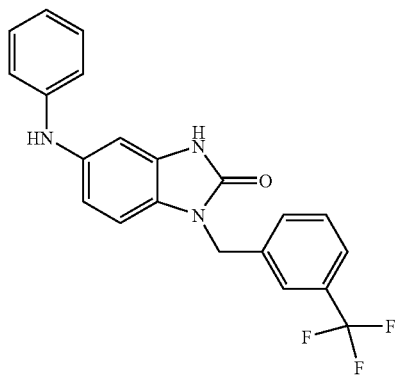 | 5-anilino-1-[3-(trifluoromethyl)benzyl]-1,3-dihydro-2H-benzimidazol-2-one; |
| 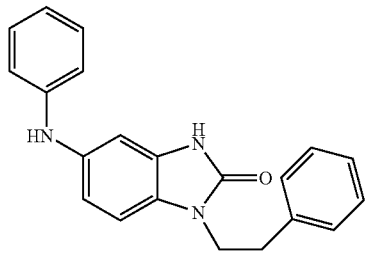 | 5-anilino-1-(2-phenylethyl)-1,3-dihydro-2H-benzimidazol-2-one; |
| 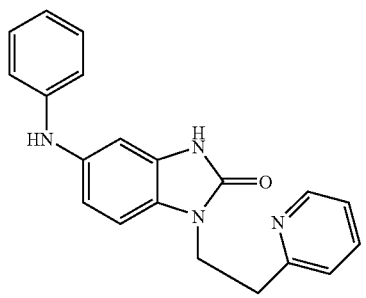 | 5-anilino-1-(2-pyridin-2-ylethyl)-1,3-dihydro-2H-benzimidazol-2-one; |

TABLE I-continued
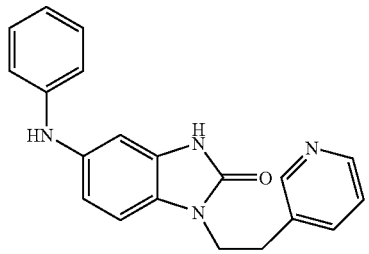
5-anilino-1-(2-pyridin-3-ylethyl)-1,3-dihydro-2H-benzimidazol-2-one;
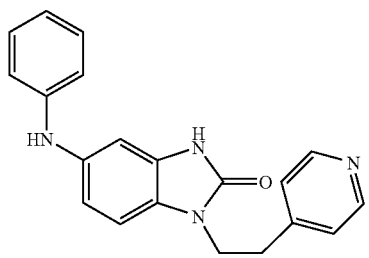
5-anilino-1-(2-pyridin-4-ylethyl)-1,3-dihydro-2H-benzimidazol-2-one;
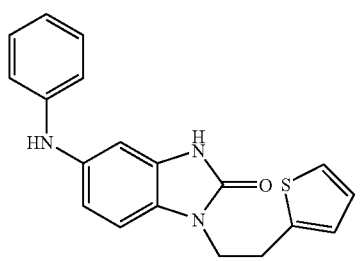
5-anilino-1-(2-thien-2-ylethyl)-1,3-dihydro-2H-benzimidazol-2-one;
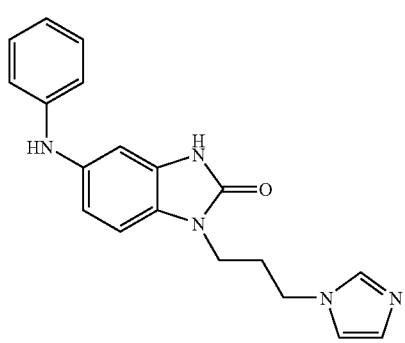
5-anilino-1-[3-(1H-imidazol-1-yl)propyl]-1,3-dihydro-2H-benzimidazol-2-one;
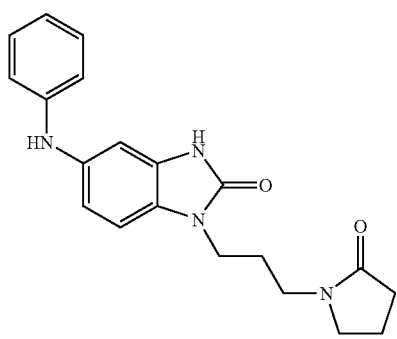
5-anilino-1-[3-(2-oxopyrrolidin-1-yl)propyl]-1,3-dihydro-2H-benzimidazol-2-one;

TABLE I-continued
| | |
|---|---|
| 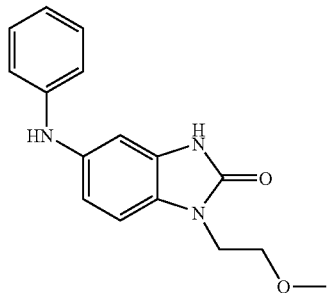 | 5-anilino-1-(2-methoxyethyl)-1,3-dihydro-2H-benzimidazol-2-one; |
| 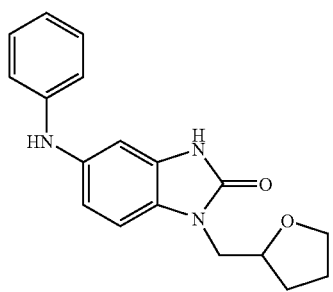 | 5-anilino-1-(tetrahydrofuran-2-ylmethyl)-1,3-dihydro-2H-benzimidazol-2-one; |
| 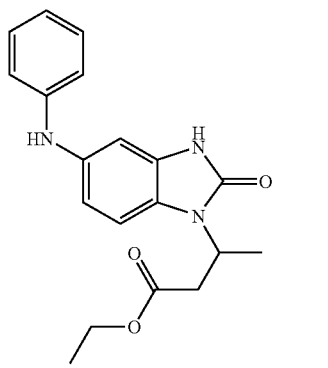 | ethyl 3-(5-anilino-2-oxo-2,3-dihydro-1H-benzimidazol-1-yl)butanoate; |
| 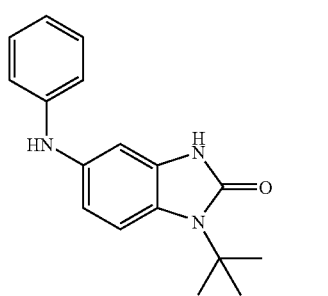 | 5-anilino-1-tert-butyl-1,3-dihydro-2H-benzimidazol-2-one; |
| 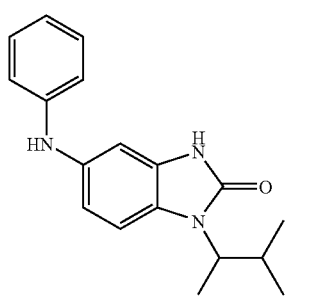 | 5-anilino-1-(1,2-dimethylpropyl)-1,3-dihydro-2H-benzimidazol-2-one; |

TABLE I-continued
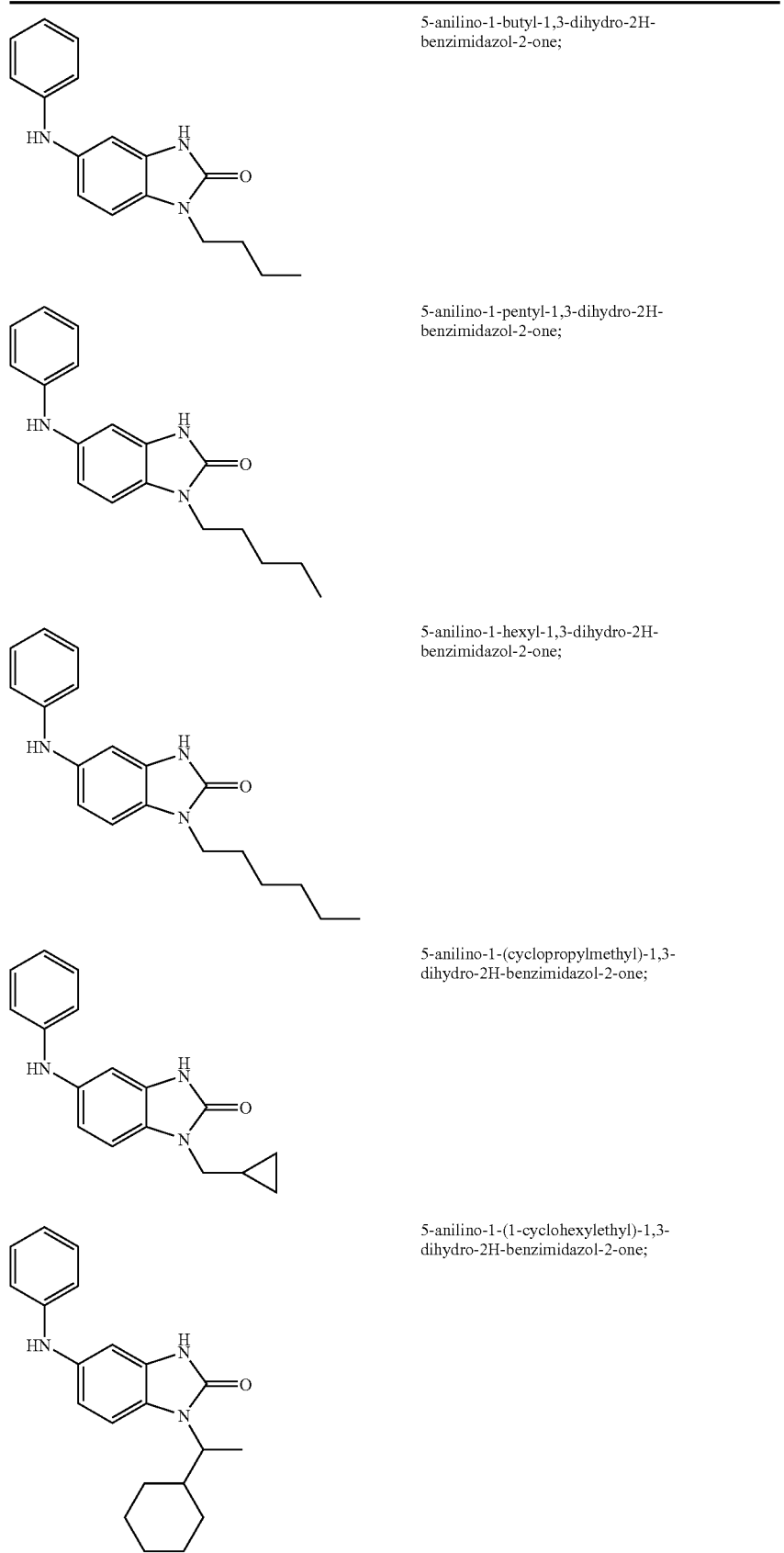
5-anilino-1-butyl-1,3-dihydro-2H-benzimidazol-2-one;
5-anilino-1-pentyl-1,3-dihydro-2H-benzimidazol-2-one;
5-anilino-1-hexyl-1,3-dihydro-2H-benzimidazol-2-one;
5-anilino-1-(cyclopropylmethyl)-1,3-dihydro-2H-benzimidazol-2-one;
5-anilino-1-(1-cyclohexylethyl)-1,3-dihydro-2H-benzimidazol-2-one;

TABLE I-continued
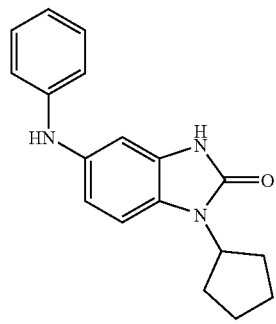
5-anilino-1-cyclopentyl-1,3-dihydro-2H-benzimidazol-2-one;
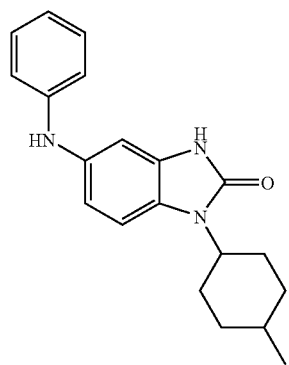
5-anilino-1-(4-methylcyclohexyl)-1,3-dihydro-2H-benzimidazol-2-one;
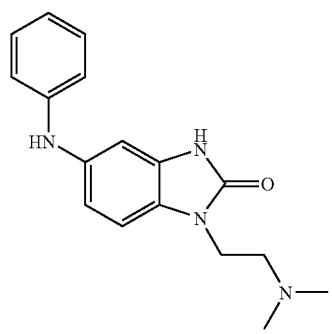
5-anilino-1-[2-(dimethylamino)ethyl]-1,3-dihydro-2H-benzimidazol-2-one;
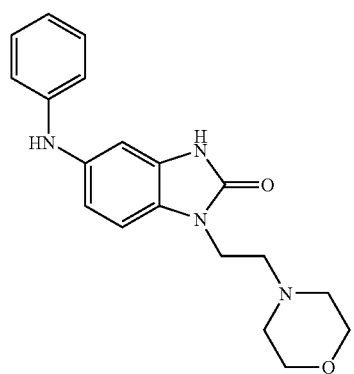
5-anilino-1-(2-morpholin-4-ylethyl)-1,3-dihydro-2H-benzimidazol-2-one;

TABLE I-continued
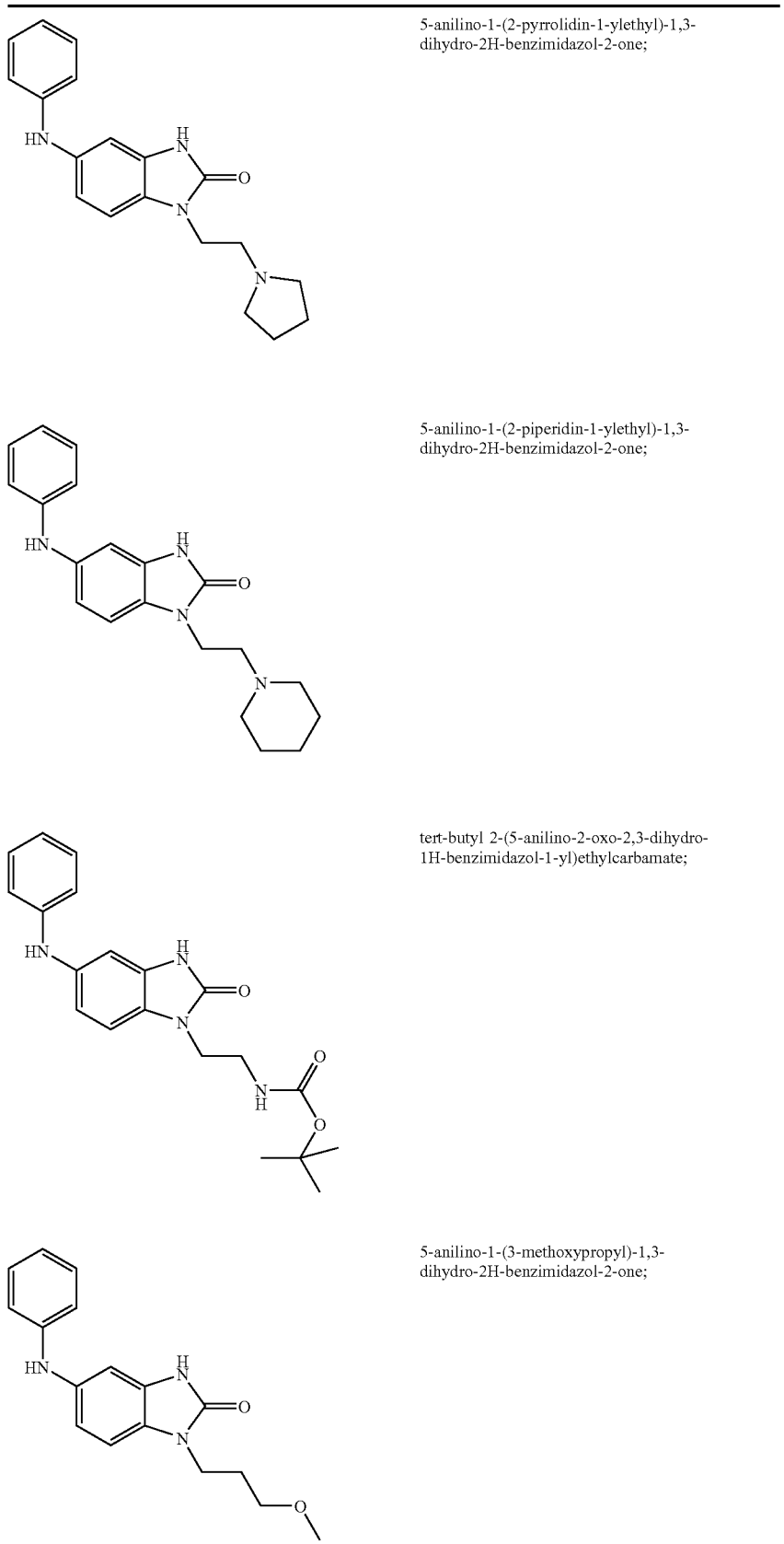
5-anilino-1-(2-pyrrolidin-1-ylethyl)-1,3-dihydro-2H-benzimidazol-2-one;
5-anilino-1-(2-piperidin-1-ylethyl)-1,3-dihydro-2H-benzimidazol-2-one;
tert-butyl 2-(5-anilino-2-oxo-2,3-dihydro-1H-benzimidazol-1-yl)ethylcarbamate;
5-anilino-1-(3-methoxypropyl)-1,3-dihydro-2H-benzimidazol-2-one;

TABLE I-continued
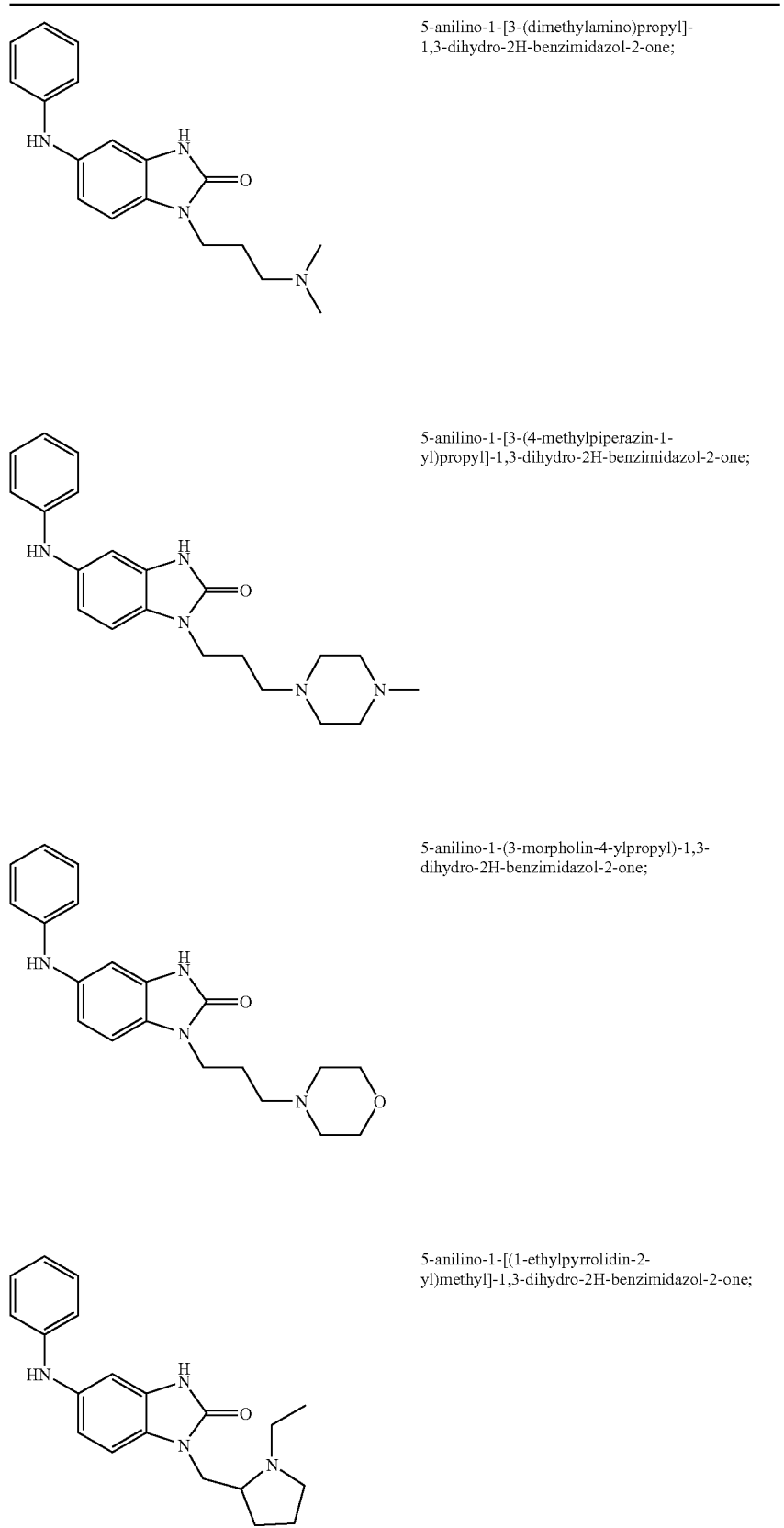
5-anilino-1-[3-(dimethylamino)propyl]-1,3-dihydro-2H-benzimidazol-2-one;
5-anilino-1-[3-(4-methylpiperazin-1-yl)propyl]-1,3-dihydro-2H-benzimidazol-2-one;
5-anilino-1-(3-morpholin-4-ylpropyl)-1,3-dihydro-2H-benzimidazol-2-one;
5-anilino-1-[(1-ethylpyrrolidin-2-yl)methyl]-1,3-dihydro-2H-benzimidazol-2-one;

TABLE I-continued

| Structure | Name |
|---|---|
| (structure) | 5-anilino-1-[2-(1-methylpyrrolidin-2-yl)ethyl]-1,3-dihydro-2H-benzimidazol-2-one; |
| (structure) | ethyl 4-(5-anilino-2-oxo-2,3-dihydro-1H-benzimidazol-1-yl)piperidine-1-carboxylate; | or the pharmaceutically acceptable acids and salts or isomers thereof.

The following are compounds of the invention which may be made by the methods provided in the general schemes and working examples, and methods known in the art:

TABLE II

| Structure | Name |
|---|---|
| (structure) | 1-Cyclohexylmethyl-5-p-tolylamino-1,3-dihydro-benzoimidazol-2-one; |
| (structure) | 5-anilino-1-(1-methyl-1-phenylethyl)-1,3-dihydro-2H-benzimidazol-2-one; |

TABLE II-continued
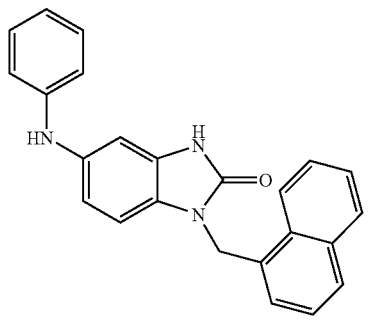
5-anilino-1-(1-naphthylmethyl)-1,3-dihydro-2H-benzimidazol-2-one;
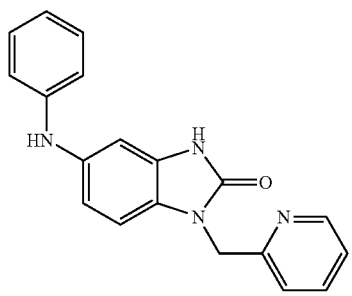
5-anilino-1-(pyridin-2-ylmethyl)-1,3-dihydro-2H-benzimidazol-2-one;
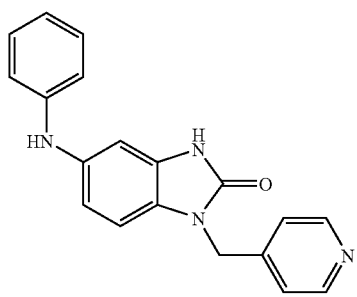
5-anilino-1-(pyridin-4-ylmethyl)-1,3-dihydro-2H-benzimidazol-2-one;
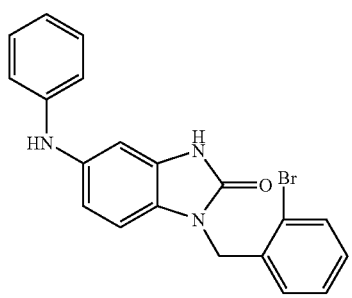
5-anilino-1-(2-bromobenzyl)-1,3-dihydro-2H-benzimidazol-2-one;
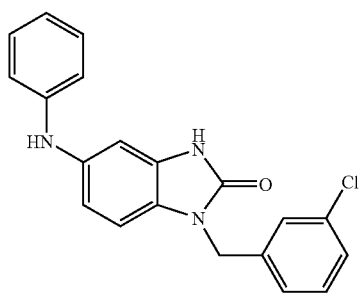
5-anilino-1-(3-chlorobenzyl)-1,3-dihydro-2H-benzimidazol-2-one;

TABLE II-continued
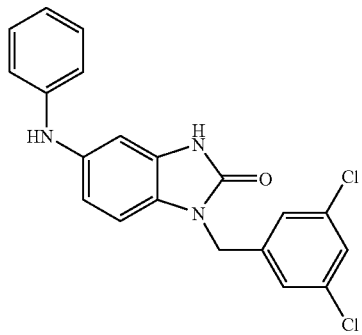
5-anilino-1-(3,5-dichlorobenzyl)-1,3-dihydro-2H-benzimidazol-2-one;
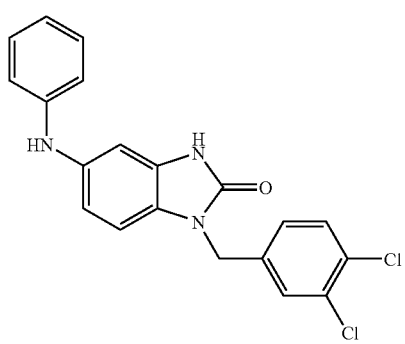
5-anilino-1-(3,4-dichlorobenzyl)-1,3-dihydro-2H-benzimidazol-2-one;
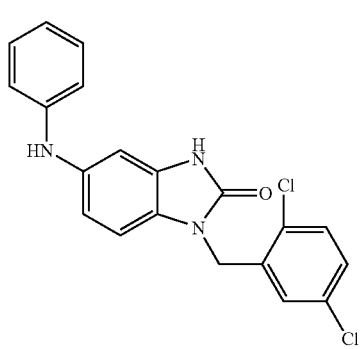
5-anilino-1-(2,5-dichlorobenzyl)-1,3-dihydro-2H-benzimidazol-2-one;
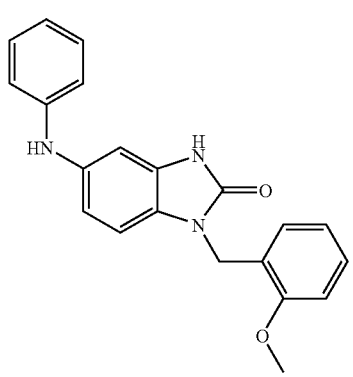
5-anilino-1-(2-methoxybenzyl)-1,3-dihydro-2H-benzimidazol-2-one;

TABLE II-continued
5-anilino-1-(4-methoxybenzyl)-1,3-dihydro-2H-benzimidazol-2-one;
5-anilino-1-(3,4-dimethoxybenzyl)-1,3-dihydro-2H-benzimidazol-2-one;
5-anilino-1-(3-methylbenzyl)-1,3-dihydro-2H-benzimidazol-2-one;
5-anilino-1-(4-methylbenzyl)-1,3-dihydro-2H-benzimidazol-2-one;
5-anilino-1-(2,4-dimethylbenzyl)-1,3-dihydro-2H-benzimidazol-2-one;

TABLE II-continued
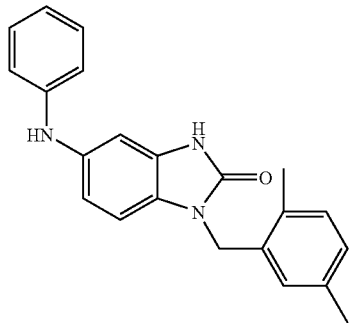
5-anilino-1-(2,5-dimethylbenzyl)-1,3-dihydro-2H-benzimidazol-2-one;
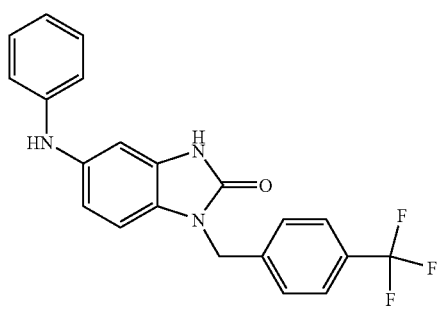
5-anilino-1-[4-(trifluoromethyl)benzyl]-1,3-dihydro-2H-benzimidazol-2-one;
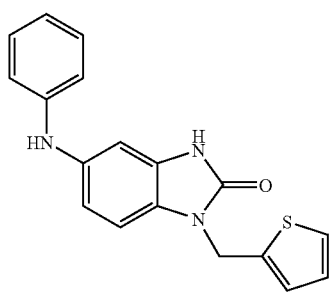
5-anilino-1-(thien-2-ylmethyl)-1,3-dihydro-2H-benzimidazol-2-one;
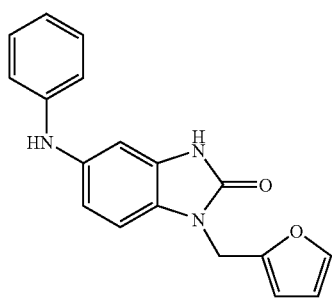
5-anilino-1-(2-furylmethyl)-1,3-dihydro-2H-benzimidazol-2-one;
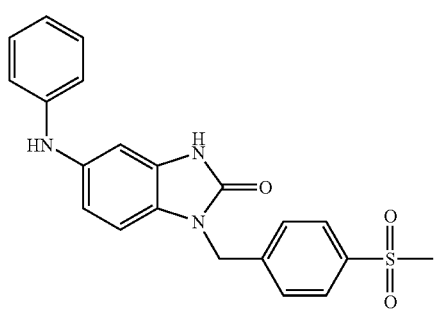
5-anilino-1-[4-(methylsulfonyl)benzyl]-1,3-dihydro-2H-benzimidazol-2-one;

TABLE II-continued
| | |
|---|---|
| 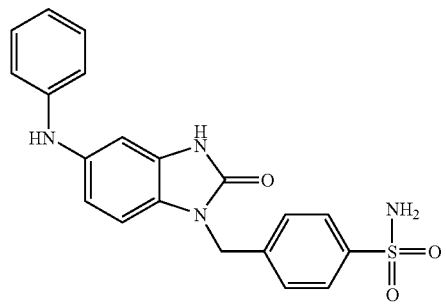 | 4-[(5-anilino-2-oxo-2,3-dihydro-1H-benzimidazol-1-yl)methyl]benzenesulfonamide; |
| 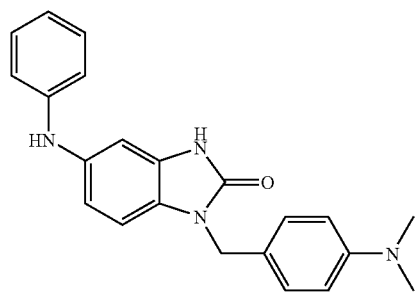 | 5-anilino-1-[4-(dimethylamino)benzyl]-1,3-dihydro-2H-benzimidazol-2-one; |
| 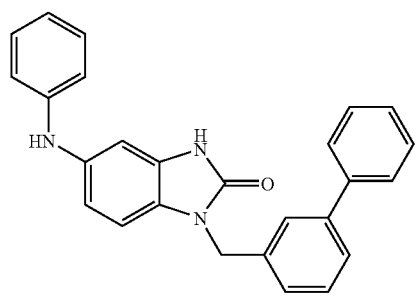 | 5-anilino-1-(1,1'-biphenyl-3-ylmethyl)-1,3-dihydro-2H-benzimidazol-2-one; |
| 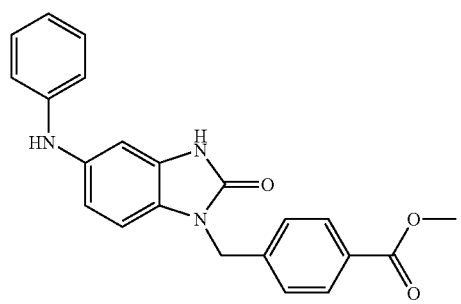 | methyl 4-[(5-anilino-2-oxo-2,3-dihydro-1H-benzimidazol-1-yl)methyl]benzoate; |
| 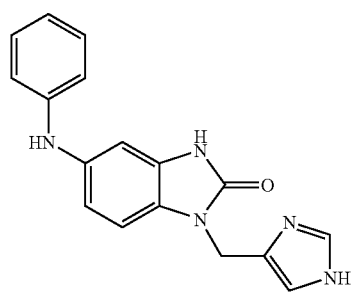 | 5-anilino-1-(1H-imidazol-4-ylmethyl)-1,3-dihydro-2H-benzimidazol-2-one; |

TABLE II-continued
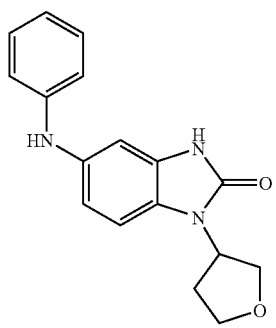
5-anilino-1-tetrahydrofuran-3-yl-1,3-dihydro-2H-benzimidazol-2-one;
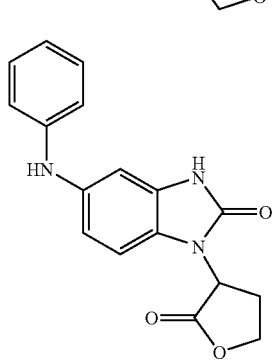
5-anilino-1-(2-oxotetrahydrofuran-3-yl)-1,3-dihydro-2H-benzimidazol-2-one;
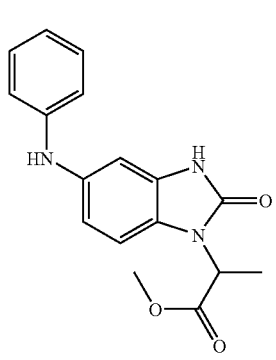
methyl 2-(5-anilino-2-oxo-2,3-dihydro-1H-benzimidazol-1-yl)propanoate;
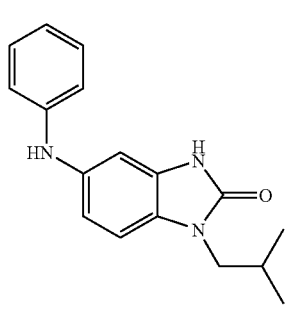
5-anilino-1-isobutyl-1,3-dihydro-2H-benzimidazol-2-one;
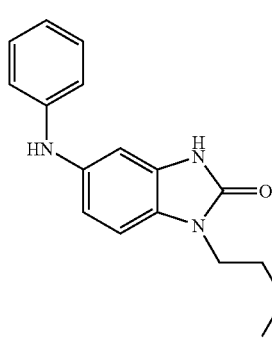
5-anilino-1-(3-methylbutyl)-1,3-dihydro-2H-benzimidazol-2-one;

TABLE II-continued
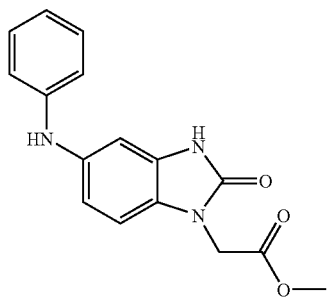
methyl (5-anilino-2-oxo-2,3-dihydro-1H-benzimidazol-1-yl)acetate;
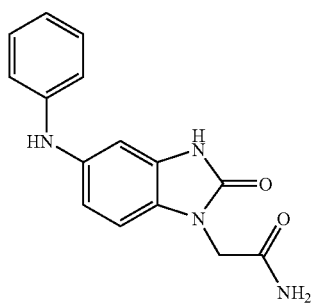
2-(5-anilino-2-oxo-2,3-dihydro-1H-benzimidazol-1-yl)acetamide;
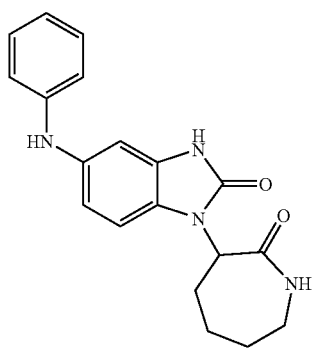
5-anilino-1-(2-oxoazepan-3-yl)-1,3-dihydro-2H-benzimidazol-2-one;
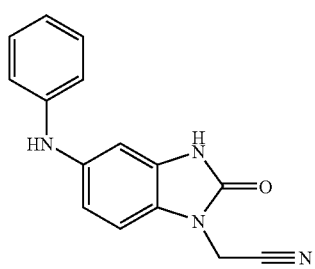
(5-anilino-2-oxo-2,3-dihydro-1H-benzimidazol-1-yl)acetonitrile;
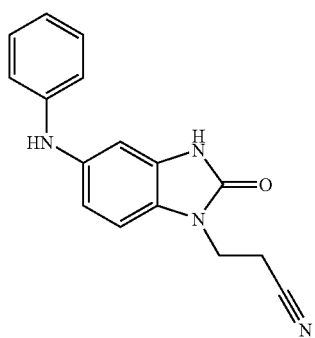
3-(5-anilino-2-oxo-2,3-dihydro-1H-benzimidazol-1-yl)propanenitrile;

TABLE II-continued
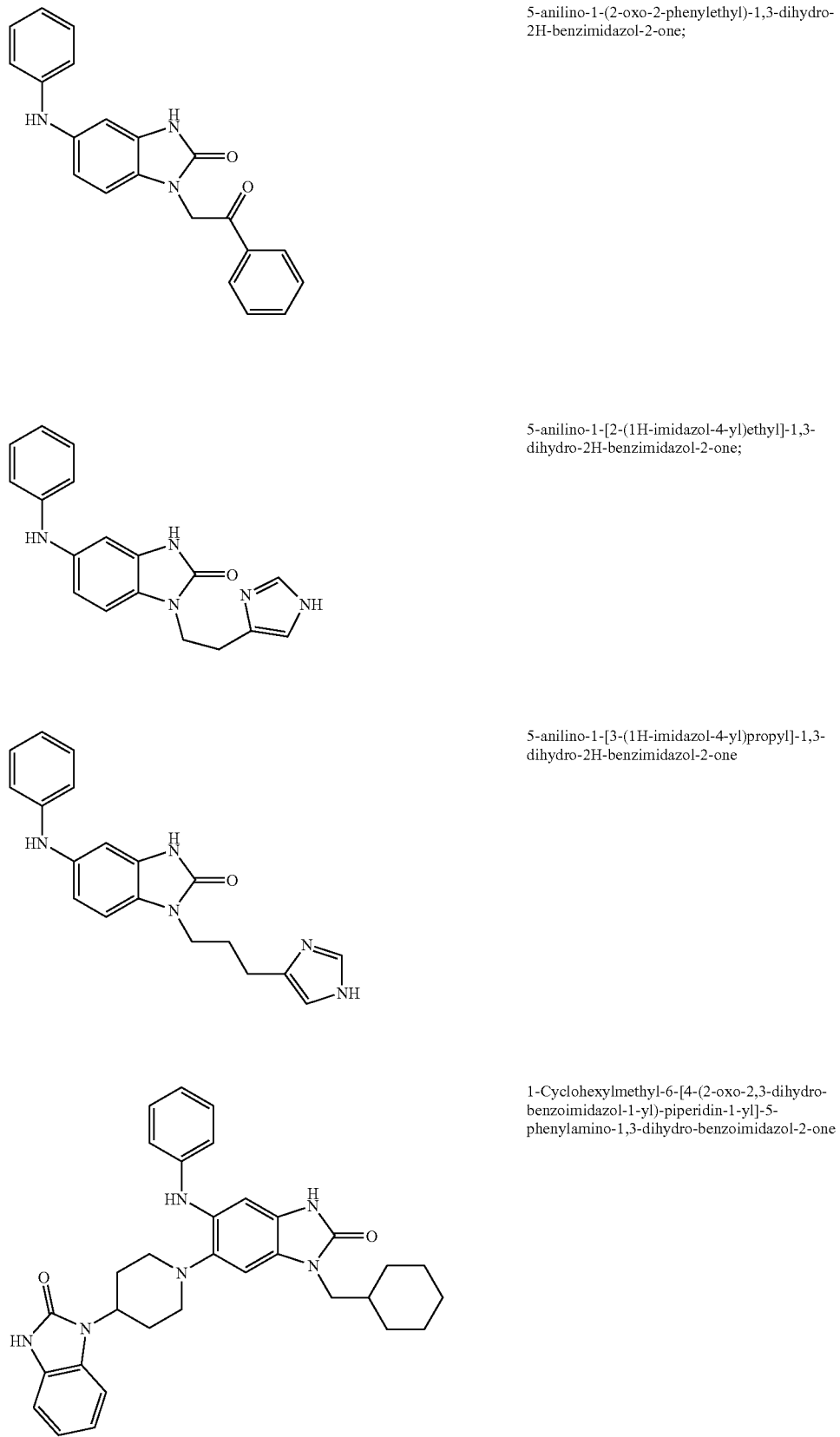
5-anilino-1-(2-oxo-2-phenylethyl)-1,3-dihydro-2H-benzimidazol-2-one;
5-anilino-1-[2-(1H-imidazol-4-yl)ethyl]-1,3-dihydro-2H-benzimidazol-2-one;
5-anilino-1-[3-(1H-imidazol-4-yl)propyl]-1,3-dihydro-2H-benzimidazol-2-one
1-Cyclohexylmethyl-6-[4-(2-oxo-2,3-dihydro-benzoimidazol-1-yl)-piperidin-1-yl]-5-phenylamino-1,3-dihydro-benzoimidazol-2-one TABLE II-continued

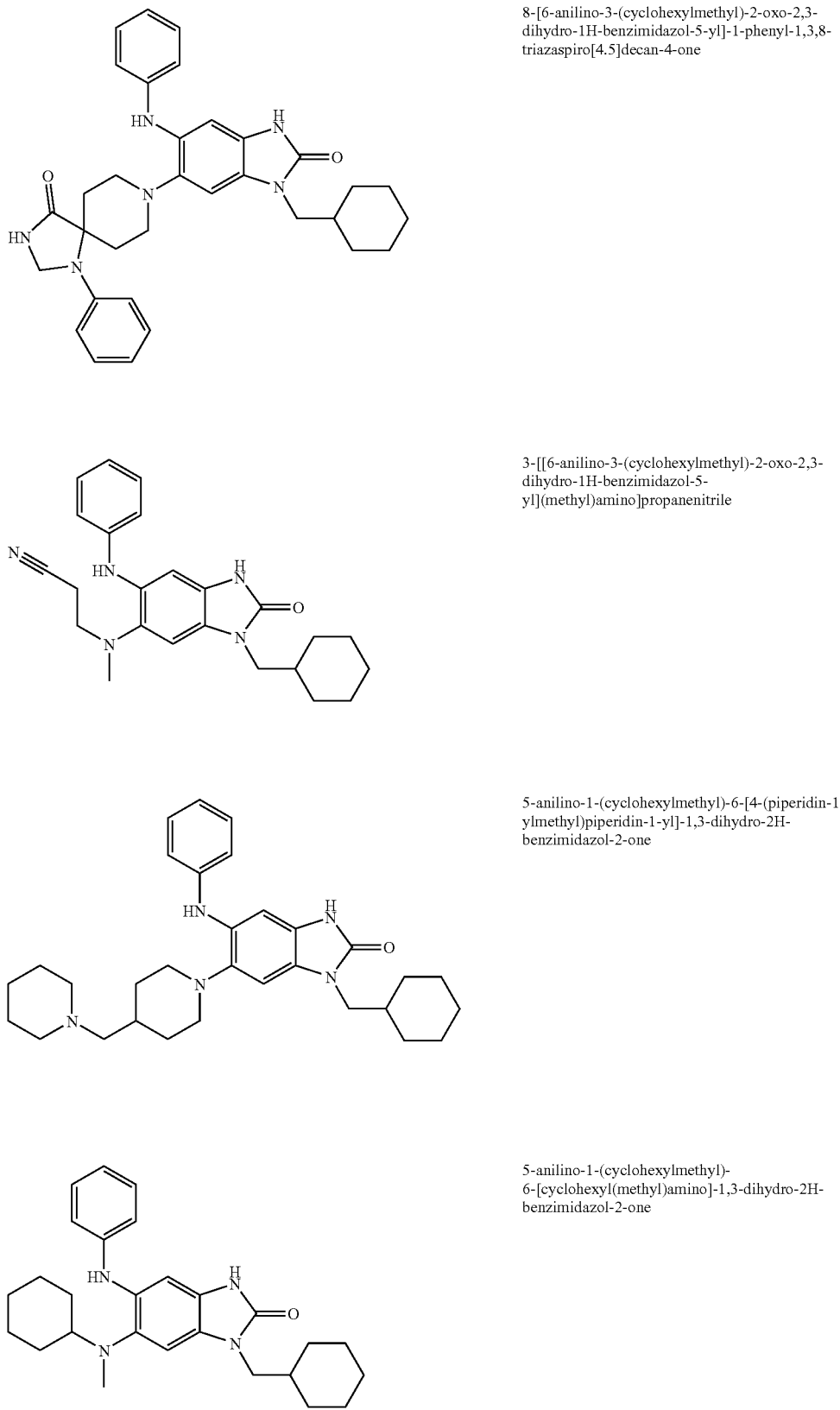

8-[6-anilino-3-(cyclohexylmethyl)-2-oxo-2,3-dihydro-1H-benzimidazol-5-yl]-1-phenyl-1,3,8-triazaspiro[4.5]decan-4-one 3-[[6-anilino-3-(cyclohexylmethyl)-2-oxo-2,3-dihydro-1H-benzimidazol-5-yl](methyl)amino]propanenitrile 5-anilino-1-(cyclohexylmethyl)-6-[4-(piperidin-1-ylmethyl)piperidin-1-yl]-1,3-dihydro-2H-benzimidazol-2-one 5-anilino-1-(cyclohexylmethyl)-6-[cyclohexyl(methyl)amino]-1,3-dihydro-2H-benzimidazol-2-one TABLE II-continued
| | |
|---|---|
| 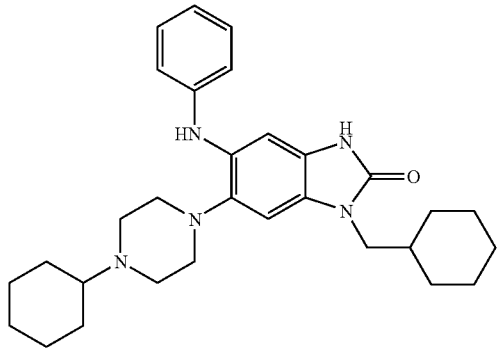 | 5-anilino-1-(cyclohexylmethyl)-6-(4-cyclohexylpiperazin-1-yl)-1,3-dihydro-2H-benzimidazol-2-one |
| 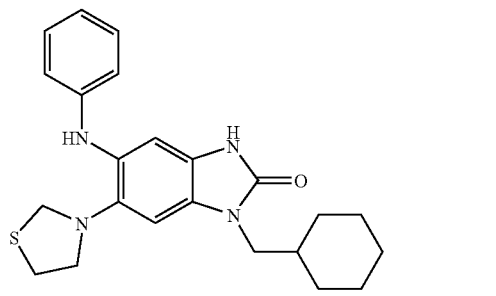 | 5-anilino-1-(cyclohexylmethyl)-6-(1,3-thiazolidin-3-yl)-1,3-dihydro-2H-benzimidazol-2-one |
| 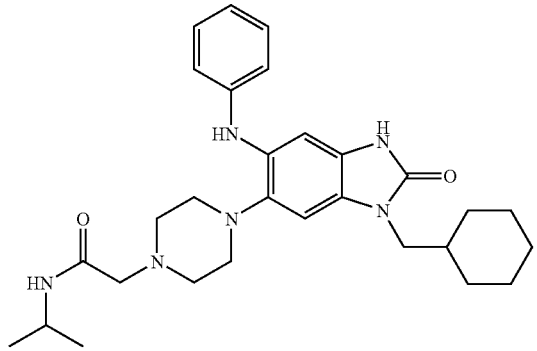 | 2-{4-[6-anilino-3-(cyclohexylmethyl)-2-oxo-2,3-dihydro-1H-benzimidazol-5-yl]piperazin-1-yl}-N-isopropylacetamide |
| 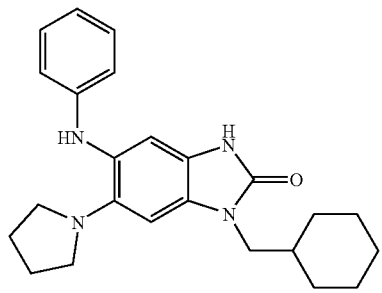 | 5-anilino-1-(cyclohexylmethyl)-6-pyrrolidin-1-yl-1,3-dihydro-2H-benzimidazol-2-one |

TABLE II-continued
| | |
|---|---|
| 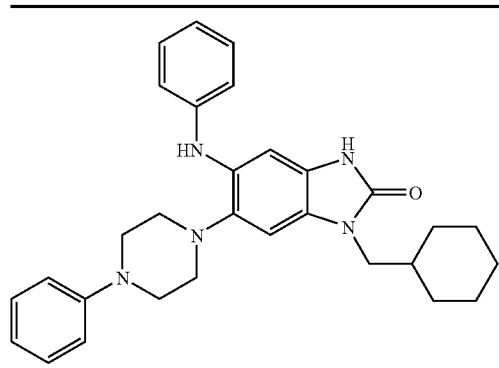 | 5-anilino-1-(cyclohexylmethyl)-6-(4-phenylpiperazin-1-yl)-1,3-dihydro-2H-benzimidazol-2-one |
| 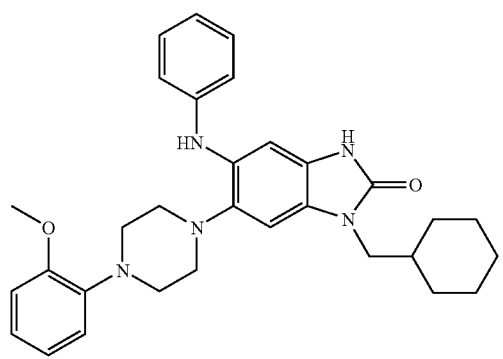 | 5-anilino-1-(cyclohexylmethyl)-6-[4-(2-methoxyphenyl)piperazin-1-yl]-1,3-dihydro-2H-benzimidazol-2-one |
| 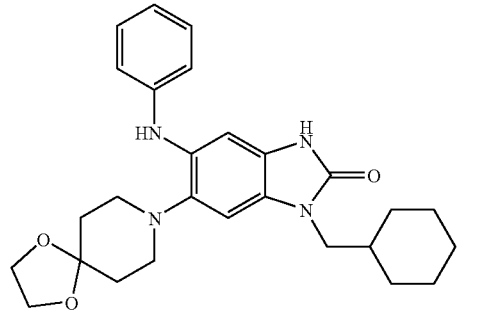 | 5-anilino-1-(cyclohexylmethyl)-6-(1,4-dioxa-8-azaspiro[4.5]dec-8-yl)-1,3-dihydro-2H-benzimidazol-2-one |
| 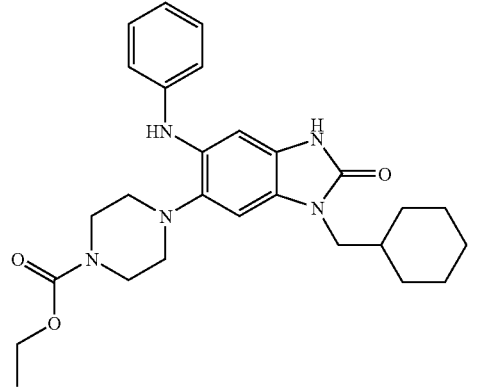 | ethyl 4-[6-anilino-3-(cyclohexylmethyl)-2-oxo-2,3-dihydro-1H-benzimidazol-5-yl]piperazine-1-carboxylate |

TABLE II-continued

| | |
|---|---|
| 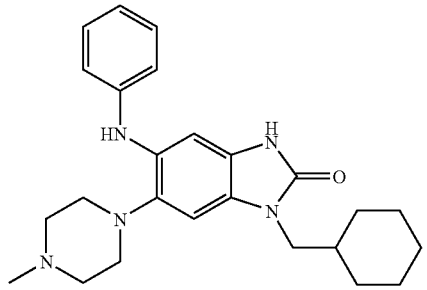 | 5-anilino-1-(cyclohexylmethyl)-6-(4-methylpiperazin-1-yl)-1,3-dihydro-2H-benzimidazol-2-one |
| 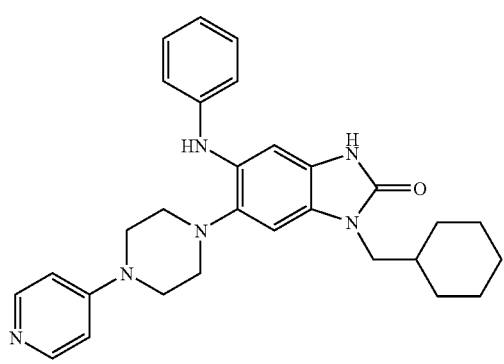 | 5-anilino-1-(cyclohexylmethyl)-6-(4-pyridin-4-ylpiperazin-1-yl)-1,3-dihydro-2H-benzimidazol-2-one |
| 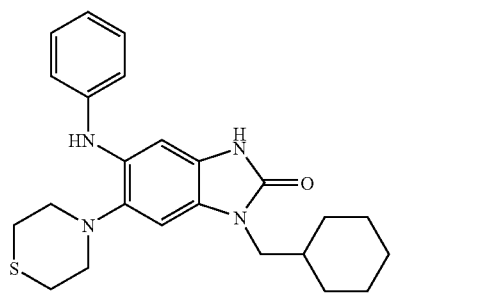 | 5-anilino-1-(cyclohexylmethyl)-6-thiomorpholin-4-yl-1,3-dihydro-2H-benzimidazol-2-one |
| 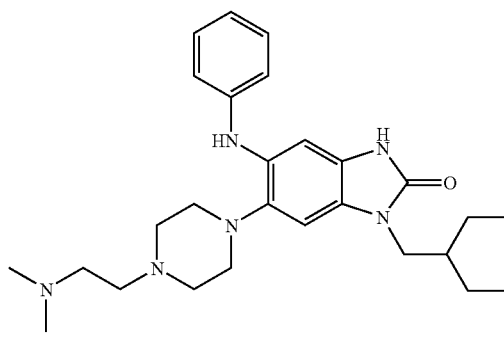 | 5-anilino-1-(cyclohexylmethyl)-6-{4-[2-(dimethylamino)ethyl]piperazin-1-yl}-1,3-dihydro-2H-benzimidazol-2-one |
| 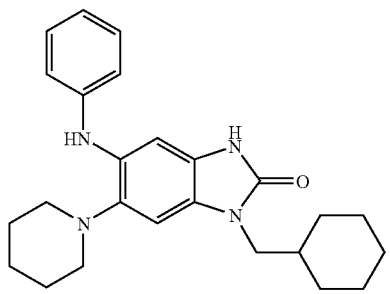 | 5-anilino-1-(cyclohexylmethyl)-6-piperidin-1-yl-1,3-dihydro-2H-benzimidazol-2-one |

TABLE II-continued

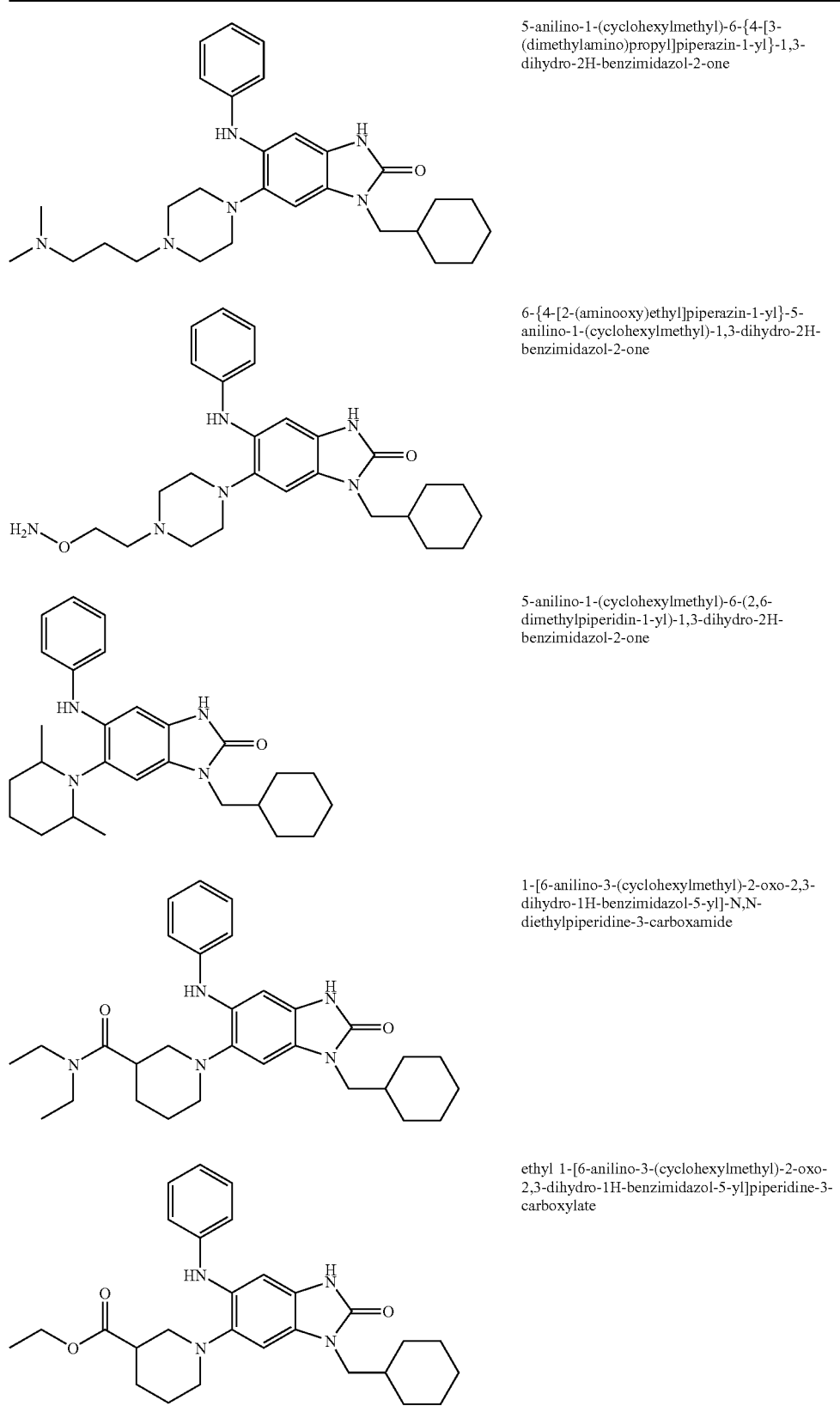

5-anilino-1-(cyclohexylmethyl)-6-{4-[3-(dimethylamino)propyl]piperazin-1-yl}-1,3-dihydro-2H-benzimidazol-2-one 6-{4-[2-(aminooxy)ethyl]piperazin-1-yl}-5-anilino-1-(cyclohexylmethyl)-1,3-dihydro-2H-benzimidazol-2-one 5-anilino-1-(cyclohexylmethyl)-6-(2,6-dimethylpiperidin-1-yl)-1,3-dihydro-2H-benzimidazol-2-one 1-[6-anilino-3-(cyclohexylmethyl)-2-oxo-2,3-dihydro-1H-benzimidazol-5-yl]-N,N-diethylpiperidine-3-carboxamide ethyl 1-[6-anilino-3-(cyclohexylmethyl)-2-oxo-2,3-dihydro-1H-benzimidazol-5-yl]piperidine-3-carboxylate TABLE II-continued
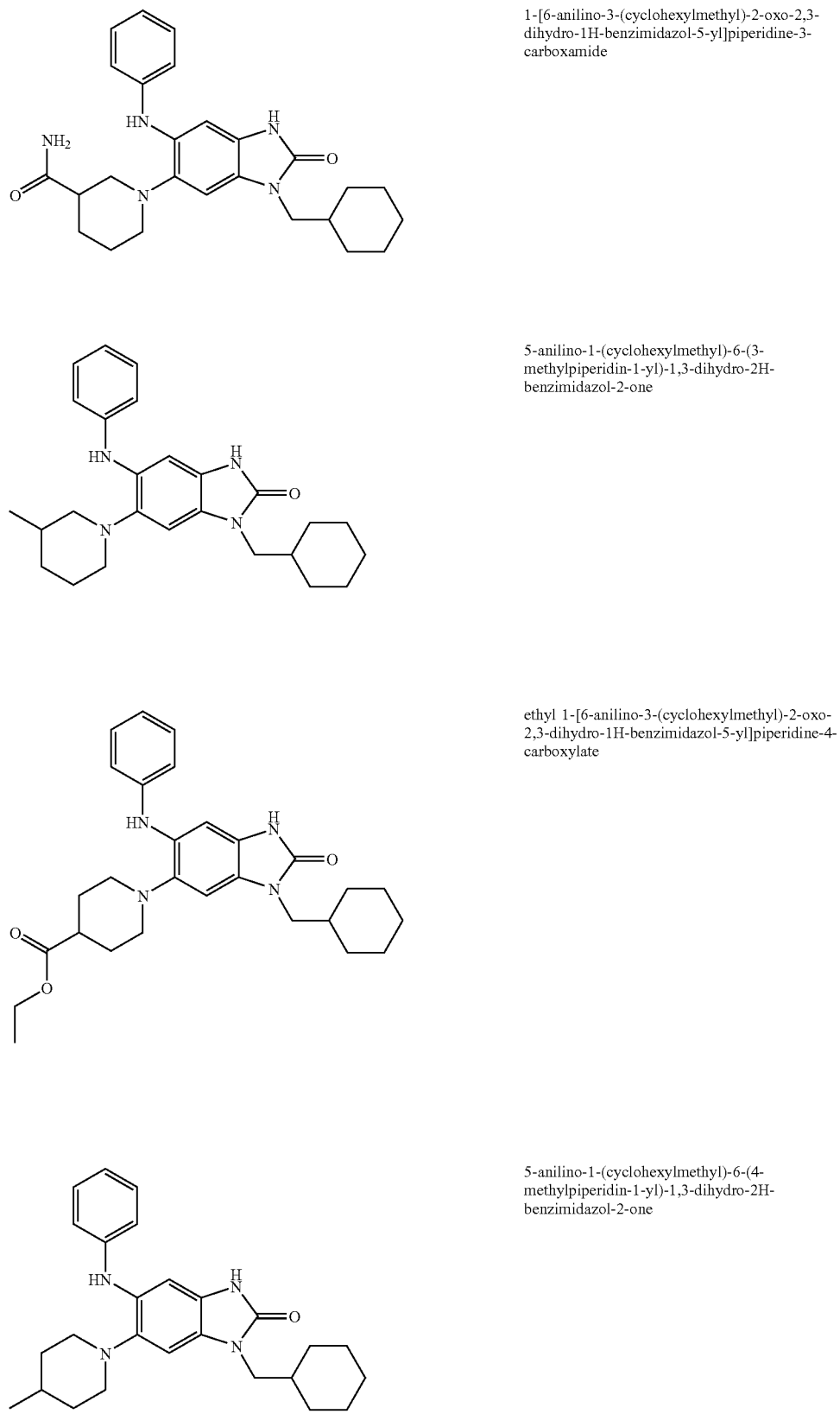
1-[6-anilino-3-(cyclohexylmethyl)-2-oxo-2,3-dihydro-1H-benzimidazol-5-yl]piperidine-3-carboxamide
5-anilino-1-(cyclohexylmethyl)-6-(3-methylpiperidin-1-yl)-1,3-dihydro-2H-benzimidazol-2-one
ethyl 1-[6-anilino-3-(cyclohexylmethyl)-2-oxo-2,3-dihydro-1H-benzimidazol-5-yl]piperidine-4-carboxylate
5-anilino-1-(cyclohexylmethyl)-6-(4-methylpiperidin-1-yl)-1,3-dihydro-2H-benzimidazol-2-one TABLE II-continued

| Structure | Name |
|---|---|
| 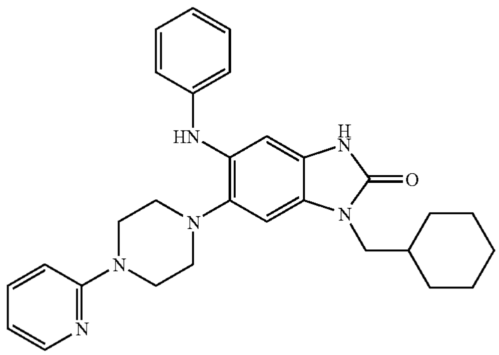 | 5-anilino-1-(cyclohexylmethyl)-6-(4-pyridin-2-ylpiperazin-1-yl)-1,3-dihydro-2H-benzimidazol-2-one |
| 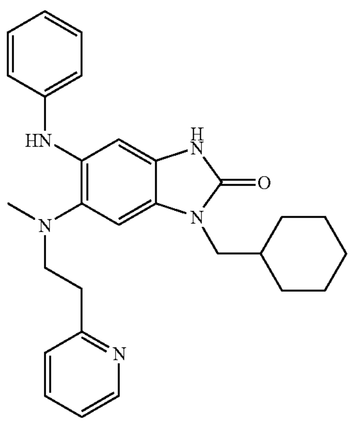 | 5-anilino-1-(cyclohexylmethyl)-6-[methyl(2-pyridin-2-ylethyl)amino]-1,3-dihydro-2H-benzimidazol-2-one |
| 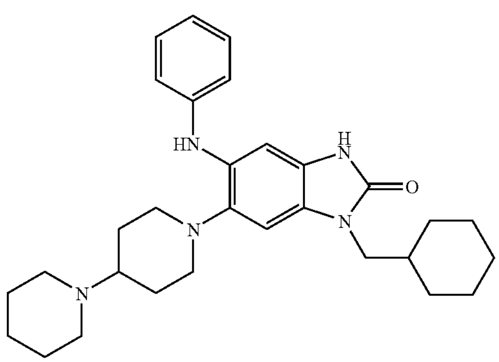 | 5-anilino-6-(1,4'-bipiperidin-1'-yl)-1-(cyclohexylmethyl)-1,3-dihydro-2H-benzimidazol-2-one |
| 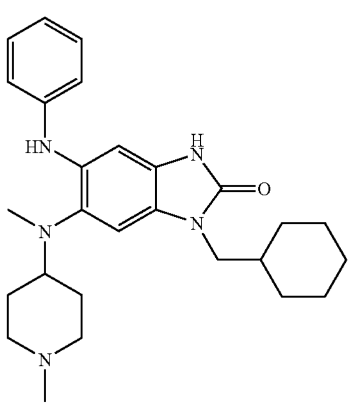 | 5-anilino-1-(cyclohexylmethyl)-6-[methyl(1-methylpiperidin-4-yl)amino]-1,3-dihydro-2H-benzimidazol-2-one |

TABLE II-continued
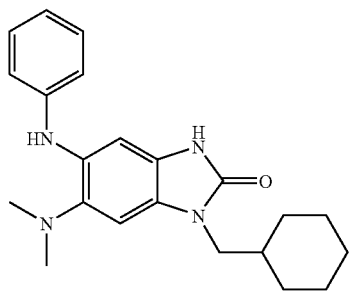
5-anilino-1-(cyclohexylmethyl)-6-(dimethylamino)-1,3-dihydro-2H-benzimidazol-2-one
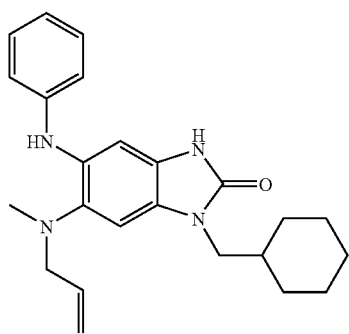
6-[allyl(methyl)amino]-5-anilino-1-(cyclohexylmethyl)-1,3-dihydro-2H-benzimidazol-2-one
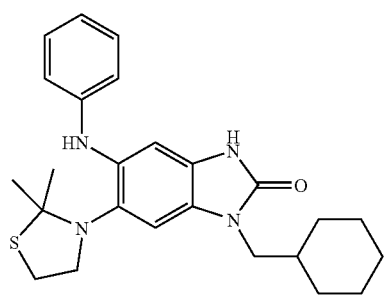
5-anilino-1-(cyclohexylmethyl)-6-(2,2-dimethyl-1,3-thiazolidin-3-yl)-1,3-dihydro-2H-benzimidazol-2-one
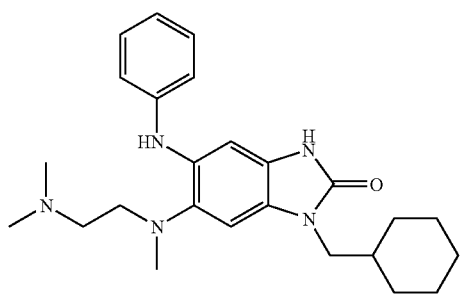
5-anilino-1-(cyclohexylmethyl)-6-[[2-(dimethylamino)ethyl](methyl)amino]-1,3-dihydro-2H-benzimidazol-2-one TABLE II-continued

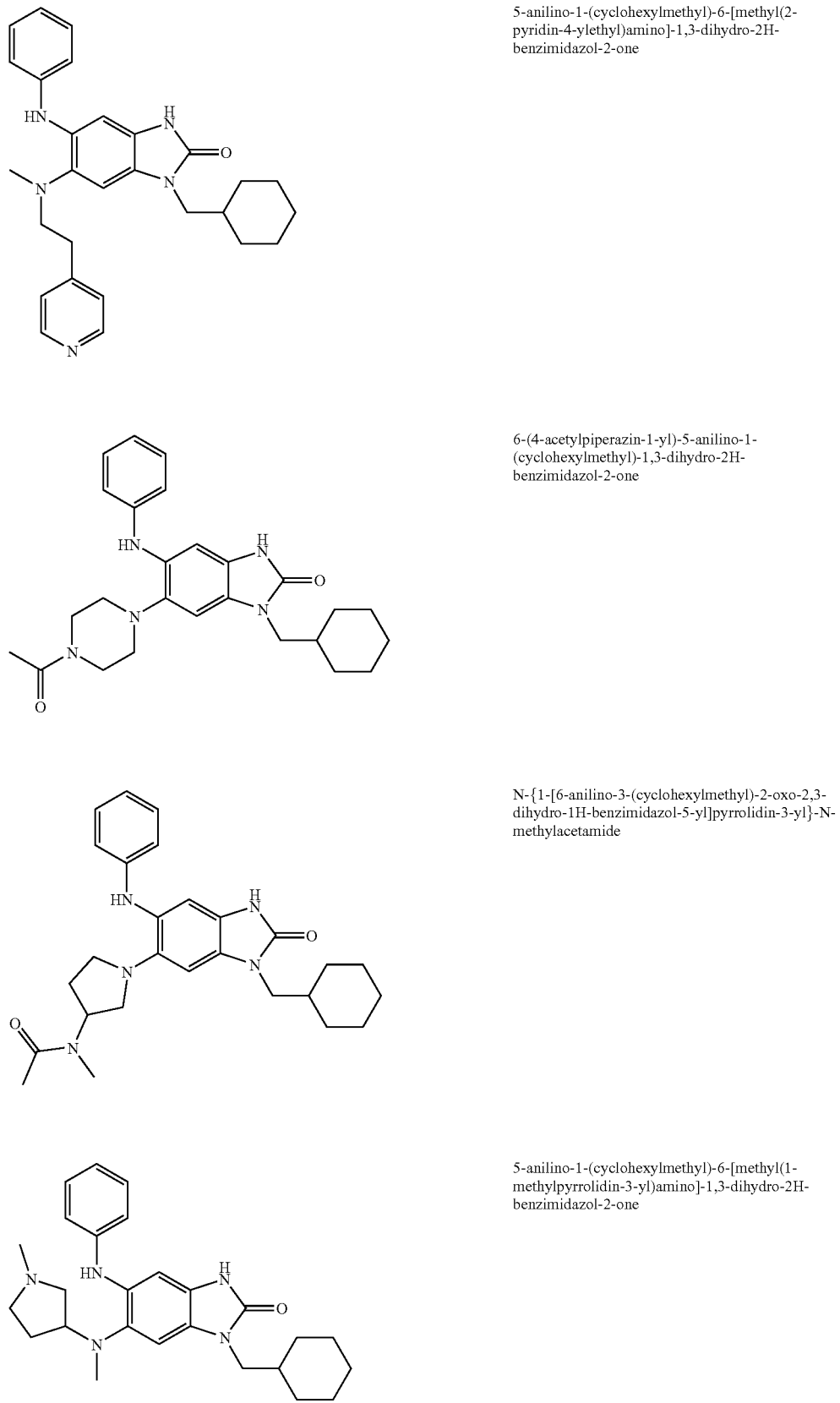

5-anilino-1-(cyclohexylmethyl)-6-[methyl(2-pyridin-4-ylethyl)amino]-1,3-dihydro-2H-benzimidazol-2-one 6-(4-acetylpiperazin-1-yl)-5-anilino-1-(cyclohexylmethyl)-1,3-dihydro-2H-benzimidazol-2-one N-{1-[6-anilino-3-(cyclohexylmethyl)-2-oxo-2,3-dihydro-1H-benzimidazol-5-yl]pyrrolidin-3-yl}-N-methylacetamide 5-anilino-1-(cyclohexylmethyl)-6-[methyl(1-methylpyrrolidin-3-yl)amino]-1,3-dihydro-2H-benzimidazol-2-one TABLE II-continued

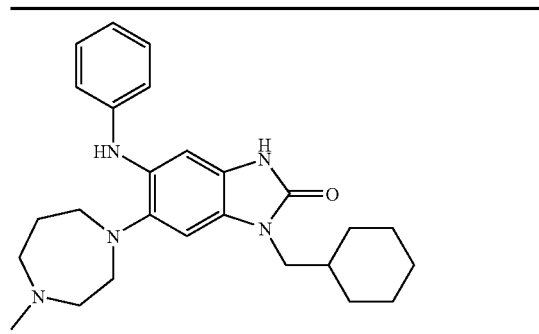

5-anilino-1-(cyclohexylmethyl)-6-(4-methyl-1,4-diazepan-1-yl)-1,3-dihydro-2H-benzimidazol-2-one

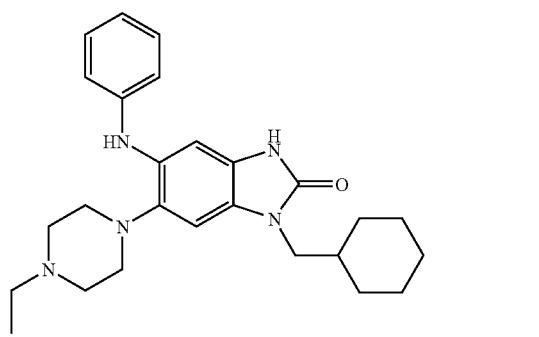

5-anilino-1-(cyclohexylmethyl)-6-(4-ethylpiperazin-1-yl)-1,3-dihydro-2H-benzimidazol-2-one

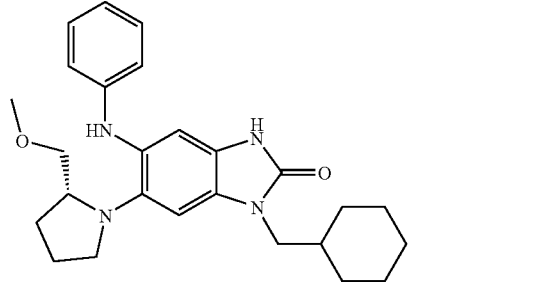

5-anilino-1-(cyclohexylmethyl)-6-[(2R)-2-(methoxymethyl)pyrrolidin-1-yl]-1,3-dihydro-2H-benzimidazol-2-one

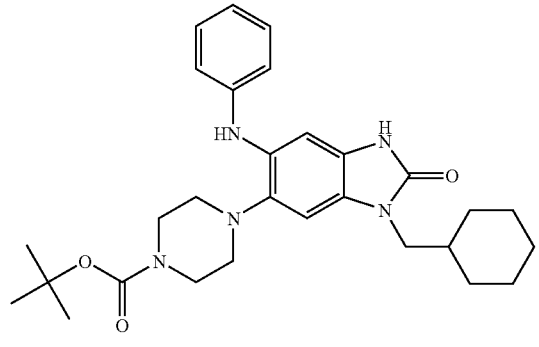

tert-butyl 4-[6-anilino-3-(cyclohexylmethyl)-2-oxo-2,3-dihydro-1H-benzimidazol-5-yl]piperazine-1-carboxylate

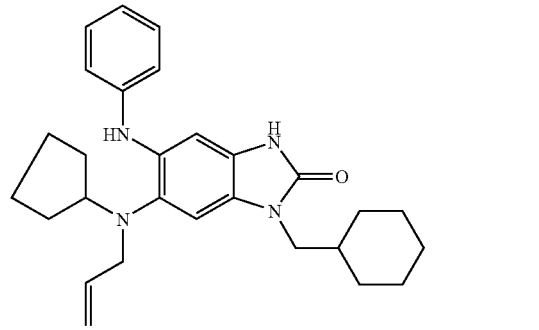

6-[allyl(cyclopentyl)amino]-5-anilino-1-(cyclohexylmethyl)-1,3-dihydro-2H-benzimidazol-2-one TABLE II-continued

| | |
|---|---|
| (structure) | methyl 1-[6-anilino-3-(cyclohexylmethyl)-2-oxo-2,3-dihydro-1H-benzimidazol-5-yl]piperidine-4-carboxylate |
| (structure) | 5-anilino-1-(cyclohexylmethyl)-6-[(3R)-3-(dimethylamino)pyrrolidin-1-yl]-1,3-dihydro-2H-benzimidazol-2-one |
| (structure) | 5-anilino-1-(cyclohexylmethyl)-6-[(3S)-3-(dimethylamino)pyrrolidin-1-yl]-1,3-dihydro-2H-benzimidazol-2-one |
| (structure) | 1-[6-anilino-3-(cyclohexylmethyl)-2-oxo-2,3-dihydro-1H-benzimidazol-5-yl]-D-prolinamide |
| (structure) | 5-anilino-1-(cyclohexylmethyl)-6-[4-(3,5-dichloropyridin-4-yl)piperazin-1-yl]-1,3-dihydro-2H-benzimidazol-2-one |

TABLE II-continued
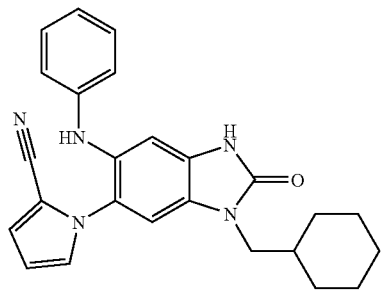
1-[6-anilino-3-(cyclohexylmethyl)-2-oxo-2,3-dihydro-1H-benzimidazol-5-yl]-1H-pyrrole-2-carbonitrile
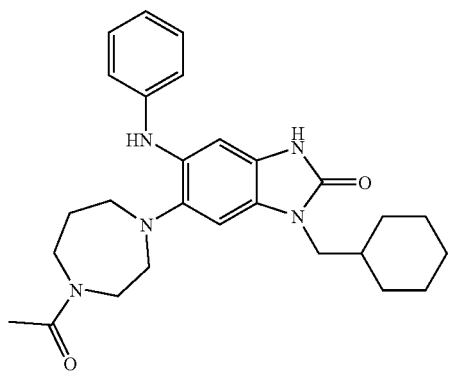
6-(4-acetyl-1,4-diazepan-1-yl)-5-anilino-1-(cyclohexylmethyl)-1,3-dihydro-2H-benzimidazol-2-one
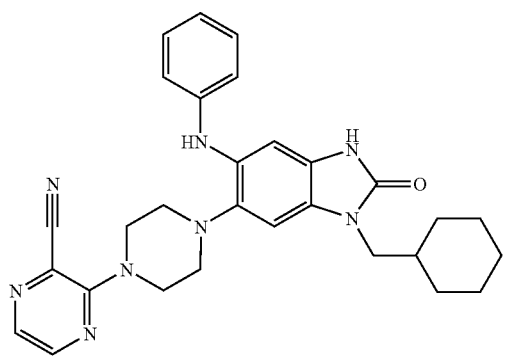
3-{4-[6-anilino-3-(cyclohexylmethyl)-2-oxo-2,3-dihydro-1H-benzimidazol-5-yl]piperazin-1-yl}pyrazine-2-carbonitrile
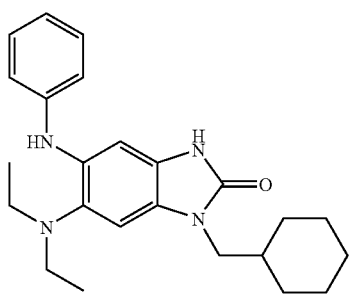
5-anilino-1-(cyclohexylmethyl)-6-(diethylamino)-1,3-dihydro-2H-benzimidazol-2-one TABLE II-continued

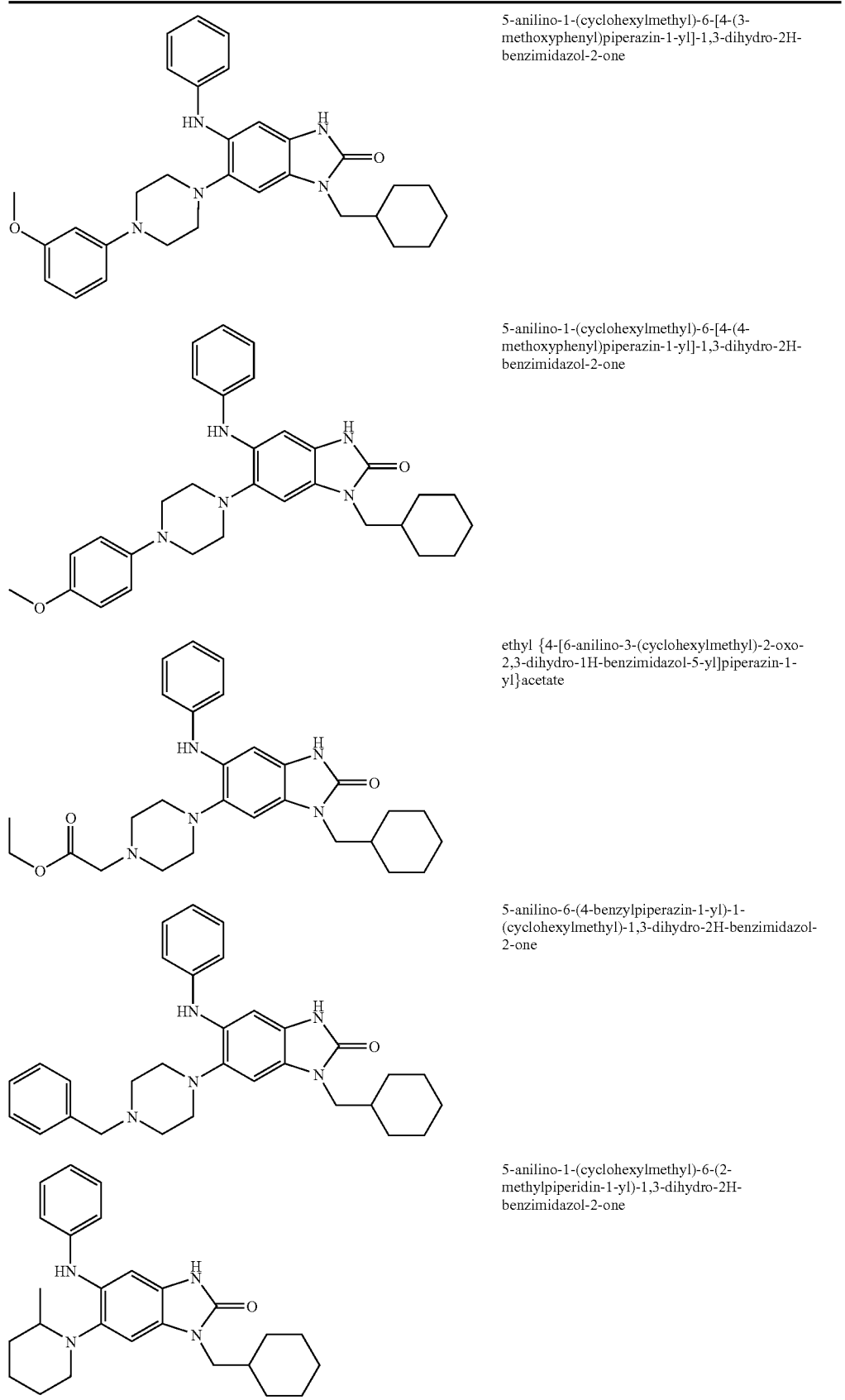

5-anilino-1-(cyclohexylmethyl)-6-[4-(3-methoxyphenyl)piperazin-1-yl]-1,3-dihydro-2H-benzimidazol-2-one 5-anilino-1-(cyclohexylmethyl)-6-[4-(4-methoxyphenyl)piperazin-1-yl]-1,3-dihydro-2H-benzimidazol-2-one ethyl {4-[6-anilino-3-(cyclohexylmethyl)-2-oxo-2,3-dihydro-1H-benzimidazol-5-yl]piperazin-1-yl}acetate 5-anilino-6-(4-benzylpiperazin-1-yl)-1-(cyclohexylmethyl)-1,3-dihydro-2H-benzimidazol-2-one 5-anilino-1-(cyclohexylmethyl)-6-(2-methylpiperidin-1-yl)-1,3-dihydro-2H-benzimidazol-2-one TABLE II-continued

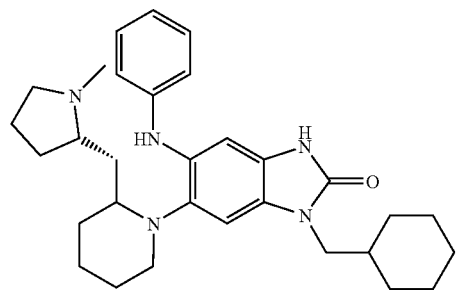

5-anilino-1-(cyclohexylmethyl)-6-(2-{[(2S)-1-methylpyrrolidin-2-yl]methyl}piperidin-1-yl)-1,3-dihydro-2H-benzimidazol-2-one

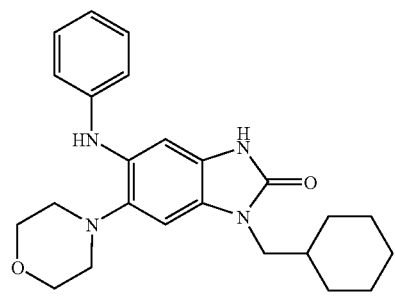

5-anilino-1-(cyclohexylmethyl)-6-morpholin-4-yl-1,3-dihydro-2H-benzimidazol-2-one

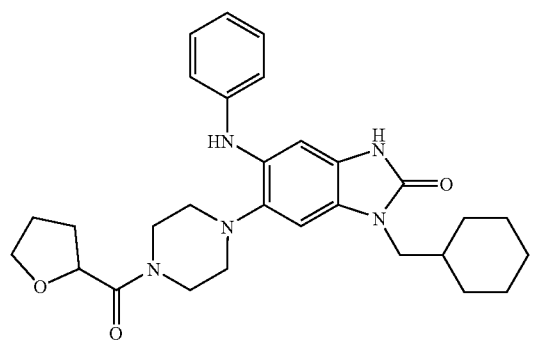

5-anilino-1-(cyclohexylmethyl)-6-[4-(tetrahydrofuran-2-ylcarbonyl)piperazin-1-yl]-1,3-dihydro-2H-benzimidazol-2-one

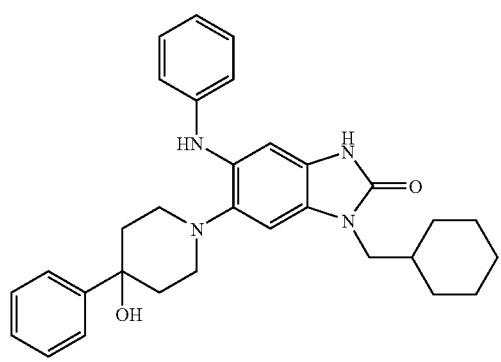

5-anilino-1-(cyclohexylmethyl)-6-(4-hydroxy-4-phenylpiperidin-1-yl)-1,3-dihydro-2H-benzimidazol-2-one TABLE II-continued
| | |
|---|---|
| 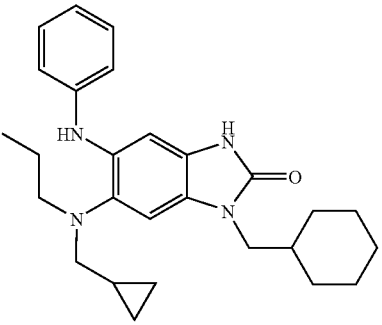 | 5-anilino-1-(cyclohexylmethyl)-6-[(cyclopropylmethyl)(propyl)amino]-1,3-dihydro-2H-benzimidazol-2-one |
| 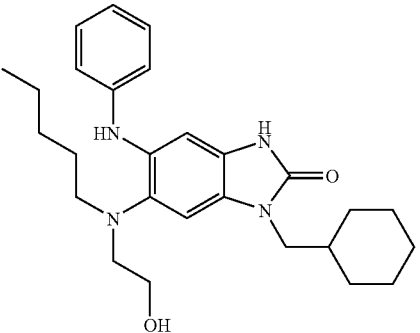 | 5-anilino-1-(cyclohexylmethyl)-6-[(2-hydroxyethyl)(pentyl)amino]-1,3-dihydro-2H-benzimidazol-2-one |
| 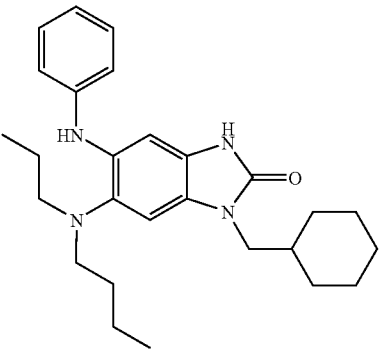 | 5-anilino-6-[butyl(propyl)amino]-1-(cyclohexylmethyl)-1,3-dihydro-2H-benzimidazol-2-one |
| 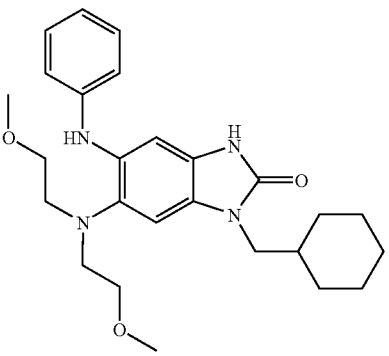 | 5-anilino-6-[bis(2-methoxyethyl)amino]-1-(cyclohexylmethyl)-1,3-dihydro-2H-benzimidazol-2-one |

TABLE II-continued

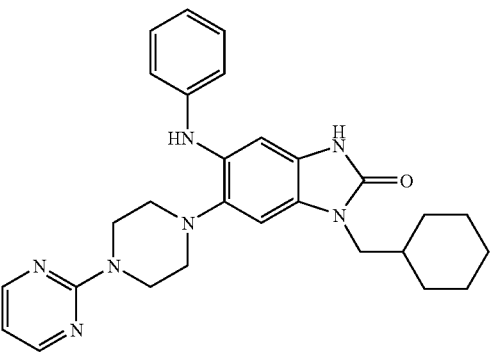

5-anilino-1-(cyclohexylmethyl)-6-(4-pyrimidin-2-ylpiperazin-1-yl)-1,3-dihydro-2H-benzimidazol-2-one

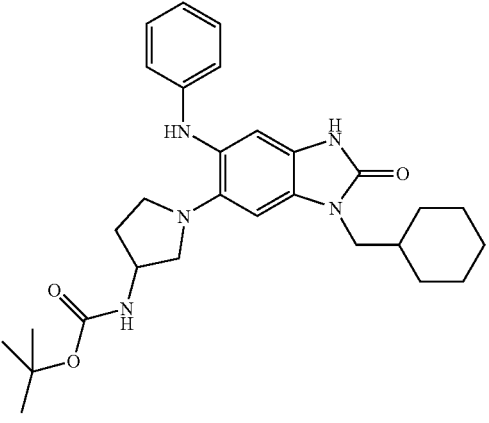

tert-butyl 1-[6-anilino-3-(cyclohexylmethyl)-2-oxo-2,3-dihydro-1H-benzimidazol-5-yl]pyrrolidin-3-ylcarbamate

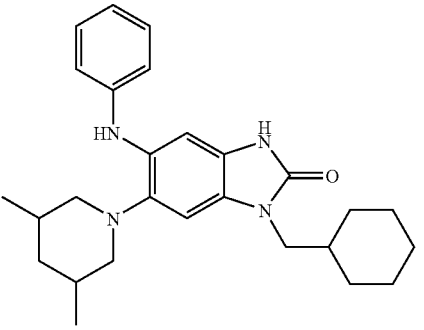

5-anilino-1-(cyclohexylmethyl)-6-(3,5-dimethylpiperidin-1-yl)-1,3-dihydro-2H-benzimidazol-2-one

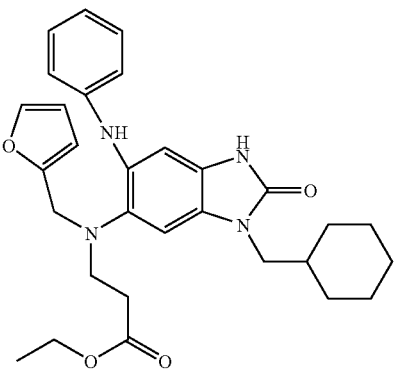

ethyl N-[6-anilino-3-(cyclohexylmethyl)-2-oxo-2,3-dihydro-1H-benzimidazol-5-yl]-N-(2-furylmethyl)-beta-alaninate TABLE II-continued
| | |
|---|---|
| 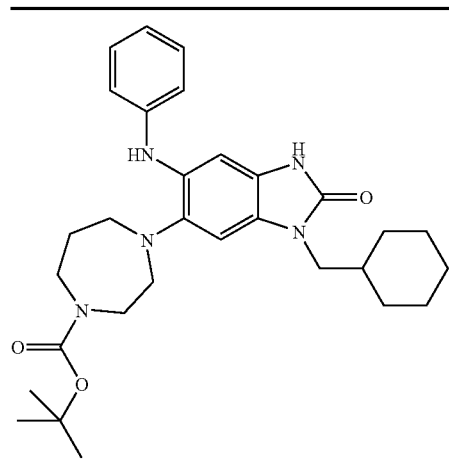 | tert-butyl 4-[6-anilino-3-(cyclohexylmethyl)-2-oxo-2,3-dihydro-1H-benzimidazol-5-yl]-1,4-diazepane-1-carboxylate |
| 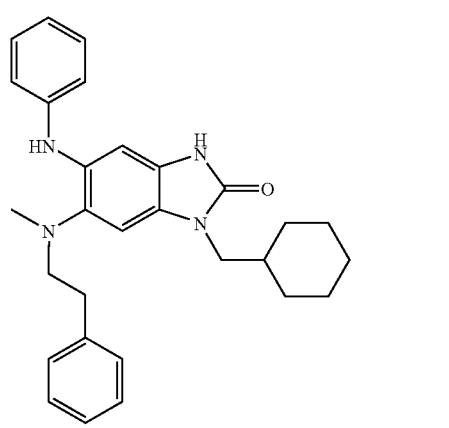 | 5-anilino-1-(cyclohexylmethyl)-6-[methyl(2-phenylethyl)amino]-1,3-dihydro-2H-benzimidazol-2-one |
| 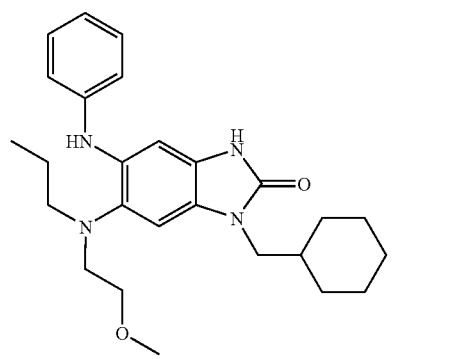 | 5-anilino-1-(cyclohexylmethyl)-6-[(2-methoxyethyl)(propyl)amino]-1,3-dihydro-2H-benzimidazol-2-one |
| 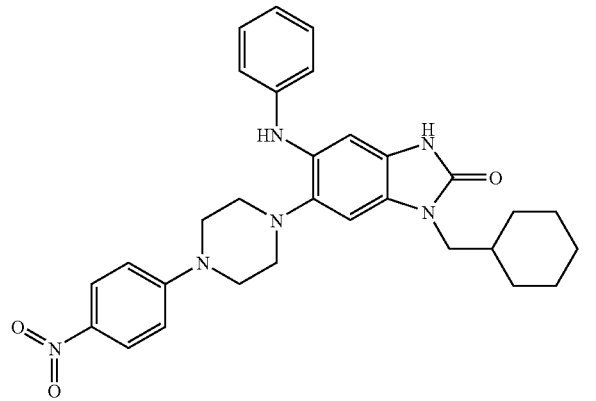 | 5-anilino-1-(cyclohexylmethyl)-6-[4-(4-nitrophenyl)piperazin-1-yl]-1,3-dihydro-2H-benzimidazol-2-one |

TABLE II-continued
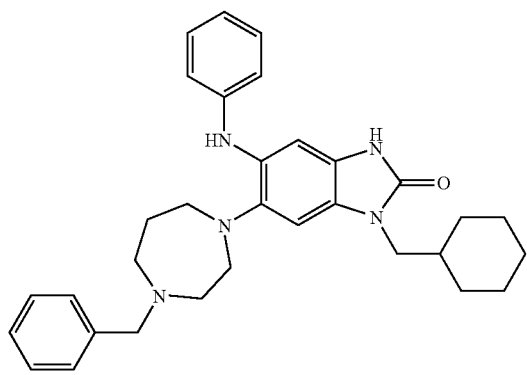
5-anilino-6-(4-benzyl-1,4-diazepan-1-yl)-1-(cyclohexylmethyl)-1,3-dihydro-2H-benzimidazol-2-one
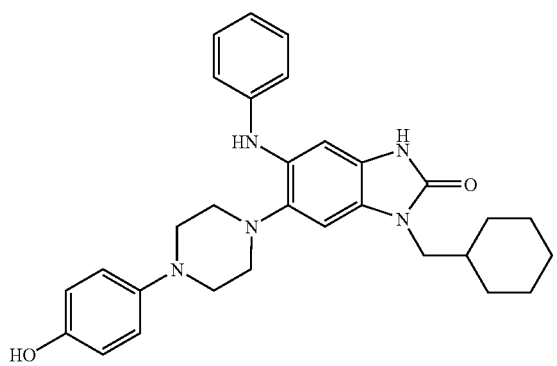
5-anilino-1-(cyclohexylmethyl)-6-[4-(4-hydroxyphenyl)piperazin-1-yl]-1,3-dihydro-2H-benzimidazol-2-one
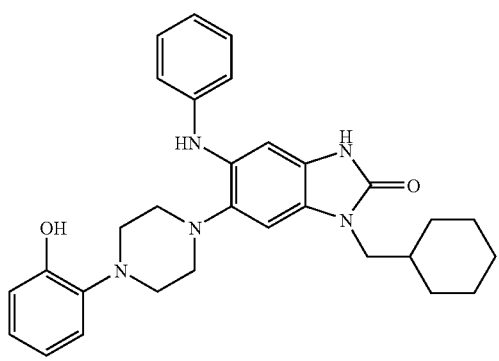
5-anilino-1-(cyclohexylmethyl)-6-[4-(2-hydroxyphenyl)piperazin-1-yl]-1,3-dihydro-2H-benzimidazol-2-one
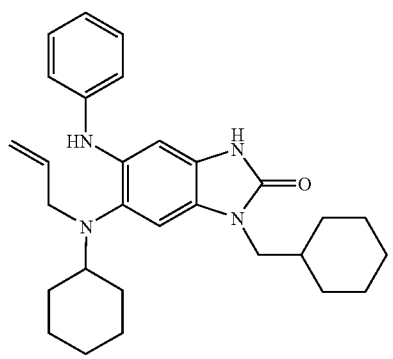
6-[allyl(cyclohexyl)amino]-5-anilino-1-(cyclohexylmethyl)-1,3-dihydro-2H-benzimidazol-2-one TABLE II-continued

| | |
|---|---|
| 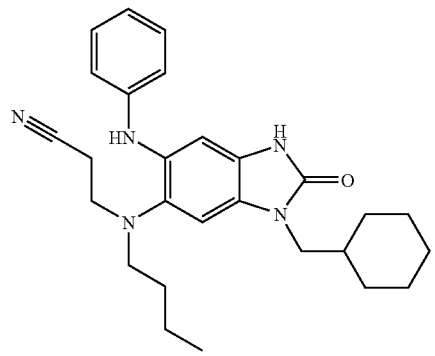 | 3-[[6-anilino-3-(cyclohexylmethyl)-2-oxo-2,3-dihydro-1H-benzimidazol-5-yl](butyl)amino]propanenitrile |
| 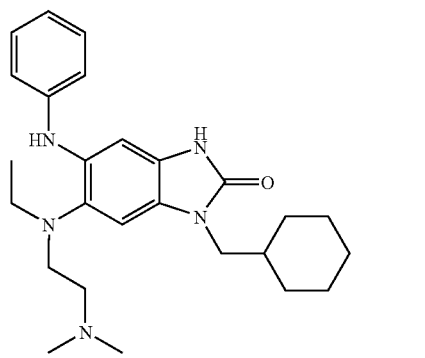 | 5-anilino-1-(cyclohexylmethyl)-6-[[2-(dimethylamino)ethyl](ethyl)amino]-1,3-dihydro-2H-benzimidazol-2-one |
| 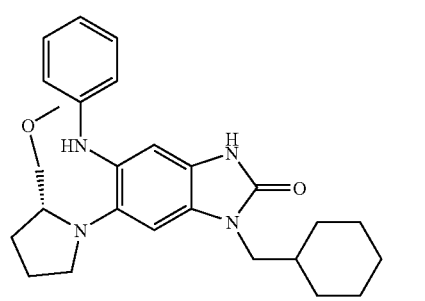 | 1-Cyclohexylmethyl-6-((R)-2-methoxymethyl-pyrrolidin-1-yl)-5-phenylamino-1,3-dihydro-benzoimidazol-2-one |
| 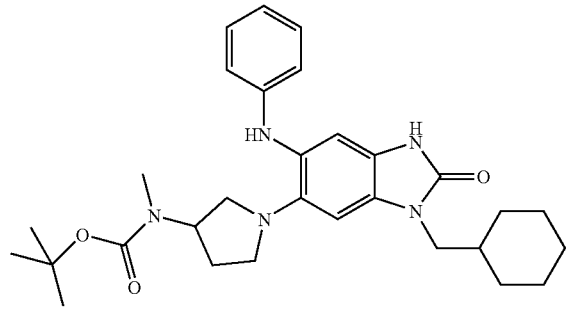 | tert-butyl 1-[6-anilino-3-(cyclohexylmethyl)-2-oxo-2,3-dihydro-1H-benzimidazol-5-yl]pyrrolidin-3-yl(methyl)carbamate |

TABLE II-continued

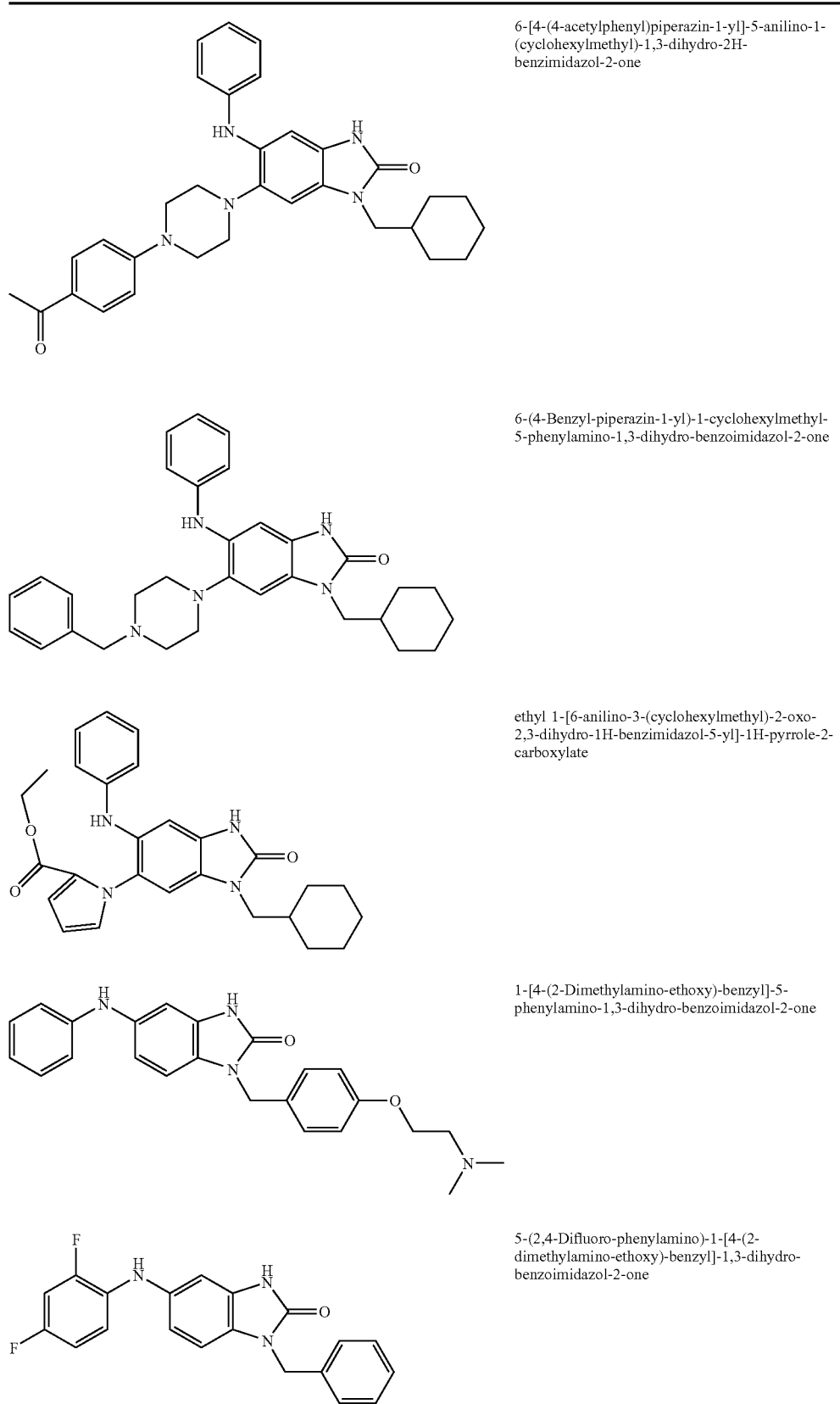

6-[4-(4-acetylphenyl)piperazin-1-yl]-5-anilino-1-(cyclohexylmethyl)-1,3-dihydro-2H-benzimidazol-2-one 6-(4-Benzyl-piperazin-1-yl)-1-cyclohexylmethyl-5-phenylamino-1,3-dihydro-benzoimidazol-2-one ethyl 1-[6-anilino-3-(cyclohexylmethyl)-2-oxo-2,3-dihydro-1H-benzimidazol-5-yl]-1H-pyrrole-2-carboxylate 1-[4-(2-Dimethylamino-ethoxy)-benzyl]-5-phenylamino-1,3-dihydro-benzoimidazol-2-one 5-(2,4-Difluoro-phenylamino)-1-[4-(2-dimethylamino-ethoxy)-benzyl]-1,3-dihydro-benzoimidazol-2-one TABLE II-continued

| | |
|---|---|
| 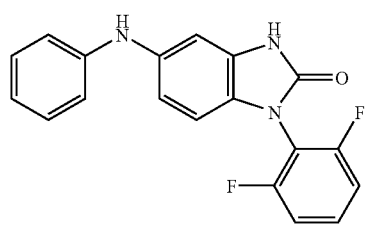 | 1-(2,6-Difluoro-phenyl)-5-phenylamino-1,3-dihydro-benzoimidazol-2-one |
| 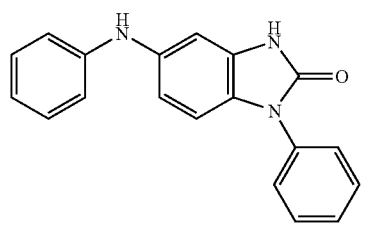 | 1-Phenyl-5-phenylamino-1,3-dihydro-benzoimidazol-2-one |
| 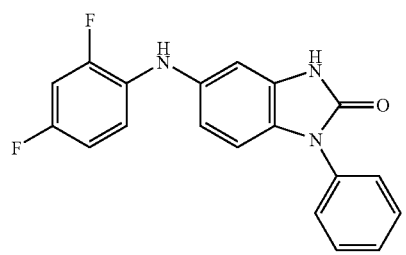 | 5-(2,4-Difluoro-phenylamino)-1-phenyl-1,3-dihydro-benzoimidazol-2-one |
| 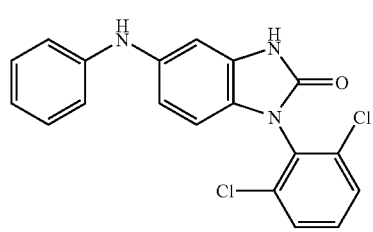 | 1-(2,6-Dichloro-phenyl)-5-phenylamino-1,3-dihydro-benzoimidazol-2-one |
| 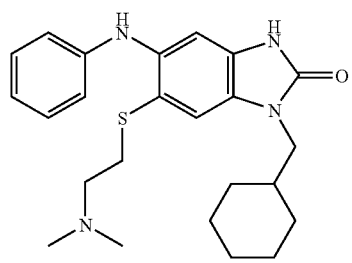 | 1-Cyclohexylmethyl-6-(2-dimethylamino-ethylsulfanyl)-5-phenylamino-1,3-dihydro-benzoimidazol-2-one |
| 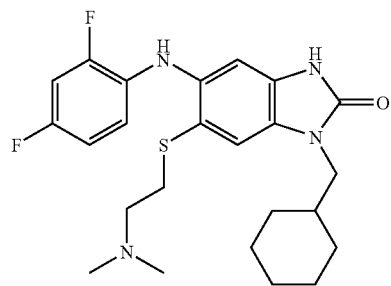 | 1-Cyclohexylmethyl-5-(2,4-difluoro-phenylamino)-6-(2-dimethylamino-ethylsulfanyl)-1,3-dihydro-benzoimidazol-2-one |

TABLE II-continued

| Structure | Name |
|---|---|
| 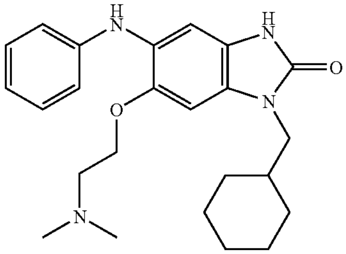 | 1-Cyclohexylmethyl-6-(2-dimethylamino-ethoxy)-5-phenylamino-1,3-dihydro-benzoimidazol-2-one |
| 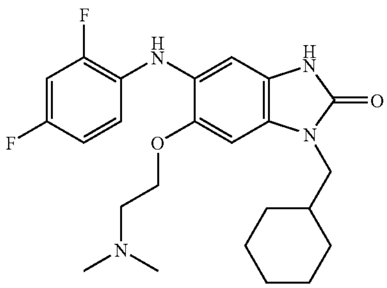 | 1-Cyclohexylmethyl-5-(2,4-difluoro-phenylamino)-6-(2-dimethylamino-ethoxy)-1,3-dihydro-benzoimidazol-2-one |
| 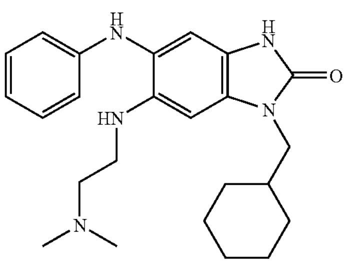 | 1-Cyclohexylmethyl-6-(2-dimethylamino-ethylamino)-5-phenylamino-1,3-dihydro-benzoimidazol-2-one and |
| | 1-Cyclohexylmethyl-5-(2,4-difluoro-phenylamino)-6-(2-dimethylamino-ethylamino)-1,3-dihydro-benzoimidazol-2-one | or the pharmaceutically acceptable acids and salts or isomers thereof.

The following are preferred compounds of the invention:

TABLE III

| Structure | Name |
|---|---|
| 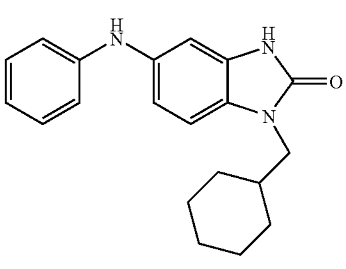 | 1-Cyclohexylmethyl-5-phenylamino-1,3-dihydro-benzoimidazol-2-one; |

TABLE III-continued
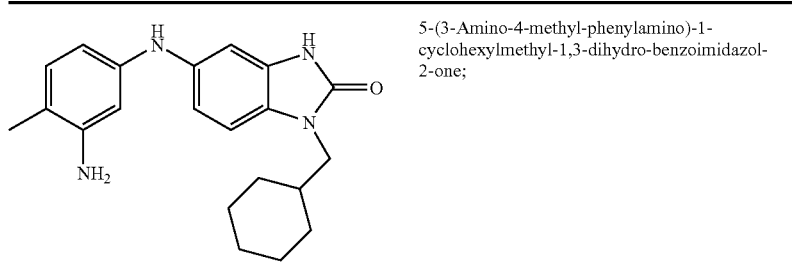
5-(3-Amino-4-methyl-phenylamino)-1-cyclohexylmethyl-1,3-dihydro-benzoimidazol-2-one;
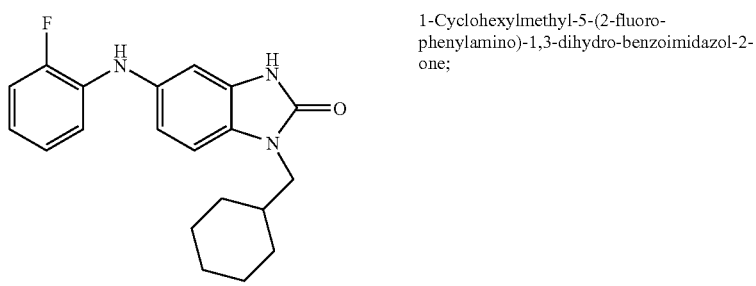
1-Cyclohexylmethyl-5-(2-fluoro-phenylamino)-1,3-dihydro-benzoimidazol-2-one;
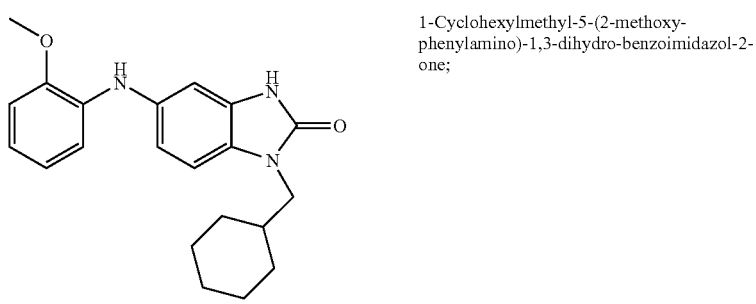
1-Cyclohexylmethyl-5-(2-methoxy-phenylamino)-1,3-dihydro-benzoimidazol-2-one;
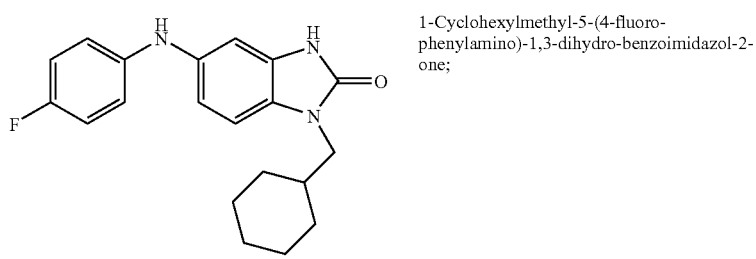
1-Cyclohexylmethyl-5-(4-fluoro-phenylamino)-1,3-dihydro-benzoimidazol-2-one;
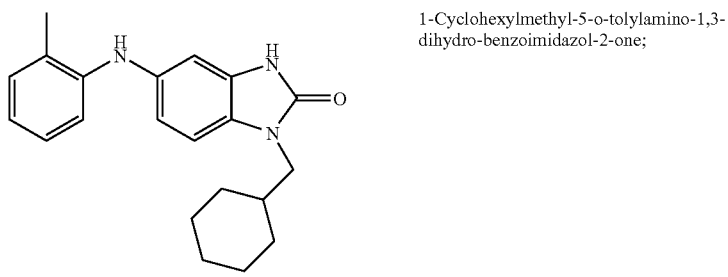
1-Cyclohexylmethyl-5-o-tolylamino-1,3-dihydro-benzoimidazol-2-one;

TABLE III-continued
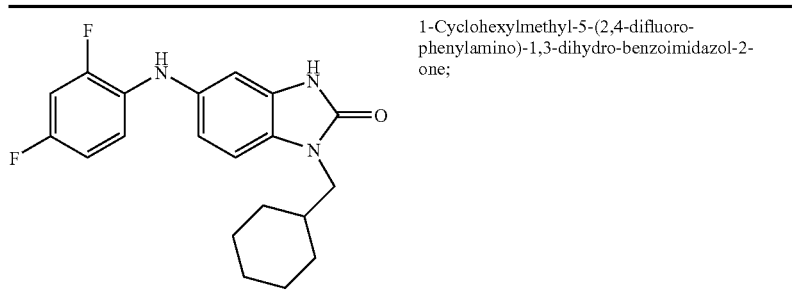
1-Cyclohexylmethyl-5-(2,4-difluoro-phenylamino)-1,3-dihydro-benzoimidazol-2-one;
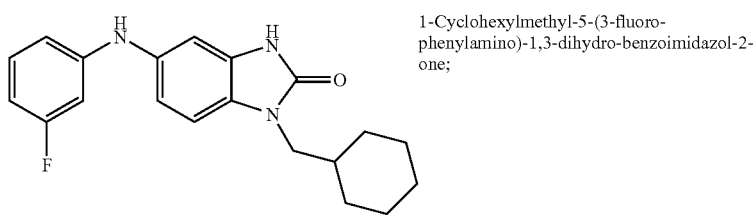
1-Cyclohexylmethyl-5-(3-fluoro-phenylamino)-1,3-dihydro-benzoimidazol-2-one;
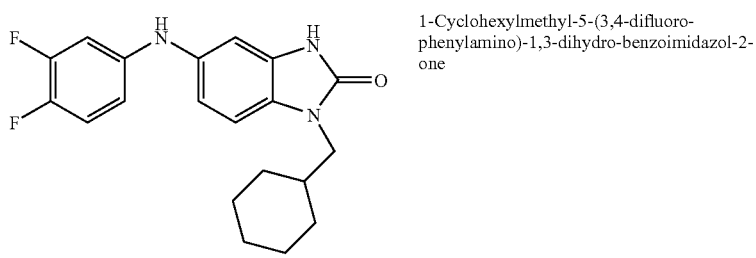
1-Cyclohexylmethyl-5-(3,4-difluoro-phenylamino)-1,3-dihydro-benzoimidazol-2-one
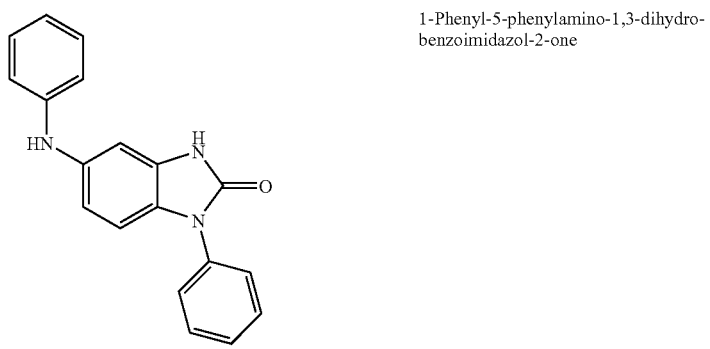
1-Phenyl-5-phenylamino-1,3-dihydro-benzoimidazol-2-one
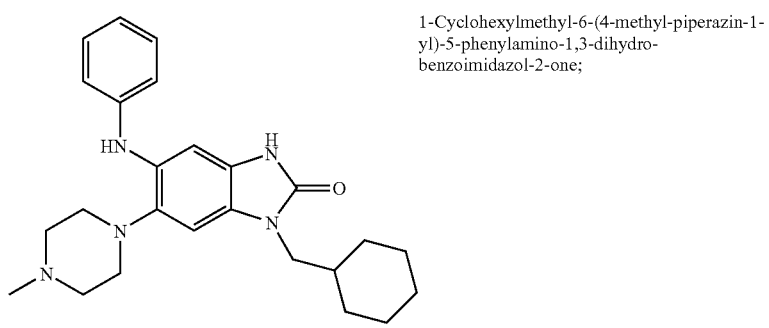
1-Cyclohexylmethyl-6-(4-methyl-piperazin-1-yl)-5-phenylamino-1,3-dihydro-benzoimidazol-2-one;

TABLE III-continued
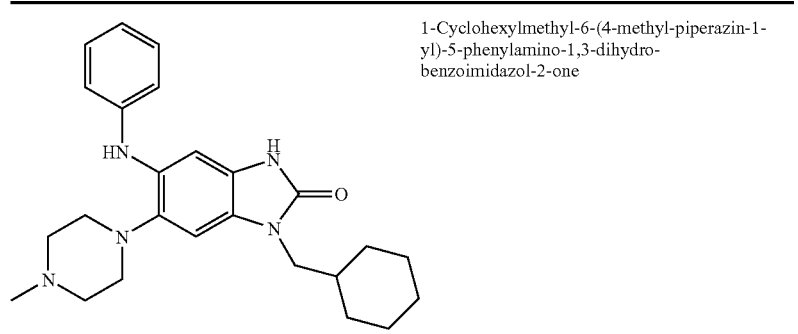
1-Cyclohexylmethyl-6-(4-methyl-piperazin-1-yl)-5-phenylamino-1,3-dihydro-benzoimidazol-2-one
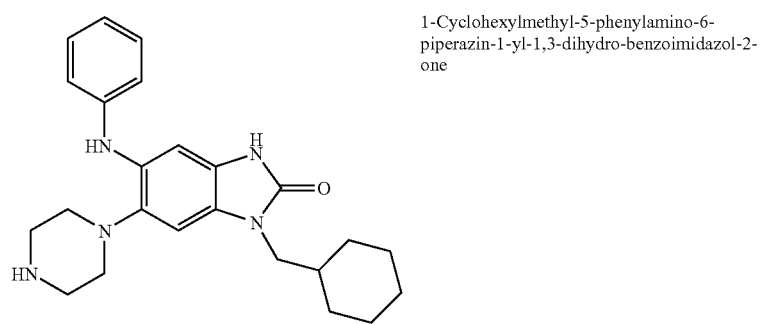
1-Cyclohexylmethyl-5-phenylamino-6-piperazin-1-yl-1,3-dihydro-benzoimidazol-2-one
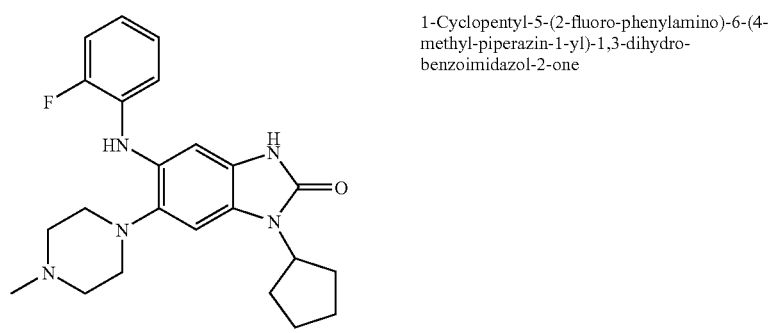
1-Cyclopentyl-5-(2-fluoro-phenylamino)-6-(4-methyl-piperazin-1-yl)-1,3-dihydro-benzoimidazol-2-one
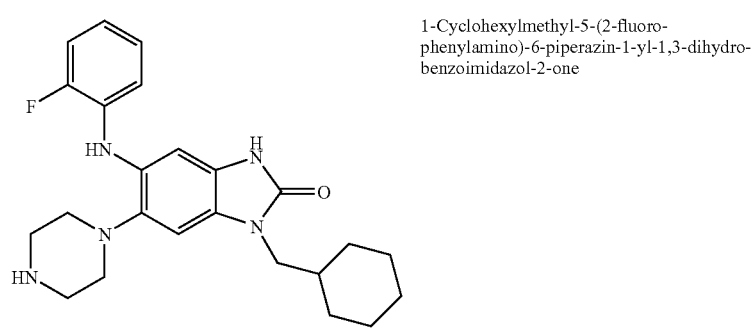
1-Cyclohexylmethyl-5-(2-fluoro-phenylamino)-6-piperazin-1-yl-1,3-dihydro-benzoimidazol-2-one TABLE III-continued
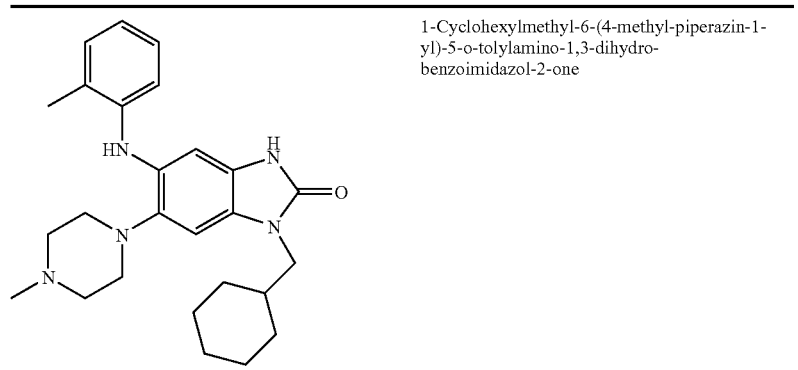
1-Cyclohexylmethyl-6-(4-methyl-piperazin-1-yl)-5-o-tolylamino-1,3-dihydro-benzoimidazol-2-one
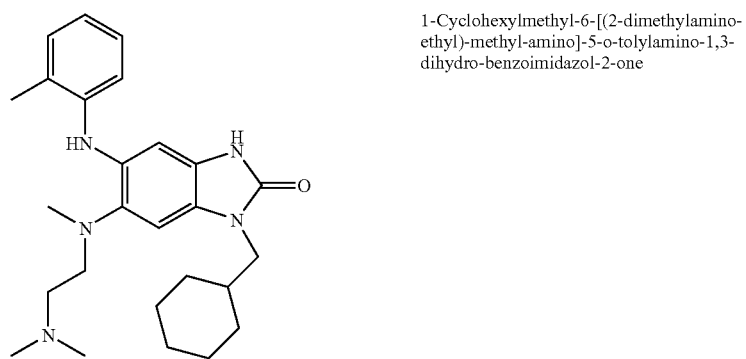
1-Cyclohexylmethyl-6-[(2-dimethylamino-ethyl)-methyl-amino]-5-o-tolylamino-1,3-dihydro-benzoimidazol-2-one
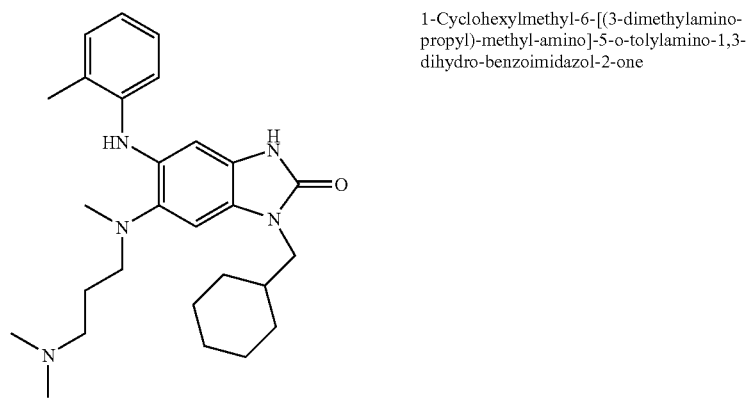
1-Cyclohexylmethyl-6-[(3-dimethylamino-propyl)-methyl-amino]-5-o-tolylamino-1,3-dihydro-benzoimidazol-2-one
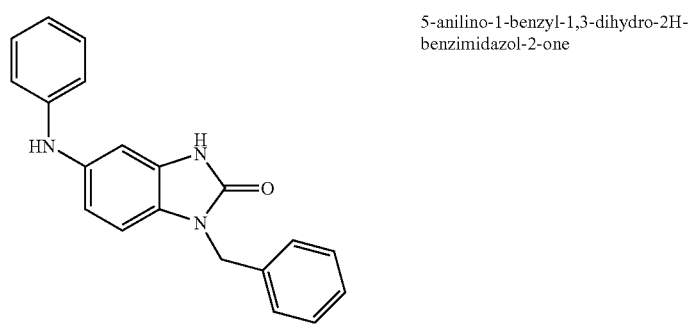
5-anilino-1-benzyl-1,3-dihydro-2H-benzimidazol-2-one TABLE III-continued
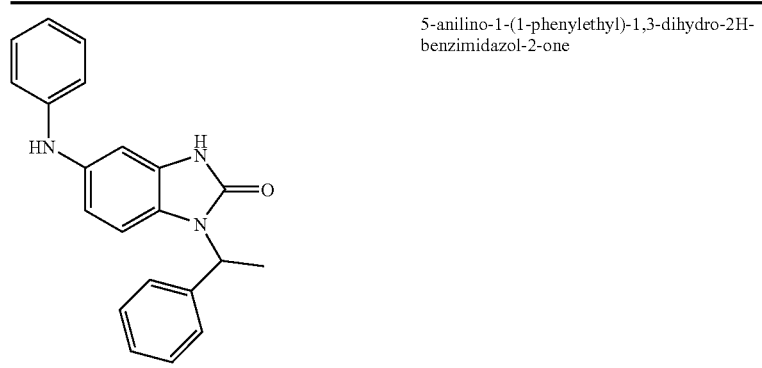
5-anilino-1-(1-phenylethyl)-1,3-dihydro-2H-benzimidazol-2-one
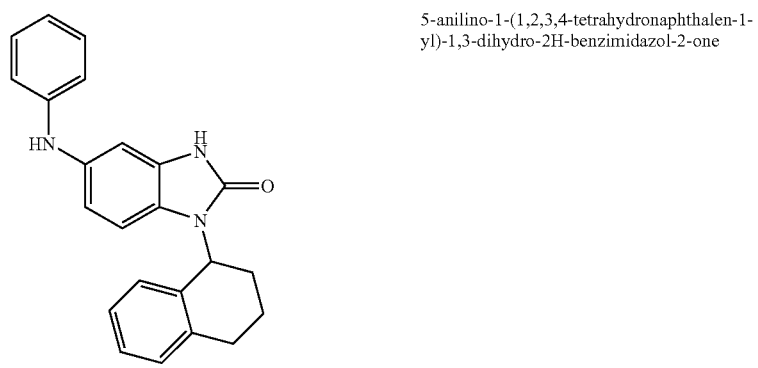
5-anilino-1-(1,2,3,4-tetrahydronaphthalen-1-yl)-1,3-dihydro-2H-benzimidazol-2-one
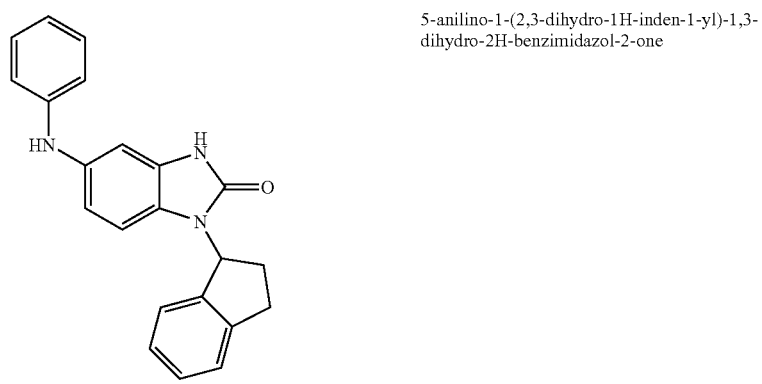
5-anilino-1-(2,3-dihydro-1H-inden-1-yl)-1,3-dihydro-2H-benzimidazol-2-one
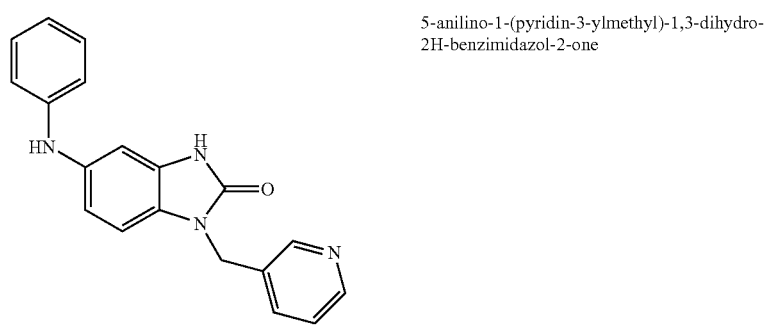
5-anilino-1-(pyridin-3-ylmethyl)-1,3-dihydro-2H-benzimidazol-2-one TABLE III-continued
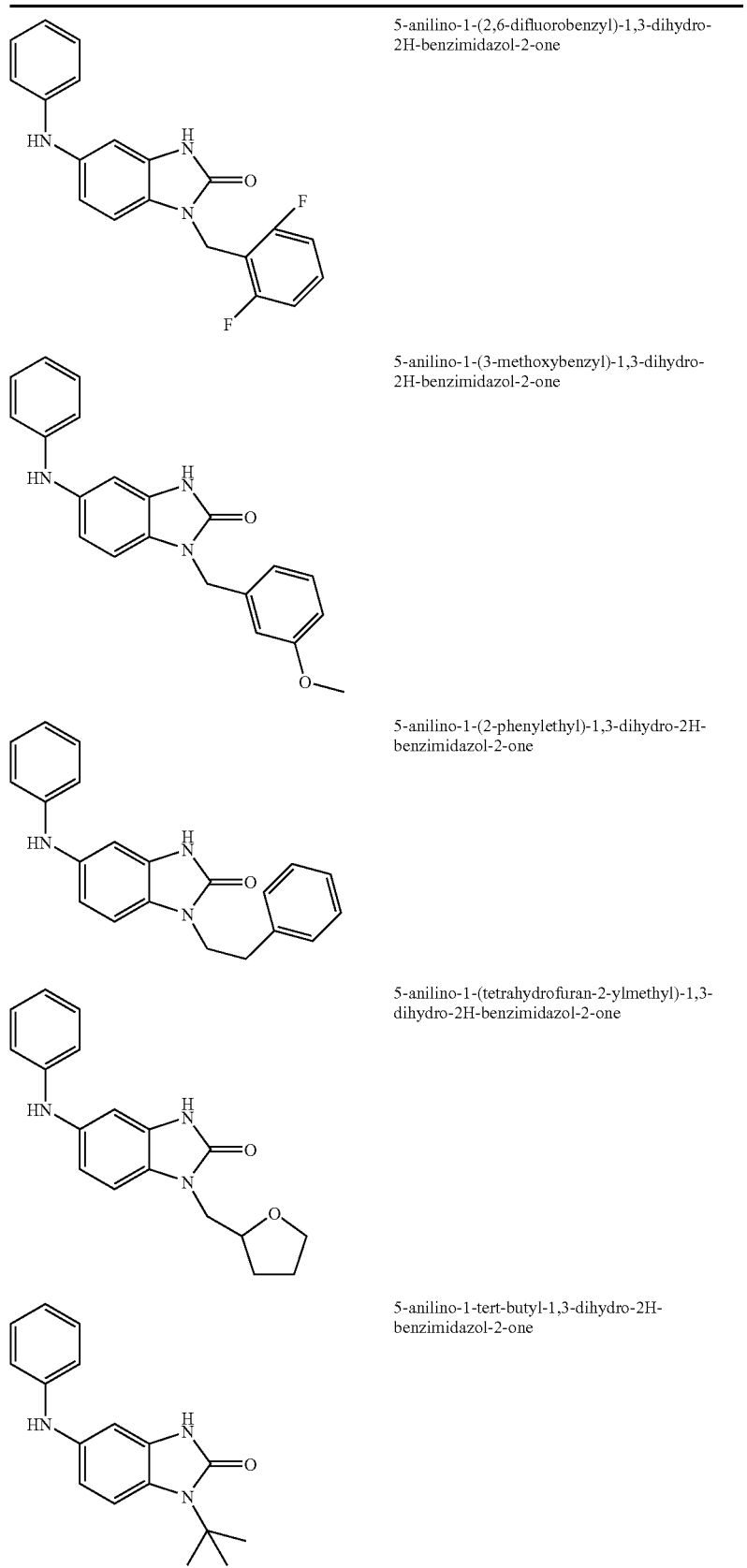
5-anilino-1-(2,6-difluorobenzyl)-1,3-dihydro-2H-benzimidazol-2-one
5-anilino-1-(3-methoxybenzyl)-1,3-dihydro-2H-benzimidazol-2-one
5-anilino-1-(2-phenylethyl)-1,3-dihydro-2H-benzimidazol-2-one
5-anilino-1-(tetrahydrofuran-2-ylmethyl)-1,3-dihydro-2H-benzimidazol-2-one
5-anilino-1-tert-butyl-1,3-dihydro-2H-benzimidazol-2-one TABLE III-continued
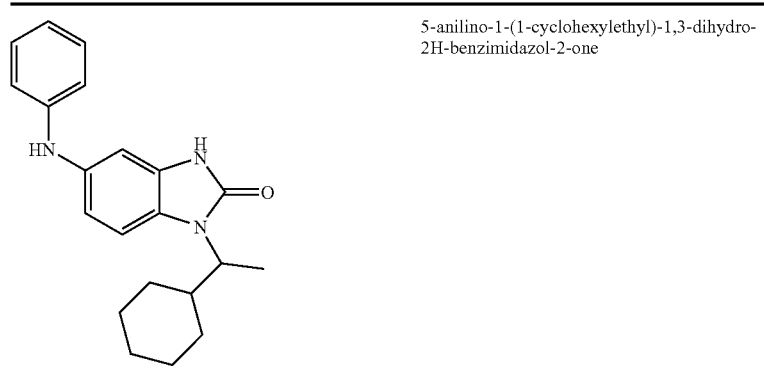
5-anilino-1-(1-cyclohexylethyl)-1,3-dihydro-2H-benzimidazol-2-one
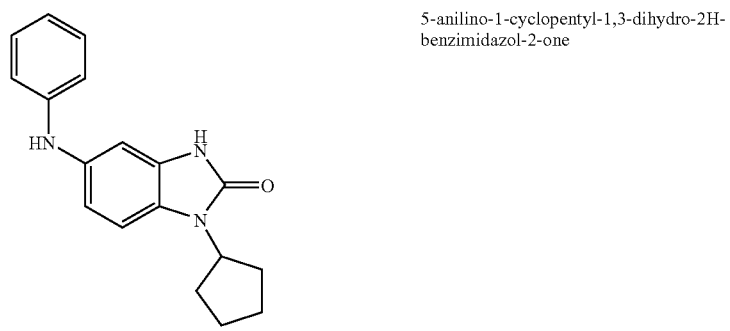
5-anilino-1-cyclopentyl-1,3-dihydro-2H-benzimidazol-2-one
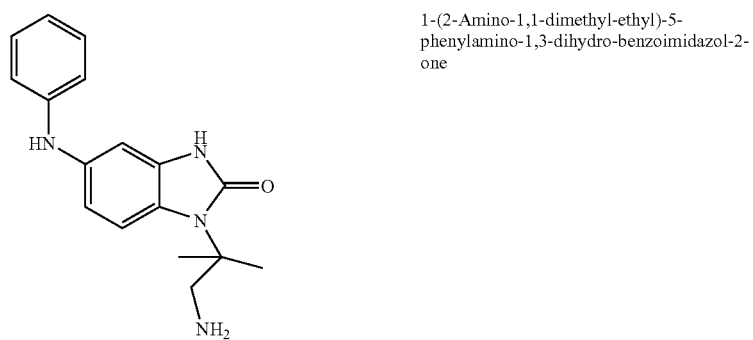
1-(2-Amino-1,1-dimethyl-ethyl)-5-phenylamino-1,3-dihydro-benzoimidazol-2-one
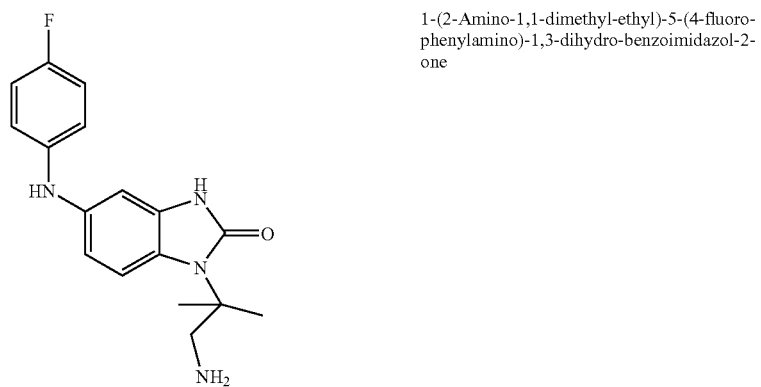
1-(2-Amino-1,1-dimethyl-ethyl)-5-(4-fluoro-phenylamino)-1,3-dihydro-benzoimidazol-2-one TABLE III-continued
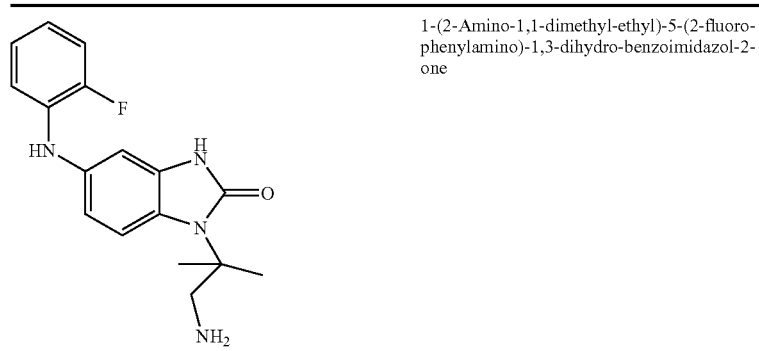
1-(2-Amino-1,1-dimethyl-ethyl)-5-(2-fluoro-phenylamino)-1,3-dihydro-benzoimidazol-2-one
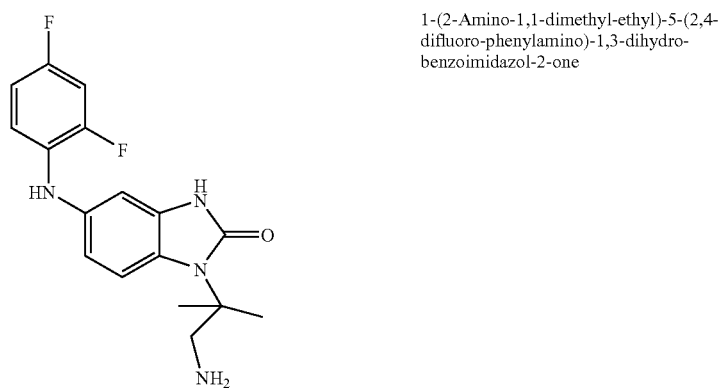
1-(2-Amino-1,1-dimethyl-ethyl)-5-(2,4-difluoro-phenylamino)-1,3-dihydro-benzoimidazol-2-one
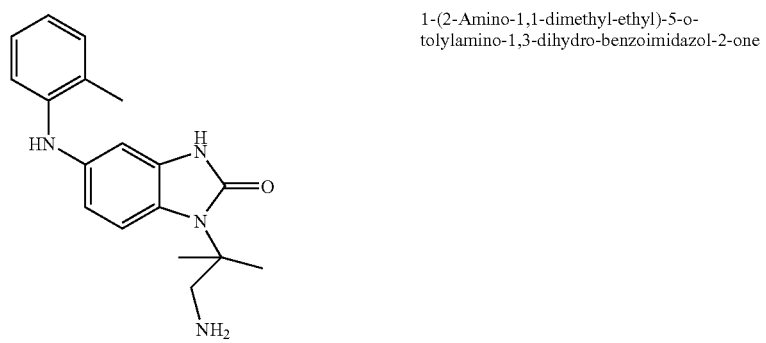
1-(2-Amino-1,1-dimethyl-ethyl)-5-o-tolylamino-1,3-dihydro-benzoimidazol-2-one
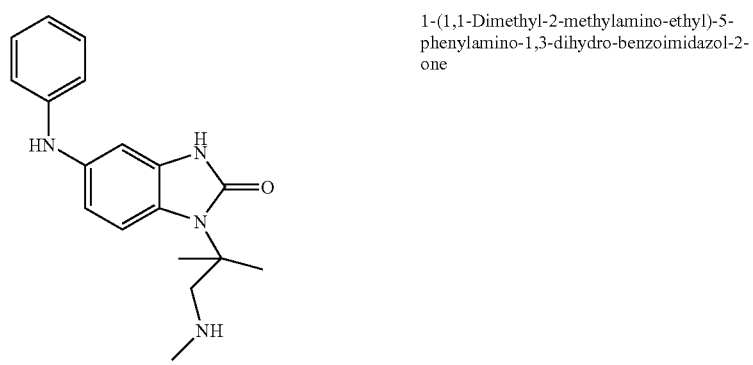
1-(1,1-Dimethyl-2-methylamino-ethyl)-5-phenylamino-1,3-dihydro-benzoimidazol-2-one TABLE III-continued
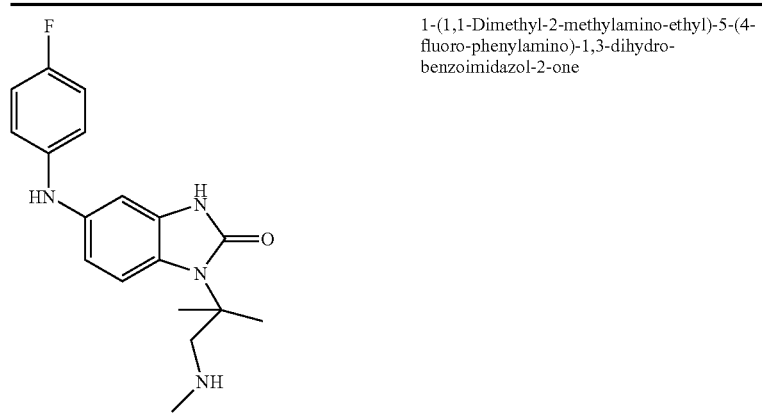
1-(1,1-Dimethyl-2-methylamino-ethyl)-5-(4-fluoro-phenylamino)-1,3-dihydro-benzoimidazol-2-one
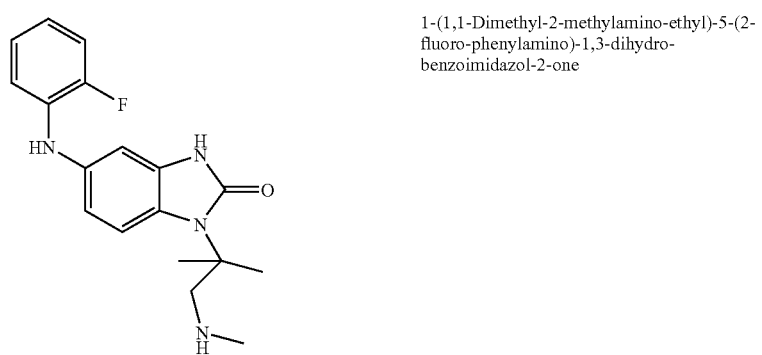
1-(1,1-Dimethyl-2-methylamino-ethyl)-5-(2-fluoro-phenylamino)-1,3-dihydro-benzoimidazol-2-one
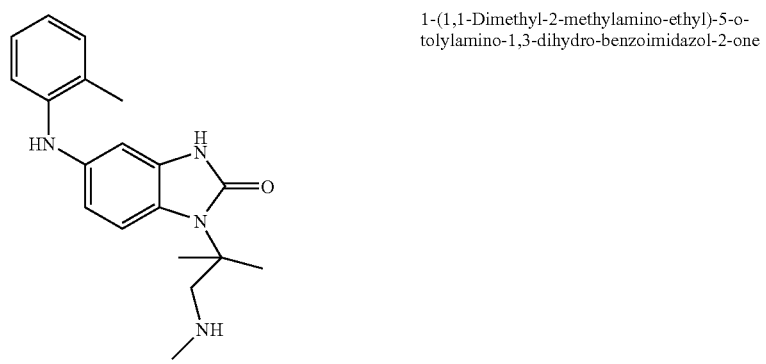
1-(1,1-Dimethyl-2-methylamino-ethyl)-5-o-tolylamino-1,3-dihydro-benzoimidazol-2-one
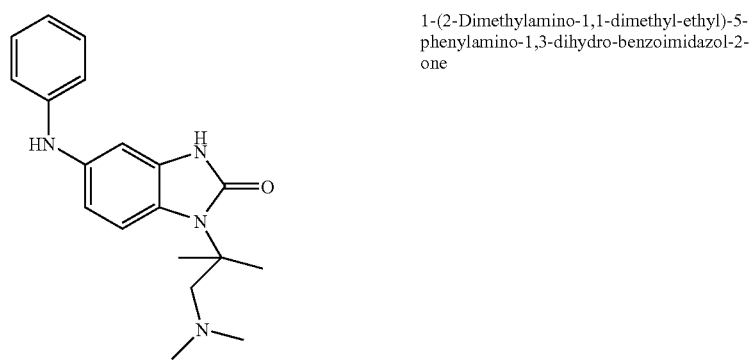
1-(2-Dimethylamino-1,1-dimethyl-ethyl)-5-phenylamino-1,3-dihydro-benzoimidazol-2-one TABLE III-continued
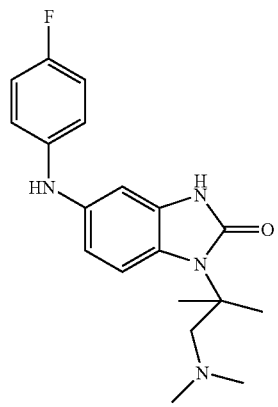
1-(2-Dimethylamino-1,1-dimethyl-ethyl)-5-
((1E,3E)-4-fluoro-1-vinyl-penta-1,3-
dienylamino)-1,3-dihydro-benzoimidazol-2-
one
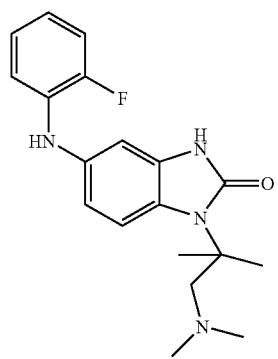
1-(2-Dimethylamino-1,1-dimethyl-ethyl)-5-(2-
fluoro-phenylamino)-1,3-dihydro-
benzoimidazol-2-one
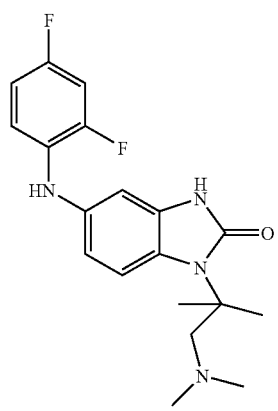
5-(2,4-Difluoro-phenylamino)-1-(2-
dimethylamino-1,1-dimethyl-ethyl)-1,3-
dihydro-benzoimidazol-2-one
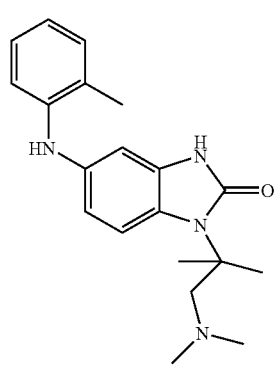
1-(2-Dimethylamino-1,1-dimethyl-ethyl)-5-o-
tolylamino-1,3-dihydro-benzoimidazol-2-one TABLE III-continued
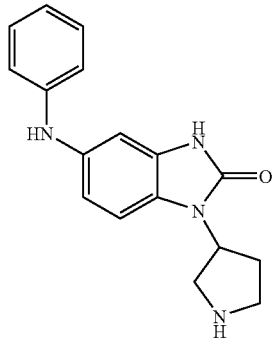
5-Phenylamino-1-pyrrolidin-3-yl-1,3-dihydro-benzoimidazol-2-one
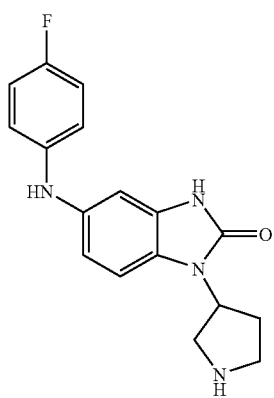
5-(4-Fluoro-phenylamino)-1-pyrrolidin-3-yl-1,3-dihydro-benzoimidazol-2-one
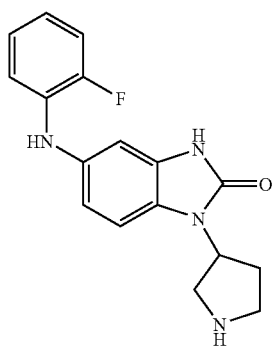
5-(2-Fluoro-phenylamino)-1-pyrrolidin-3-yl-1,3-dihydro-benzoimidazol-2-one
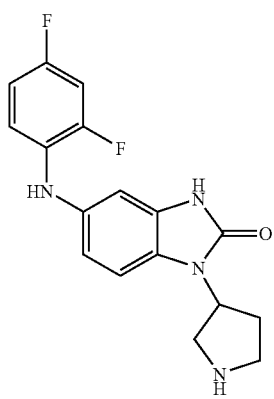
5-(2,4-Difluoro-phenylamino)-1-pyrrolidin-3-yl-1,3-dihydro-benzoimidazol-2-one TABLE III-continued
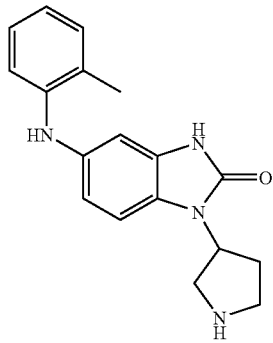
1-Pyrrolidin-3-yl-5-o-tolylamino-1,3-dihydro-benzoimidazol-2-one
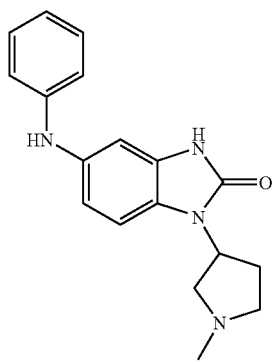
1-(1-Methyl-pyrrolidin-3-yl)-5-phenylamino-1,3-dihydro-benzoimidazol-2-one
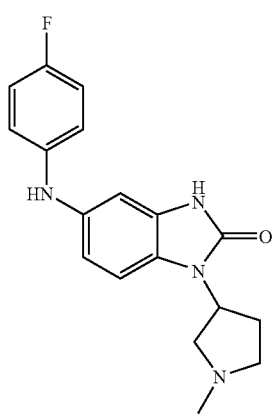
5-(4-Fluoro-phenylamino)-1-(1-methyl-pyrrolidin-3-yl)-1,3-dihydro-benzoimidazol-2-one
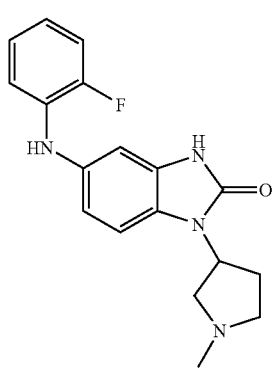
5-(2-Fluoro-phenylamino)-1-(1-methyl-pyrrolidin-3-yl)-1,3-dihydro-benzoimidazol-2-one TABLE III-continued
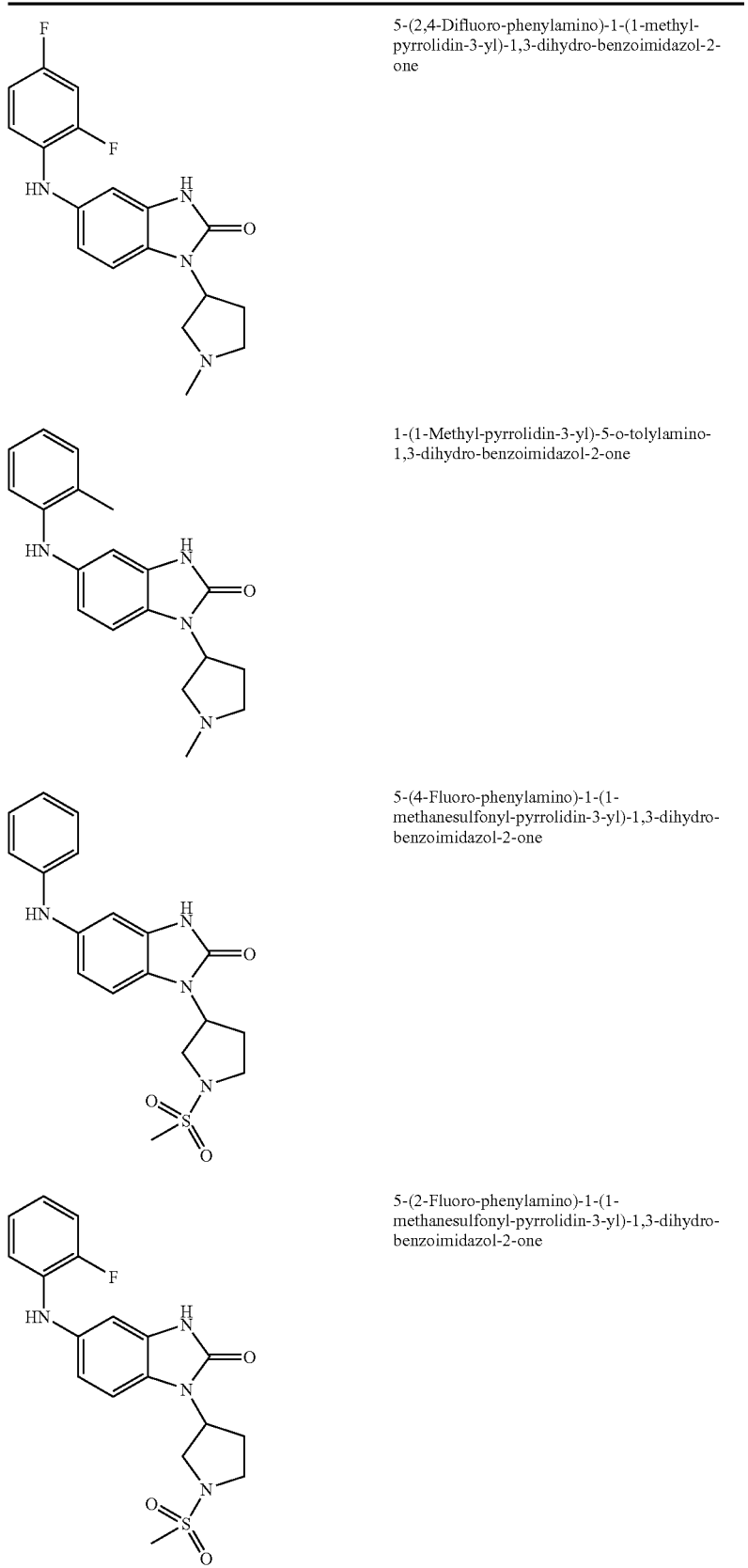
5-(2,4-Difluoro-phenylamino)-1-(1-methyl-pyrrolidin-3-yl)-1,3-dihydro-benzoimidazol-2-one
1-(1-Methyl-pyrrolidin-3-yl)-5-o-tolylamino-1,3-dihydro-benzoimidazol-2-one
5-(4-Fluoro-phenylamino)-1-(1-methanesulfonyl-pyrrolidin-3-yl)-1,3-dihydro-benzoimidazol-2-one
5-(2-Fluoro-phenylamino)-1-(1-methanesulfonyl-pyrrolidin-3-yl)-1,3-dihydro-benzoimidazol-2-one

TABLE III-continued
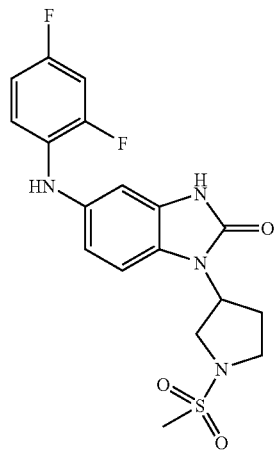
5-(2,4-Difluoro-phenylamino)-1-(1-methanesulfonyl-pyrrolidin-3-yl)-1,3-dihydro-benzoimidazol-2-one
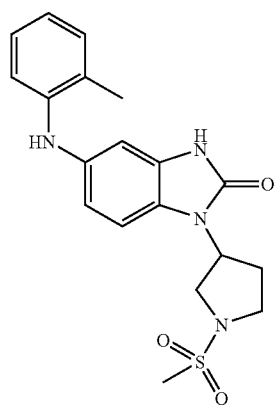
1-(1-Methanesulfonyl-pyrrolidin-3-yl)-5-o-tolylamino-1,3-dihydro-benzoimidazol-2-one
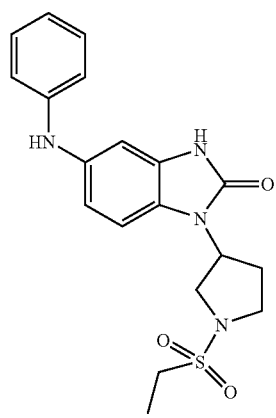
1-(1-Ethanesulfonyl-pyrrolidin-3-yl)-5-phenylamino-1,3-dihydro-benzoimidazol-2-one

TABLE III-continued
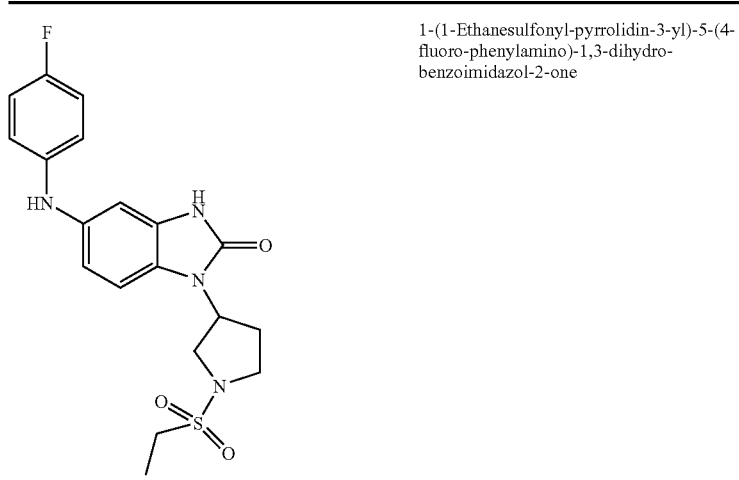
1-(1-Ethanesulfonyl-pyrrolidin-3-yl)-5-(4-fluoro-phenylamino)-1,3-dihydro-benzoimidazol-2-one
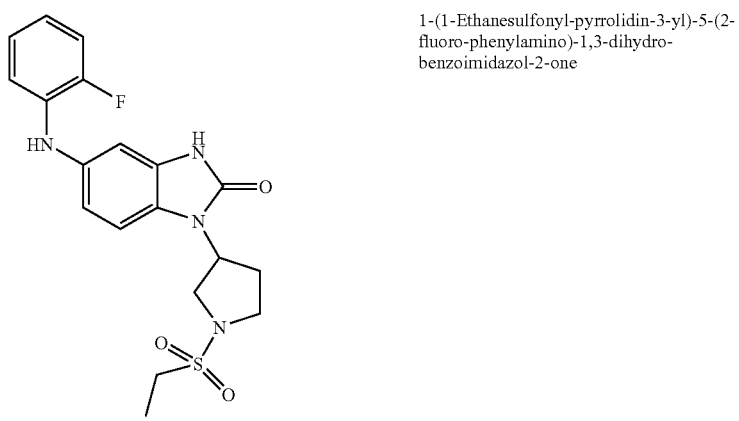
1-(1-Ethanesulfonyl-pyrrolidin-3-yl)-5-(2-fluoro-phenylamino)-1,3-dihydro-benzoimidazol-2-one
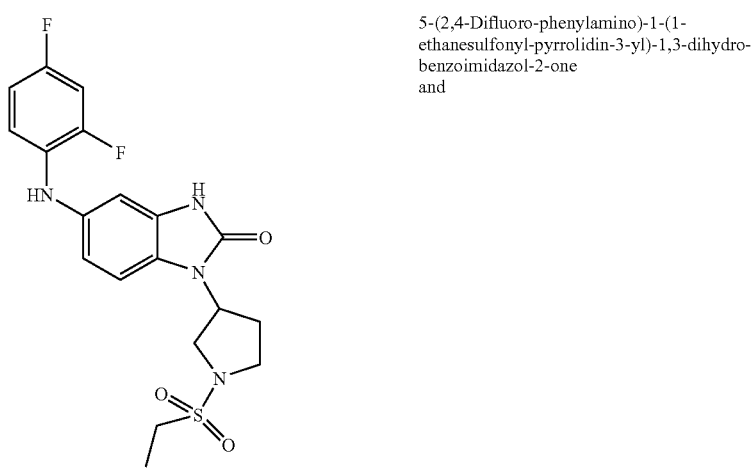
5-(2,4-Difluoro-phenylamino)-1-(1-ethanesulfonyl-pyrrolidin-3-yl)-1,3-dihydro-benzoimidazol-2-one
and TABLE III-continued

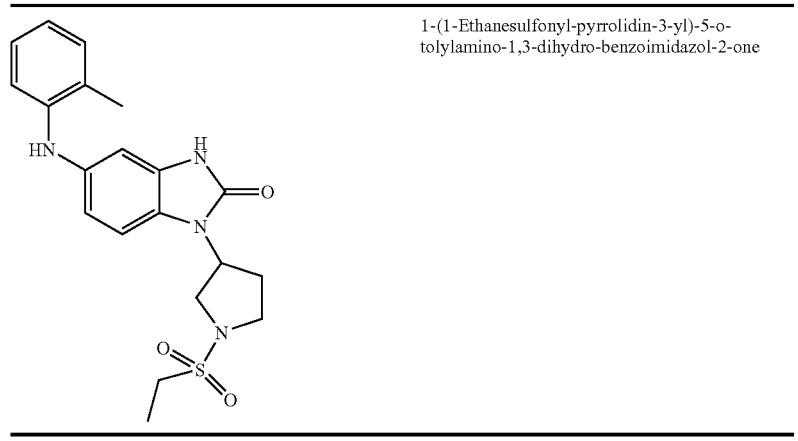

1-(1-Ethanesulfonyl-pyrrolidin-3-yl)-5-o-tolylamino-1,3-dihydro-benzoimidazol-2-one or the pharmaceutically acceptable acids and salts or isomers thereof.

In a second broad generic aspect of the invention, there are provided compounds of the formula (II)

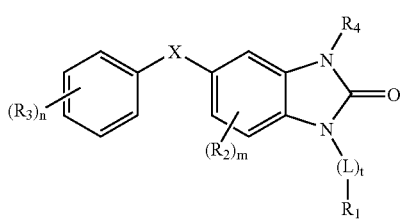

(II)

wherein:

X is O, or S;

z, m and n are independently 0, 1 or 2;

t is 0–10;

L is —$CH_2$— optionally substituted by alkyl or alkoxy;

$R_1$ is chosen from amino, alkyl, $C_{3-7}$ cycloalkyl, aryl, heteroaryl and heterocyclyl each optionally substituted by $R_a$;

$R_2$ is chosen from mono-or-di-alkylamino, alkylthio, alkoxy, $C_{3-7}$ cycloalkyl, aryl, heteroaryl and heterocyclyl each optionally substituted by $R_b$;

each $R_a$ and $R_b$ are independently chosen from alkyl, alkenyl, alkynyl, cycloalkyl, aryl, heteroaryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, oxo, halogen, trifluoromethyl, nitro, nitrile and amino or guanidino each optionally mono-or-di-substituted by alkyl, acyl or alkoxycarbonyl, wherein any of the above $R_a$ or $R_b$ are optionally halogenated where possible;

each $R_3$ is chosen from alkyl, alkenyl, alkynyl, cycloalkyl, aryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-or-di-substituted by alkyl, acyl or alkoxycarbonyl, wherein any of the above $R_3$ are optionally halogenated where possible; and $R_4$ and $R_5$ are independently chosen from hydrogen and $C_{1-3}$ alkyl;

or the pharmaceutically acceptable acids and salts or isomers thereof.

In a second embodiment there are provided compounds of the formula (II) as described immediately above and wherein:

m is 0;

n is 0, 1 or 2;

t is 0–5;

L is —$CH_2$— optionally substituted by methyl, ethyl or propyl;

$R_1$ is chosen from amino, $C_{1-6}$ alkyl, $C_{3-7}$ cycloalkyl, indanyl, indenyl, phenyl naphthyl, heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl and heterocyclyl chosen from aziridinyl, pyrrolidinyl, pyrrolinyl, morpholinyl, thiomorpholinyl, tetrahydrofuranyl, dioxalanyl, pyranyl, piperidinyl and piperazinyl, each optionally substituted by one to three $R_a$;

$R_2$ is chosen from mono- or di-$C_{1-5}$ alkyl amino, $C_{1-5}$ alkylthio, $C_{1-5}$ alkoxy, $C_{3-7}$ cycloalkyl, aryl, heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl and heterocyclyl chosen from aziridinyl, pyrrolidinyl, pyrrolinyl, morpholinyl, thiomorpholinyl, tetrahydrofuranyl, dioxalanyl, pyranyl, piperidinyl and piperazinyl, each optionally substituted by one to three $R_b$;

each $R_a$ and $R_b$ are independently chosen from $C_{1-5}$ alkyl, $C_{2-5}$ alkenyl, $C_{2-5}$ alkynyl, $C_{3-7}$ cycloalkyl, aryl, arylalkyl, aryloxy, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_a$ is optionally halogenated where possible;

each $R_3$ is chosen from hydrogen, $C_{1-5}$ alkyl, $C_{2-5}$ alkenyl, $C_{2-5}$ alkynyl, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_3$ are optionally halogenated where possible; and $R_4$ and $R_5$ are independently chosen from hydrogen and methyl.

In a third embodiment there are provided compounds of the formula (II) as described immediately above and wherein:

t is 0–3;

L is —$CH_2$— optionally substituted by methyl;

$R_1$ is chosen from $C_{3-6}$ alkyl, amino, $C_{3-7}$ cycloalkyl, indanyl, indenyl, phenyl, naphthyl, heteroaryl chosen from isoxazolyl, oxazolyl, thiadiazolyl, tetrazolyl, pyrazolyl, pyrrolyl, imidazolyl, pyridinyl, pyrimidinyl, pyrazinyl, pyridazinyl, quinoxalinyl, indolyl, benzimidazolyl, benzoxazolyl, benzothiazolyl, quinolinyl, quinazolinyl and indazolyl and heterocyclyl chosen from pyrrolidinyl, pyrrolinyl, morpholinyl, thiomorpholinyl, tetrahydrofuranyl, dioxalanyl, tetrahydropyranyl, piperidinyl and piperazinyl, each optionally substituted by one to two $R_a$;

each $R_a$ and $R_b$ are independently chosen from $C_{1-5}$ alkyl, aryloxy, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_a$ is optionally halogenated where possible;

each $R_3$ is chosen from $C_{1-5}$ alkyl, $C_{1-5}$ alkoxy, $C_{1-5}$ alkylthio, $C_{1-5}$ acyl, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-3}$ alkyl, wherein any of the above $R_3$ are optionally halogenated where possible;

$R_4$ is hydrogen; and and $R_5$ is hydrogen or methyl.

In a fourth embodiment there are provided compounds of the formula (II) as described immediately above and wherein:

R, is chosen from $C_{4-6}$ alkyl, amino, $C_{5-7}$ cycloalkyl, indanyl, indenyl, phenyl, naphthyl, tetrahydronaphthyl, pyridinyl, pyrimidinyl, pyrazinyl, pyridazinyl, pyrrolidinyl, pyrrolinyl, tetrahydrofuranyl, piperidinyl and dioxalanyl, each optionally substituted by one to two $R_a$;

each $R_a$ and $R_b$ are independently chosen from $C_{1-5}$ alkyl, aryloxy, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_a$ is optionally halogenated where possible;

each $R_3$ is chosen from $C_{1-5}$ alkyl, $C_{1-5}$ alkoxy, $C_{1-5}$ alkylthio, $C_{1-5}$ acyl, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-3}$ alkyl, wherein any of the above $R_3$ are optionally halogenated where possible;

$R_4$ and $R_5$ are hydrogen.

In a fifth embodiment there are provided compounds of the formula (II) as described immediately above and wherein:

t is 0 or 1;

$R_1$ is chosen from $C_4$ alkyl, amino, $C_{5-6}$ cycloalkyl, indanyl, indenyl, phenyl, naphthyl, tetrahydronaphthyl, pyridinyl, tetrahydrofuranyl and piperidinyl, each optionally substituted by one to two $R_a$;

each $R_a$ is independently chosen from $C_{1-5}$ alkyl, $C_{1-5}$ alkoxy, $C_{4-6}$ alkoxycarbonyl, hydroxy, halogen, trifluoromethyl, nitro, nitrile and amino wherein any of the above $R_a$ is optionally halogenated where possible;

each $R_3$ is chosen from $C_{1-3}$ alkyl, $C_{1-3}$ alkoxy, hydroxy, halogen, trifluoromethyl, nitro, nitrile and amino wherein any of the above $R_3$ are optionally halogenated where possible.

In a sixth embodiment there are provided compounds of the formula (II) as described immediately above and wherein:

X is O;

$R_1$ is chosen from t-butyl, amino, $C_{5-6}$ cycloalkyl, indanyl, indenyl, phenyl, naphthyl, tetrahydronaphthyl, pyridinyl, tetrahydrofuranyl and piperidinyl, each optionally substituted by one to two $R_a$;

each $R_a$ is chosen from $C_{1-5}$ alkyl, methoxy, tert-butoxycarbonyl, fluoro, trifluoromethyl and amino; and each $R_3$ is chosen from methyl, methoxy, fluoro, trifluoromethyl and amino.

In a seventh embodiment there are provided compounds of the formula (II) as described immediately above and wherein:

$R_1$ is chosen from t-butyl, amino, cyclohexyl and phenyl, the phenyl is optionally substituted by one to two $R_a$.

In an eight embodiment there are provided compounds of the formula (II) as described in the fifth embodiment above and wherein:

X is O;

each $R_a$ is chosen from methyl, methoxy, tert-butoxycarbonyl, fluoro, trifluoromethyl and amino; and each $R_3$ is chosen from methyl and fluoro.

In a ninth embodiment there are provided compounds of the formula (II) as described immediately above and wherein:

$R_1$ is cyclohexyl.

In an tenth embodiment there are provided compounds of the formula (II) as described second embodiment above and wherein:

$R_2$ is mono- or di $C_{1-5}$ alkyl amino further substituted by mono- or di $C_{1-5}$ alkyl amino.

In an eleventh embodiment there are provided compounds of the formula (II) as described second embodiment above and wherein:

$R_2$ is chosen from $C_{1-3}$ alkylthio or $C_{1-3}$ alkoxy each further substituted by mono-or di $C_{1-5}$ alkyl amino.

The following are representative compounds of the formula (II) and can be made by the general schemes and examples disclosed herein:

TABLE IV
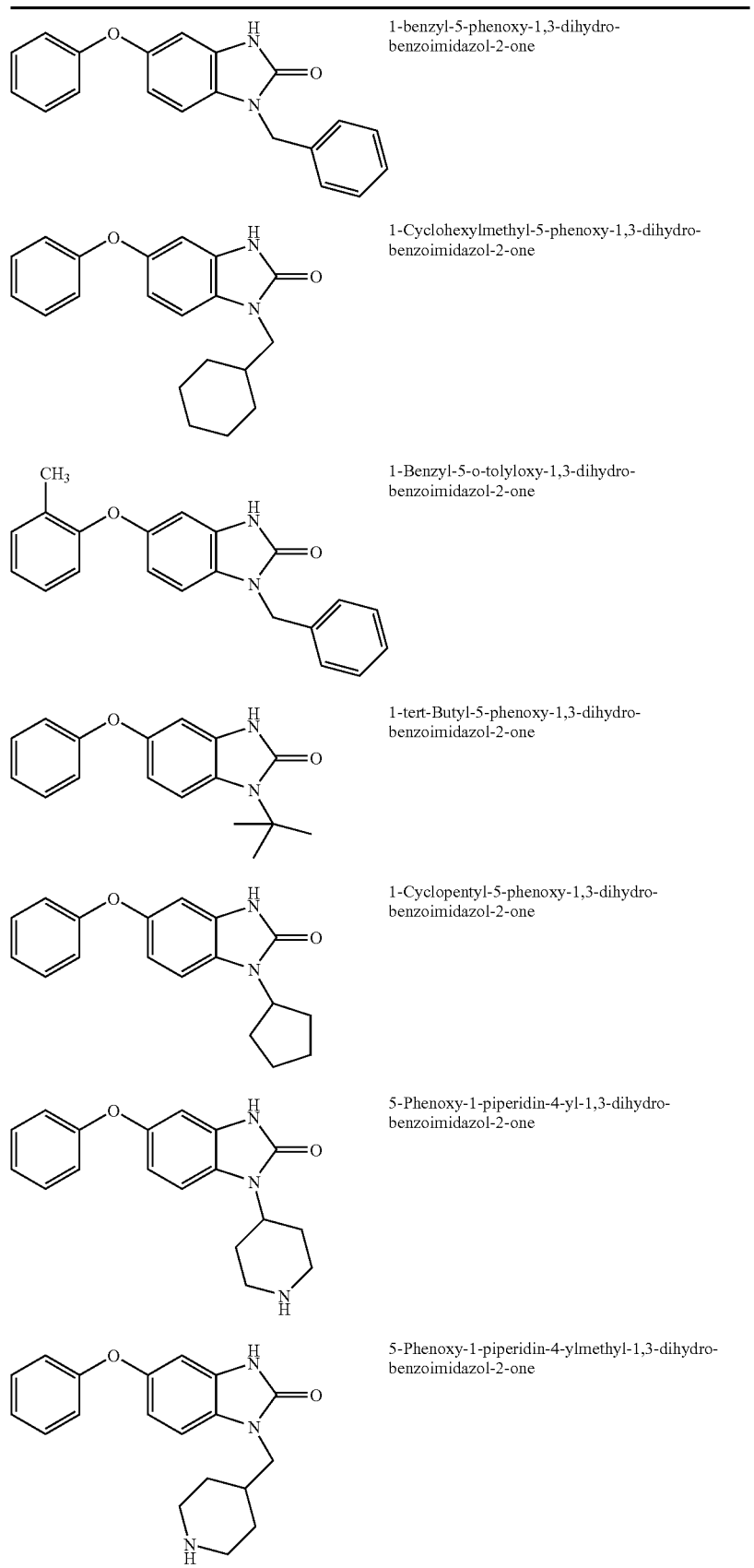
1-benzyl-5-phenoxy-1,3-dihydro-benzoimidazol-2-one
1-Cyclohexylmethyl-5-phenoxy-1,3-dihydro-benzoimidazol-2-one
1-Benzyl-5-o-tolyloxy-1,3-dihydro-benzoimidazol-2-one
1-tert-Butyl-5-phenoxy-1,3-dihydro-benzoimidazol-2-one
1-Cyclopentyl-5-phenoxy-1,3-dihydro-benzoimidazol-2-one
5-Phenoxy-1-piperidin-4-yl-1,3-dihydro-benzoimidazol-2-one
5-Phenoxy-1-piperidin-4-ylmethyl-1,3-dihydro-benzoimidazol-2-one TABLE IV-continued

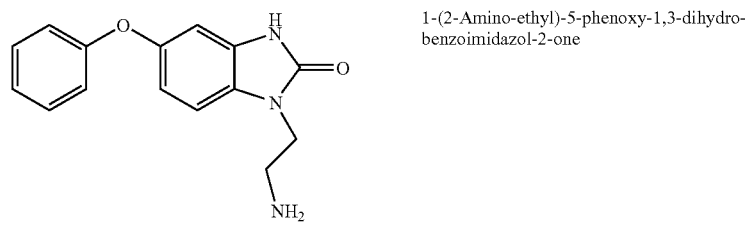
1-(2-Amino-ethyl)-5-phenoxy-1,3-dihydro-benzoimidazol-2-one

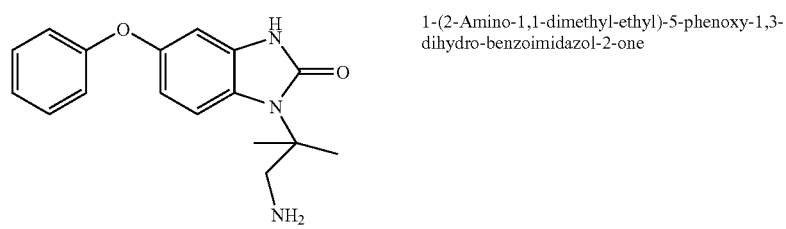
1-(2-Amino-1,1-dimethyl-ethyl)-5-phenoxy-1,3-dihydro-benzoimidazol-2-one

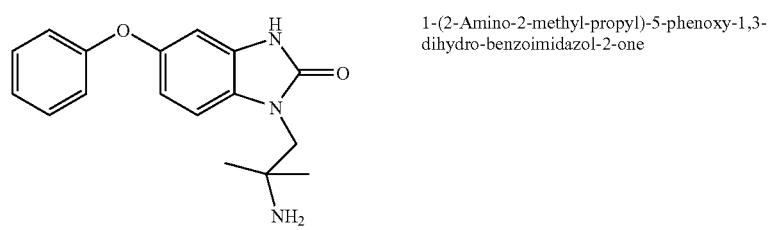
1-(2-Amino-2-methyl-propyl)-5-phenoxy-1,3-dihydro-benzoimidazol-2-one

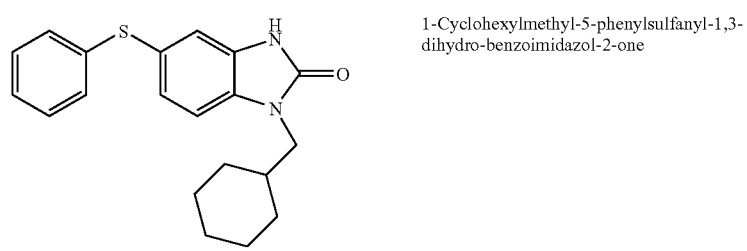
1-Cyclohexylmethyl-5-phenylsulfanyl-1,3-dihydro-benzoimidazol-2-one

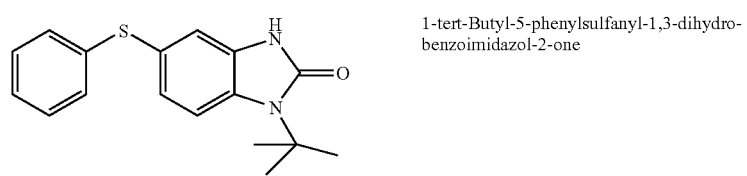
1-tert-Butyl-5-phenylsulfanyl-1,3-dihydro-benzoimidazol-2-one

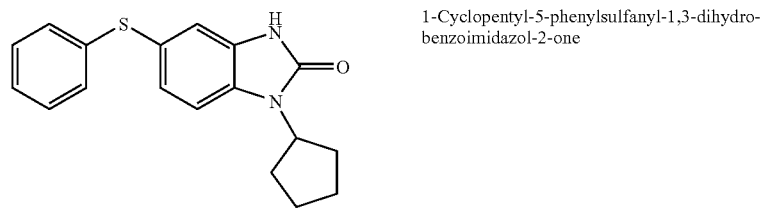
1-Cyclopentyl-5-phenylsulfanyl-1,3-dihydro-benzoimidazol-2-one

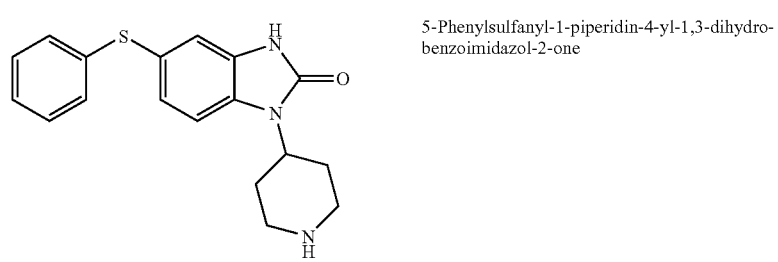
5-Phenylsulfanyl-1-piperidin-4-yl-1,3-dihydro-benzoimidazol-2-one

TABLE IV-continued

| Structure | Name |
|---|---|
| 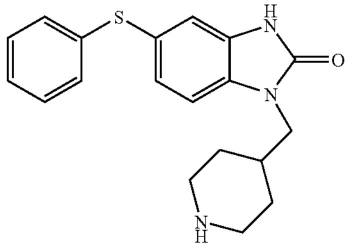 | 5-Phenylsulfanyl-1-piperidin-4-ylmethyl-1,3-dihydro-benzoimidazol-2-one |
| 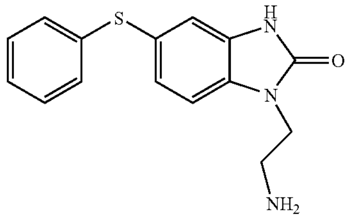 | 1-(2-Amino-ethyl)-5-phenylsulfanyl-1,3-dihydro-benzoimidazol-2-one |
| 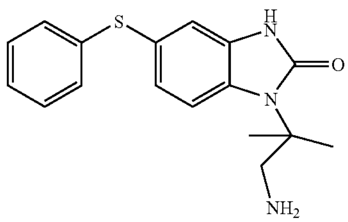 | 1-(2-Amino-1,1-dimethyl-ethyl)-5-phenylsulfanyl-1,3-dihydro-benzoimidazol-2-one |
| | 1-(2-Amino-2-methyl-propyl)-5-phenylsulfanyl-1,3-dihydro-benzoimidazol-2-one | or the pharmaceutically acceptable acids and salts or isomers thereof.

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formulas (I)/(II) can exist in more than one tautomeric form.

The invention includes methods using all such tautomers.

All terms as used herein in this specification, unless otherwise stated, shall be understood in their ordinary meaning as known in the art. For example, "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic and non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used inerchangeably.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-λ4-thiomorpholinyl, 13-oxa-11-azatricyclo[7.3.1.0-2,7]trideca-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5–8 membered monocyclic or 8–11 membered bicyclic ring containing 1–4 heteroatoms such as N, O and S. Unless otherwise stated, such heteroaryls include aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

Terms which are analogs of the above cyclic moieties such as aryloxy or heteroaryl amine shall be understood to mean an aryl, heteroaryl, heterocycle as defined above attached to it's respective group.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I)/(II). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I)/(II).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$–$C_4$ alkyl)$_4^+$ salts.

In addition, within the scope of the invention is use of prodrugs of compounds of the formula (I)/(II). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

METHODS OF USE

In accordance with the invention, there are provided novel methods of using the compounds of the formulas (I)/(II). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, toxic shock syndrome, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The compounds of the invention may also be useful for anticoagulant or fibrinolytic therapy (and the diseases or conditions related to such therapy) as described in the provisional application with attorney docket number 9/257 PV filed Aug. 14, 2002.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US01/21860 and U.S. provisional application No. 60/313,527, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I)/(II) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. Reference in this regard may also be made to U.S. provisional application No. 60/339,249. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

General Synthetic Methods

The invention additionally provides for methods of making the compounds of the formulas (I) and (II). The compounds of the invention may be prepared by the general methods and examples presented below, and methods known to those of ordinary skill in the art. In the schemes below, unless otherwise specified, $R^1-R^5$, L, X, n, m and t in the formulas shown below shall have the meanings defined for these groups in the definition of the formula (I) and (II) of the invention, described hereinabove. Intermediates used in the syntheses below are either commercially available or easily prepared by methods known to those skilled in the art. Reaction progress may be monitored by conventional methods such as thin layer chromatography (TLC). Intermediates and products may be purified by methods known in the art, including column chromatography, HPLC or recrystallization.

Compounds of formula (I) may be prepared by the method described in Scheme I.

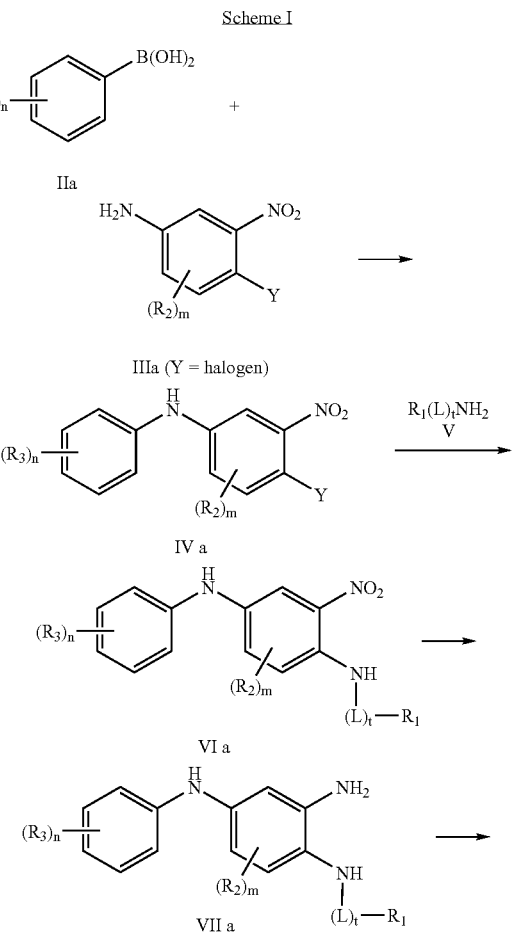

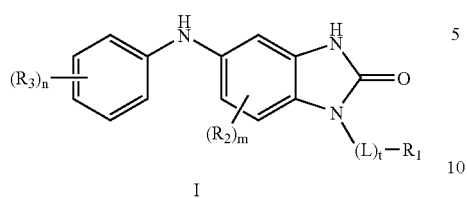

I

As illustrated above, an arylboronic acid (IIa) is coupled with a 4-halo-3-nitroaniline (IIIa), a), preferably a 4-fluoro-3-nitroaniline in the presence of a copper salt, preferrably copper (II) acetate, and a suitable base such as triethylamine in a solvent such as dichloromethane. Preferably, an agent to remove water formed in the reaction, such as 4 Å molecular sieves is present in the reaction mixture. The product IV a is reacted with an amine Va in the presence of a base such as N,N'-diisopropylethylamine, in a suitable solvent such as DMF to form VI a. The nitro group of VI a is reduced by methods known in the art for example by stirring in a suitable solvent such as THF under a hydrogen atmosphere in the presence of a catalyst such as palladium on carbon to form VII. The benzimidazol-2-one may then be formed by reaction of VII with a carbonyl source such as carbonyldiimidazole in a suitable solvent such as THF to provide the desired I.

Compounds of formula (I) in which $R_2$ is an amine may be prepared as described in Scheme II.

Scheme II

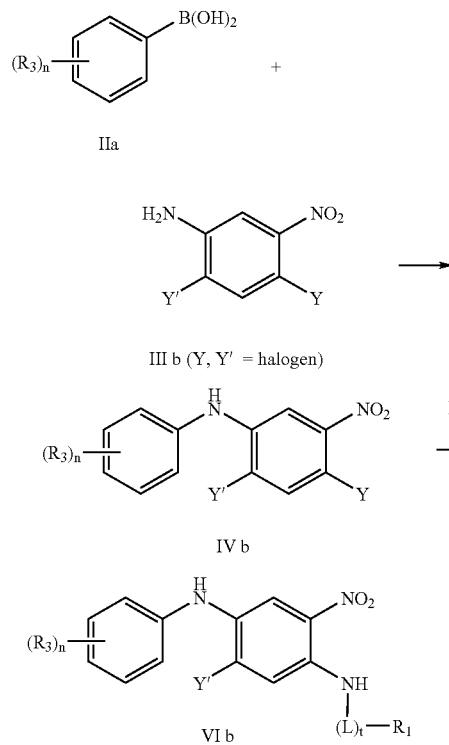

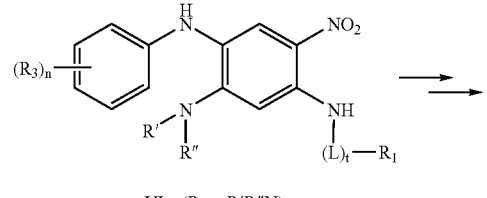

VI c ($R_2$ = R'R"N)

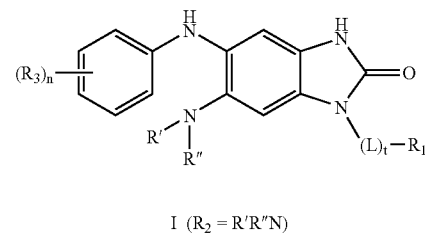

I ($R_2$ = R'R"N)

Reaction of IIa with III b (Y and Y' are halogen, preferably fluorine) using the procedure described in Scheme I provides the dihalobenzene intermediate IV b. The halogens are displaced sequentially, first by reaction with V as described in Scheme I, to form VI b, and then by reaction with an amine R'NH$_2$, using the same procedure to form VI c. Subsequent reduction of the nitro group and formation of the 2-benzimidazolone as described in Scheme I provides the desired compound of formula (I) in which $R_2$ is an amine or a nitrogen containing heterocycle (R'R"N).

Compounds of formula (II) having X=O may be prepared using the procedure described in Scheme I by replacing intermediate IIa with the a 4-halo-3-nitro-phenol (IIIc).

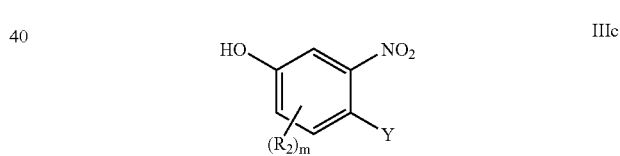

Compounds of formula (II) having X=S may be prepared by the method illustrated in Scheme III Scheme III

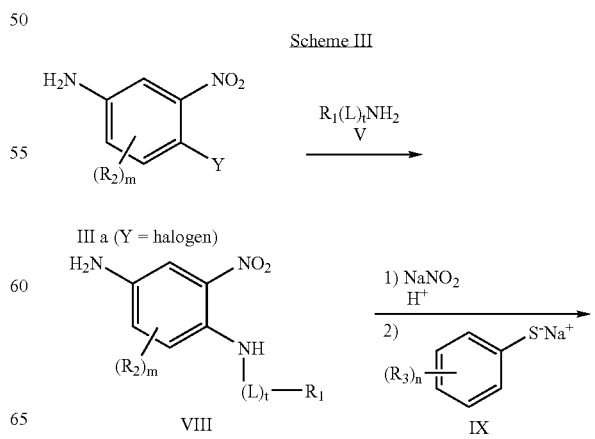

-continued

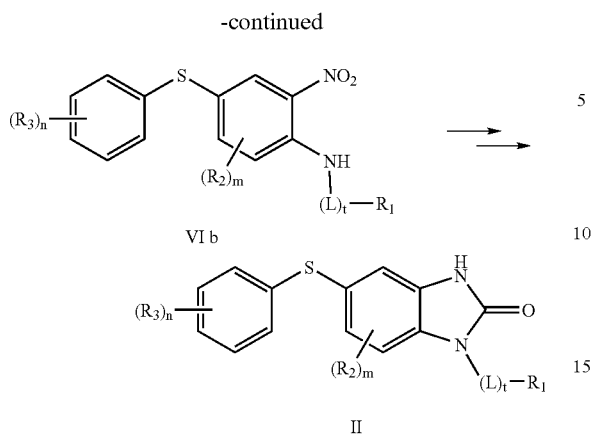

As illustrated in Scheme III, a 4-halo-3-nitroaniline (III a) is reacted with an amine $R_1(L)_tNH_2$ (V) in the presence of a base such as N,N'-diisopropylethylamine, in a suitable solvent such as DMF to form VIII. Intermediate VIII is reacted with $NaNO_2$ in the presence of an aqueous acid such as 48% $HBF_4$ to form a diazonium salt which is then reacted with the mercaptan salt IX to form VI b. Intermediate VI b is then reduced and cyclized as described for VI a in Scheme I to provide the desired compound of formula (II) having X=S. The thioether group of II or one of the thioether-containing intermediates may be oxidized by methods known in the art, for example by treatment with m-chloroperoxybenzoic acid to provide compounds of formula (II) having $X=S(O)_2$ or hydrogen peroxide to provide compounds of formula (II) having X=S(O).

SYNTHETIC EXAMPLES

Example 1

Synthesis of 1-cyclohexylmethyl-5-phenylamino-1,3-dihydro-benzoimidazol-2-one

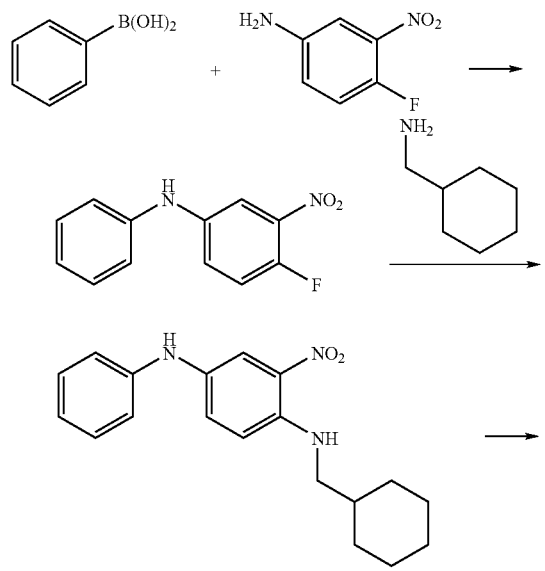

-continued

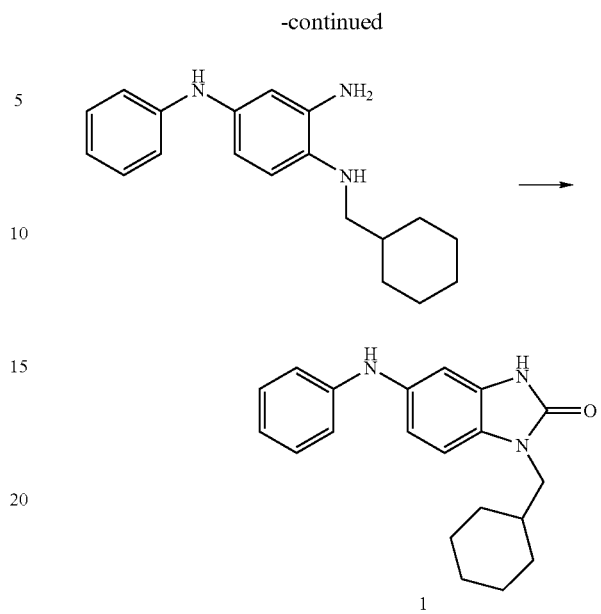

A mixture of the 4-fluoro-3-nitroaniline (5.00 g, 32.03 mmol), phenylboronic acid (7.81 g, 64.05 mmol), copper(II) acetate (5.82 g, 32.03 mmol) and 4 Å molecular sieves (5.00 g) in dichloromethane (200.0 mL) and triethylamine (22.3 mL, 160 mmol) was placed in a round bottomed flask. The resulting suspension was stirred at room temperature under a dry ambient atmosphere for 48 h. The mixture was filtered through diatomaceous earth and the solvent was removed via rotary evaporation. The resulting residue was re-dissolved in EtOAc, adsorbed on silica gel and flash chromatographed (15% EtOAc/hexanes) to give 4-fluoro-3-nitro-N-phenylaniline as an orange solid (5.24 g, 70.5 % yield). $M^-$, 231.

A solution of 4-fluoro-3-nitro-N-phenylaniline (0.30 g, 1.29 mmol), cyclohexanemethylamine (0.50 mL, 3.88 mmol) and N,N'-diisopropylethylamine (0.68, 3.88 mmol) in DMF (10 mL) was stirred at 100° C. under an inert atmosphere for 17 h. The reaction mixture was transferred to a separatory funnel containing 2 N HCl. The aqueous layer was extracted with EtOAc and the combined organic layers were washed with water, brine and dried over $MgSO_4$. The solution was filtered through diatomaceous earth and the solvent was removed via rotary evaporation. The resulting dark red residue was flash chromatographed (10% EtOAc/hexanes) to give $N^1$-cyclohexylmethyl-2-nitro-N-4-phenyl-benzene-1,4-diamine as a purple solid (0.27 g, 64.1% yield). $M^+$, 326.

To a solution of $N^1$-cyclohexylmethyl-2-nitro-$N^4$-phenyl-benzene-1,4-diamine (0.06 g, 0.18 mmol) in THF (5.00 mL) was added 10% palladium on activated carbon (60 mg). The reaction flask was equipped with a septum and was placed under vacuum for 3 min. The flask was then placed under hydrogen atmosphere (balloon inflated with hydrogen) and the reaction mixture was stirred for 16 h. The palladium was filtered off through a plug of diatomaceous earth and washed with EtOAc. The solvent was removed via rotary evaporation. The resulting residue was flash chromatographed (30% EtOAc/hexanes), providing $N^1$-cyclohexylmethyl-$N^4$-phenyl-benzene-1,2,4-triamine as a purple foam (0.04 g, 75.6% yield). $M^+$, 294.

A solution of N¹-cyclohexylmethyl-N-phenyl-benzene-1,2,4-triamine (0.04 g, 0.14 mmol) and 1,1'-carbonyldiimidazole (0.07 g, 0.41 mmol) in THF (3.00 mL) was stirred at room temperature for 16 h. The solvent was removed via rotary evaporation. The resulting residue was flash chromatographed (45% EtOAc/hexanes) to give the title compound as a white solid (0.03 g, 65.0% yield). M⁺, 322.

The following compounds were also prepared using the procedure described in the above example:

1-Cyclohexylmethyl-5-(3,5-dichloro-phenylamino)-1,3-dihydro-benzoimidazol-2-one;
5-(3-Amino-4-methyl-phenylamino)-1-cyclohexylmethyl-1,3-dihydro-benzoimidazol-2-one;
1-Cyclohexylmethyl-5-(2-fluoro-phenylamino)-1,3-dihydro-benzoimidazol-2-one;
1-Cyclohexylmethyl-5-(2-methoxy-phenylamino)-1,3-dihydro-benzoimidazol-2-one;
1-Cyclohexylmethyl-5-(3-trifluoromethyl-phenylamino)-1,3-dihydro-benzoimidazol-2-one;
1-Cyclohexylmethyl-5-(4-fluoro-phenylamino)-1,3-dihydro-benzoimidazol-2-one;
1-Cyclohexylmethyl-5-o-tolylamino-1,3-dihydro-benzoimidazol-2-one;
1-Cyclohexylmethyl-5-(2,4-difluoro-phenylamino)-1,3-dihydro-benzoimidazol-2-one;
1-Cyclohexylmethyl-5-(3-fluoro-phenylamino)-1,3-dihydro-benzoimidazol-2-one;
1-Cyclohexylmethyl-5-(3,4-difluoro-phenylamino)-1,3-dihydro-benzoimidazol-2-one;
1-Phenyl-5-phenylamino-1,3-dihydro-benzoimidazol-2-one;
1-Cyclohexylmethyl-6-(4-methyl-piperazin-1-yl)-5-phenylamino-1,3-dihydro-benzoimidazol-2-one;
1-Cyclohexylmethyl-5-phenylamino-6-piperazin-1-yl-1,3-dihydro-benzoimidazol-2-one;
1-Cyclopentyl-5-(2-fluoro-phenylamino)-6-(4-methyl-piperazin-1-yl)-1,3-dihydro-benzoimidazol-2-one;
1-Benzyl-5-phenylamino-1,3-dihydro-2H-benzimidazol-2-one;
5-Phenylamino-1-(1-phenylethyl)-1,3-dihydro-2H-benzimidazol-2-one;
5-Phenylamino-1-(1,2,3,4-tetrahydronaphthalen-1-yl)-1,3-dihydro-2H-benzimidazol-2-one;
5-Phenylamino-1-(2,3-dihydro-1H-inden-1-yl)-1,3-dihydro-2H-benzimidazol-2-one;
5-Phenylamino-1-(pyridin-3-ylmethyl)-1,3-dihydro-2H-benzimidazol-2-one;
1-(2,6-Difluorobenzyl)-5-phenylamino-1,3-dihydro-2H-benzimidazol-2-one;
5-Phenylamino-1-(2-phenylethyl)-1,3-dihydro-2H-benzimidazol-2-one;
1-(3-Methoxybenzyl)-5-phenylamino-1,3-dihydro-2H-benzimidazol-2-one;
5-Phenylamino-1-(2-phenylethyl)-1,3-dihydro-2H-benzimidazol-2-one;
5-Phenylamino-1-(tetrahydrofuran-2-ylmethyl)-1,3-dihydro-2H-benzimidazol-2-one;
1-tert-Butyl-5-phenylamino-1,3-dihydro-2H-benzimidazol-2-one;
1-(1-Cyclohexylethyl)-5-phenylamino-1,3-dihydro-2H-benzimidazol-2-one;
1-Cyclopentyl-5-phenylamino-1,3-dihydro-2H-benzimidazol-2-one.

Example 2

Synthesis of 1-cyclohexylmethyl-6-(4-methyl-piperazin-1-yl)-5-phenylamino-1,3-dihydro-benzoimidazol-2-one

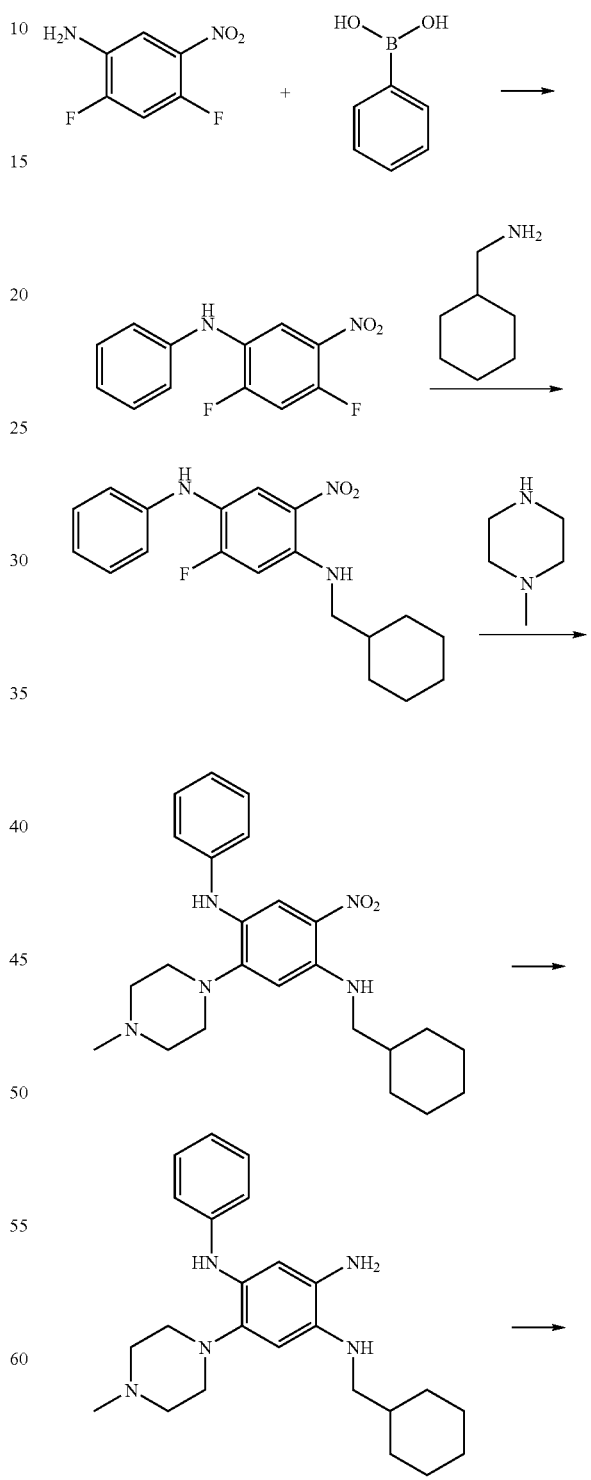

-continued

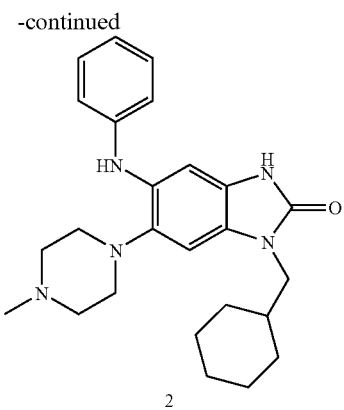

2

A mixture of 2,4-difluoro-5-nitroaniline (3.00 g, 17.23 mmol) (see EP0379894 A3), phenylboronic acid (6.30 g, 51.69 mmol), copper(II) acetate (3.13 g, 17.23 mmol) and 4 Å molecular sieves (3.0 g) in dichloromethane (170.0 mL) and triethylamine (12.01 mL, 43.08 mmol) was placed in a round bottomed flask. The resulting suspension was stirred under at room temperature under a dry ambient atmosphere 50 h. The mixture was filtered through diatomaceous earth and the solvent was evaporated. Additional phenylboronic acid (6.30 g, 51.69 mmol), copper(II) acetate (3.13 g, 17.23 mmol), molecular sieves (3.00 g) triethylamine (12.01 mL, 43.08 mmol), and dichloromethane (170.00 mL) were added and the slurry was stirred for 12 h. The mixture was again filtered through diatomaceous earth and the solvent was evaporated. The resulting residue was re-dissolved in EtOAc, adsorbed on silica and flash chromatographed (15% EtOAc/hexanes) to give 2,4-difluoro-5-nitro-N-phenylaniline as an orange solid (3.92 g, 91% yield).

A solution of 2,4-difluoro-5-nitro-N-phenylaniline (1.00 g, 4.00 mmol), cyclohexanemethylamine (0.57 mL, 4.40 mmol) and N,N'-diisopropylethylamine (0.77, 4.40 mmol) in DMF (40 mL) was stirred at room temperature under an inert atmosphere for 18.5 h. The reaction mixture was transferred to a separatory funnel containing 2 N HCl. The aqueous layer was extracted with EtOAc and the combined organic layers were washed with water, brine and dried over MgSO$_4$. The solution was filtered through diatomaceous earth and the solvent was evaporated. The resulting dark red residue was flash chromatographed (10% EtOAc/hexanes) to give N$^4$-cyclohexylmethyl-2-fluoro-5-nitro-N$^1$-phenyl-benzene-1,4-diamine as a dark red solid (0.48 g, 34.9% yield). M$^+$, 344

A solution of N$^4$-cyclohexylmethyl-2-fluoro-5-nitro-N$^1$-phenyl-benzene-1,4-diamine (0.23 g, 0.66 mmol), N-methylpiperazine (0.22 mL, 1.97 mmol) and N,N'-diisopropylethylamine (0.34, 1.97 mmol) in DMF (3.0 mL) was stirred at 100° C. under an inert atmosphere for 16 h. The reaction mixture was transferred to a separatory funnel containing water. The aqueous layer was extracted with EtOAc and the combined organic layers were washed with water, brine and dried over MgSO$_4$. The solution was filtered through diatomaceous earth and the solvent was evaporated. The resulting dark red residue was flash chromatographed (5% MeOH/CH$_2$Cl$_2$) to give N$^4$-cyclohexylmethyl-2-(4-methyl-piperazin-1-yl)-5-nitro-N$^1$-phenyl-benzene-1,4-diamine as a red foam (0.22 g, 80.7% yield). M$^+$, 424

To a solution of N$^4$-cyclohexylmethyl-2-(4-methyl-piperazin-1-yl)-5-nitro-N$^1$-phenyl-benzene-1,4-diamine (0.22 g, 0.53 mmol) in THF (5.00 mL) was added 10% palladium on activated carbon (0.22 g). The reaction flask was equipped with a septum and was placed under vacuum for 3 min. This flask was placed under hydrogen atmosphere (balloon inflated with hydrogen) and the reaction mixture was stirred for 18 h. The palladium was filtered off through a plug of diatomaceous earth and washed with EtOAc. The solvent was removed via rotary evaporation. The resulting residue was flash chromatographed (5% MeOH/CH$_2$Cl$_2$), yielding N$^1$-cyclohexylmethyl-5-(4-methyl-piperazin-1-yl)-N$^4$-phenyl-benzene-1,2,4-triamine (0.10 g, 49.5% yield). M$^+$, 392

A solution of N$^1$-cyclohexylmethyl-5-(4-methyl-piperazin-1-yl)-N$^4$-phenyl-benzene-1,2,4-triamine (0.10 g, 0.25 mmol) and 1,1'-carbonyldiimidazole (0.12 g, 0.76 mmol) in THF (3 mL) was stirred at room temperature for 17.5 h. The solvent was evaporated and the resulting residue was chromatographed (FCC, 5% MeOH/CH$_2$Cl$_2$) to give the title compound as a white solid (0.07 g, 61.6% yield). M$^+$, 420.

The following compounds were also prepared using the procedure described in the above example:

1-Cyclohexylmethyl-6-(4-methyl-piperazin-1-yl)-5-phenylamino-1,3-dihydro-benzoimidazol-2-one;
1-Cyclohexylmethyl-5-phenylamino-6-piperazin-1-yl-1,3-dihydro-benzoimidazol-2-one;
1-Cyclopentyl-5-(2-fluoro-phenylamino)-6-(4-methyl-piperazin-1-yl)-1,3-dihydro-benzoimidazol-2-one;
1-Cyclohexylmethyl-5-(2-fluoro-phenylamino)-6-piperazin-1-yl-1,3-dihydro-benzoimidazol-2-one;
1-Cyclohexylmethyl-6-(4-methyl-piperazin-1-yl)-5-o-tolylamino-1,3-dihydro-benzoimidazol-2-one;
1-Cyclohexylmethyl-6-[(2-dimethylamino-ethyl)-methylamino]-5-o-tolylamino-1,3-dihydro-benzoimidazol-2-one;
1-Cyclohexylmethyl-6-[(3-dimethylamino-propyl)-methylamino]-5-o-tolylamino-1,3-dihydro-benzoimidazol-2-one.

Example 3

Synthesis of 1-cyclohexylmethyl-5-phenoxy-1,3-dihydro-benzoimidazol-2-one

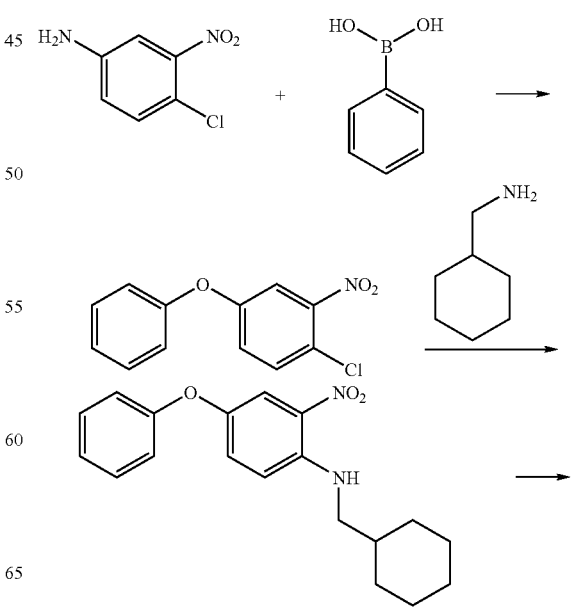

-continued

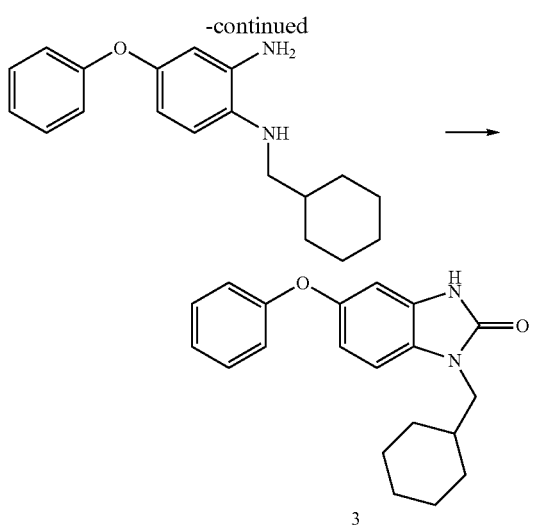

A mixture of 4-chloro-3-nitro-phenol (5.00 g, 28.81 mmol), phenylboronic acid (7.03 g, 57.62 mmol), copper(II) acetate (5.23 g, 28.81 mmol) and 4 Å molecular sieves (0.5 g) in dichloromethane (200 mL) and triethylamine (20.08 mL, 144.04 mmol) was placed in a round bottomed flask. The resulting suspension was stirred under a dry ambient atmosphere at room temperature for 4 days. The mixture was filtered through diatomaceous earth and the solvent was evaporated. The resulting residue was re-dissolved in EtOAc, adhered to silica gel and flash chromatographed (2% EtOAc/hexane) to give 1-chloro-2-nitro-4-phenoxy-benzene as a yellow oil (1.53 g, 22.0% yield).

A solution of 1-chloro-2-nitro-4-phenoxy-benzene (0.60 g, 2.58 mmol), (aminomethyl)cyclohexane (1.0 mL, 7.76 mmol) and N,N'-diisopropylethylamine (1.36, 7.76 mmol) in DMF (20.00 mL) was stirred at 100° C. under an inert atmosphere for 18.5 h. The reaction mixture was transferred to a separatory funnel containing HCl (2.0 N). The aqueous layer was extracted with EtOAc and the combined organic layers were washed with water, brine and dried over $MgSO_4$. The solution was filtered through diatomaceous earth and the solvent was evaporated. The resulting dark red residue was flash chromatographed (10% EtOAc/hexane) to give cyclohexylmethyl-(2-nitro-4-phenoxy-phenyl)-amine as a dark red solid (0.55 g, 65.6% yield).

To a solution of cyclohexylmethyl-(2-nitro-4-phenoxy-phenyl)-amine (0.55 g, 1.69 mmol) in THF (50 mL) was added palladium, 10% on activated carbon (0.55 g). The reaction flask was equipped with a septum and was placed under vacuum for 3 min. This flask was placed under hydrogen atmosphere (balloon inflated with hydrogen) and the reaction mixture was stirred for 18 h. The palladium was filtered off through a plug of diatomaceous earth and washed with EtOAc. The solvent was removed via rotary evaporation providing $N^1$-cyclohexylmethyl-4-phenoxy-benzene-1,2-diamine (0.50 g, 99% yield) which was used in the next step without further purification.

A solution of the above diamine (0.50 g, 1.69 mmol) and 1,1'-carbonyldiimidazole (0.82 g, 5.06 mmol) in THF (30.00 mL) was stirred at room temperature for 17.5 h. The solvent was evaporated and the resulting residue was flash chromatographed (45% EtOAc/hexane) to give the title compound as a colorless solid (0.14 g, 25.6% yield).

The following compound was also prepared using the procedure described in the above example:
1-Benzyl-5-phenoxy-1,3-dihydro-benzoimidazol-2-one.

Assessment of Biological Properties

Inhibition of p38 MAP kinase and inhibition of cytokine production are measured as follows:

Inhibition of P38 MAP Kinase

To determine binding affinities for compounds to p38 MAP kinase, a fluorescence binding assay is used as described [Pargellis, C., Tong, L., Churchill, L., Cirillo, P. F., Gilmore, T., Graham, A. G., Grob, P. M., Hickey, E. R., Moss, N., Pav, S. & Regan, J. Inhibition of p38 MAP kinase by utilizing a novel allosteric binding site. Nature Structural Biology 9, 268–272 (2002)]. Binding studies are conducted in aqueous solutions prepared using binding buffer: 20 mM Bis-TRIS Propane (pH 7.0), 2 mM EDTA, 0.01% $NaN_3$, and 0.15% n-octylglucoside. Kinetic data for the association of SK&F 86002 to p38 MAP kinase is collected on a Kintech fluorescence detector system equipped with a stopped flow controller. The data is fit simultaneously to an appropriate equation describing kinetic binding for a simple 1-step binding mechanism [Morelock, M. M., Pargellis, C. A., Graham, E. T., Lamarre, D. & Jung, G. Time-resolved ligand exchange reactions: kinetic models for competitive inhibitors with recombinant human renin. J. Med. Chem. 38, 1751–1761 (1995)]. The exchange curve assays are run as two half reactions using an SLM Aminco Bowman Series 2 Model SQ-340 fluorescence detector. Preliminary equilibrium are set up with two half reactions differing in the order of addition of the two p38 MAP kinase inhibitors. In the first half reaction, p38 MAP kinase and SK&F 86002 are preincubated for 3 minutes. In the second half reaction p38 MAP kinase is preincubated with BIRB 796 for 60 minutes. A net dissociation of the fluorescent probe, SK&F 86002, is observed for the first half reaction and a net association is observed for the second half reaction. The raw data from both half reactions are fitted simultaneously to an equation describing simple competitive inhibition [Morelock, M. M., Pargellis, C. A., Graham, E. T., Lamarre, D. & Jung, G. Time-resolved ligand exchange reactions: kinetic models for competitive inhibitors with recombinant human renin. J. Med. Chem. 38, 1751–1761 (1995)]. BIRB 796 (chemical name: 1-(5-tert-butyl-2-p-tolyl-2H-pyrazol-3-yl)-3-[4-(2-morpholin-4-yl-ethoxy)-naphthalen-1-yl]-urea) was synthesized as described [Cirillo, P., Gilmore, T. A., Hickey, E., Regan, J. & Zhang, L. H. Aromatic heterocyclic compounds as antiinflammatory agents. (WO0043384) Dec. 9, 1999].

Preferred compounds were evaluated and had $IC_{50}<1$ µM in this assay, confirming inhibition of p38 MAP Kinase.

Inhibition of TNF Production in THP Cells

The inhibition of cytokine production can be observed by measuring inhibition of TNFα: in lipopolysaccharide stimulated THP cells (for example, see W. Prichett et al., 1995, J. Inflammation, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP. 1 cells ($2\times10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 μg/ml final; Siga L-2630, from E. coli serotype 0111. B4; stored as 1 mg/ml stock in endotoxin screened distilled $H_2O$ at −80° C.). Blanks (unstimulated) received $H_2O$ vehicle; final incubation volume was 250 μl. Overnight incubation (18–24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production.

Preferred compounds have an $IC_{50}<10$ μM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al., 1988, Int. J. Immunopharmacol., 10, 835).

What is claimed is:

1. A Compound of the formula (I):

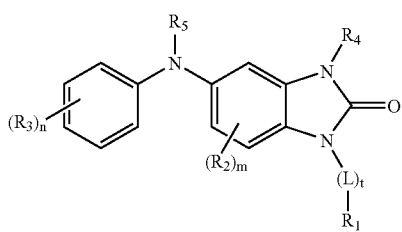

(I)

m and n are independently 0, 1 or 2;
t is 0–10;
L is —$CH_2$— optionally substituted by alkyl or alkoxy;
$R_1$ is chosen from amino, alkyl, $C_{3-7}$ cycloalkyl, aryl, heteroaryl and heterocyclyl each optionally substituted by one to four $R_a$;
$R_2$ is chosen from mono-or-di-alkylamino, alkylthio, alkoxy, $C_{3-7}$ cycloalkyl, aryl, heteroaryl and heterocyclyl each optionally substituted by one to four $R_b$;
each $R_a$ and $R_b$ are independently chosen from alkyl, alkenyl, alkynyl, cycloalkyl, aryl, heteroaryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, oxo, halogen, trifluoromethyl, nitro, nitrile, amino and guanidino each optionally mono-or-di-substituted by alkyl, acyl or alkoxycarbonyl, wherein any of the above $R_a$ or $R_b$ are optionally halogenated where possible;
each $R_3$ is chosen from alkyl, alkenyl, alkynyl, cycloalkyl, aryl, arylalkyl, aryloxy, alkoxy, alkylthio, acyl, alkoxycarbonyl, acyloxy, acylamino, sulphonylamino, amino-sulfonyl, alkylsulfonyl, carboxy, carboxamide, hydroxy, halogen, trifluoromethyl, nitro, nitrile and amino optionally mono-or-di-substituted by alkyl, acyl or alkoxycarbonyl, wherein any of the above $R_3$ are optionally halogenated where possible;
and
$R_4$ is hydrogen;
$R_5$ is chosen from hydrogen and $C_{1-3}$ alkyl;
or the pharmaceutically acceptable acids and salts or isomers thereof.

2. The compound according to claim 1 wherein:
t is 0–5;
L is —$CH_2$— optionally substituted by methyl, ethyl or propyl;
$R_1$ is chosen from amino, $C_{1-6}$ alkyl, $C_{3-7}$ cycloalkyl, indanyl, indenyl, phenyl, naphthyl, heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl and heterocyclyl chosen from aziridinyl, pyrrolidinyl, pyrrolinyl, morpholinyl, thiomorpholinyl, tetrahydrofuranyl, dioxalanyl, piperidinyl and piperazinyl, each optionally substituted by one to three $R_a$;
$R_2$ is chosen from mono-or di-$C_{1-5}$ alkyl amino, $C_{1-5}$ alkylthio, $C_{1-5}$ alkoxy, $C_{3-7}$ cycloalkyl, aryl, heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl and heterocyclyl chosen from aziridinyl, pyrrolidinyl, pyrrolinyl, morpholinyl, thiomorpholinyl, tetrahydrofuranyl, dioxalanyl, piperidinyl and piperazinyl, each optionally substituted by one to three $R_b$;
each $R_a$ and $R_b$ are independently chosen from $C_{1-5}$ alkyl, $C_{2-5}$ alkenyl, $C_{2-5}$ alkynyl, $C_{3-7}$ cycloalkyl, aryl, arylalkyl, aryloxy, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_a$ or $R_b$ are optionally halogenated where possible;
each $R_3$ is chosen from hydrogen, $C_{1-5}$ alkyl, $C_{2-5}$ alkenyl, $C_{2-5}$ alkynyl, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_3$ are optionally halogenated where possible;
and
$R_5$ is chosen from hydrogen and methyl.

3. The compound according to claim 2 wherein:
m is 0 or 1;
n is 0, 1 or 2;
t is 0–3;
L is —$CH_2$— optionally substituted by methyl;
$R_1$ is chosen from $C_{3-6}$ alkyl, amino, $C_{3-7}$ cycloalkyl, indanyl, indenyl, phenyl, naphthyl, heteroaryl chosen from isoxazolyl, oxazolyl, thiadiazolyl, tetrazolyl, pyrazolyl, pyrrolyl, imidazolyl, pyridinyl, pyrimidinyl, pyrazinyl, pyridazinyl, quinoxalinyl, indolyl, benzimidazolyl, benzoxazolyl, benzothiazolyl, quinolinyl, quinazolinyl and indazolyl and heterocyclyl chosen from pyrrolidinyl, pyrrolinyl, morpholinyl, thiomorpholinyl, tetrahydrofuranyl, dioxalanyl, tetrahydropyranyl, piperidinyl and piperazinyl, each optionally substituted by one to two $R_a$;

$R_2$ is chosen from heteroaryl chosen from pyridinyl, pyrimidinyl, pyrazinyl and pyridazinyl and heterocyclyl chosen from morpholinyl, thiomorpholinyl, piperidinyl and piperazinyl, each optionally substituted by one to two $R_b$;

each $R_a$ and $R_b$ are independently chosen from $C_{1-5}$ alkyl, aryloxy, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_a$ or $R_b$ are optionally halogenated where possible;

each $R_3$ is chosen from $C_{1-5}$ alkyl, $C_{1-5}$ alkoxy, $C_{1-5}$ alkylthio, $C_{1-5}$ acyl, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-3}$ alkyl, wherein any of the above $R_3$ are optionally halogenated where possible;

$R_4$ is hydrogen; and and $R_5$ is hydrogen or methyl.

4. The compound according to claim 3 wherein:

t is 0–2;

$R_1$ is chosen from $C_{4-6}$ alkyl, amino, $C_{5-7}$ cycloalkyl, indanyl, indenyl, phenyl, naphthyl, tetrahydronaphthyl, pyridinyl, pyrimidinyl, pyrazinyl, pyridazinyl, pyrrolidinyl, pyrrolinyl, tetrahydrofuranyl, piperidinyl and dioxalanyl, each optionally substituted by one to two $R_a$;

$R_2$ is chosen from heteroaryl chosen from pyridinyl, pyrimidinyl, pyrazinyl and pyridazinyl and heterocyclyl chosen from morpholinyl, thiomorpholinyl, piperidinyl and piperazinyl, each optionally substituted by $R_b$;

each $R_a$ and $R_b$ are independently chosen from $C_{1-5}$ alkyl, aryloxy, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl, wherein any of the above $R_a$ or $R_b$ are optionally halogenated where possible;

each $R_3$ is chosen from $C_{1-5}$ alkyl, $C_{1-5}$ alkoxy, $C_{1-5}$ alkylthio, $C_{1-5}$ acyl, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-3}$ alkyl, wherein any of the above $R_3$ are optionally halogenated where possible.

5. The compound according to claim 4 wherein:

t is 0 or 1;

$R_1$ is chosen from $C_4$ alkyl, amino, $C_{5-6}$ cycloalkyl, indanyl, indenyl, phenyl, naphthyl, tetrahydronaphthyl, pyridinyl, tetrahydrofuranyl and piperidinyl, each optionally substituted by one to two $R_a$;

$R_2$ is chosen from morpholinyl, thiomorpholinyl, pyranyl, piperidinyl and piperazinyl, each optionally substituted by $R_b$;

each $R_a$ and $R_b$ are independently chosen from $C_{1-5}$ alkyl, $C_{1-5}$ alkoxy, $C_{4-6}$ alkoxycarbonyl, hydroxy, halogen, trifluoromethyl, nitro, nitrile and amino wherein any of the above $R_a$ or $R_b$ are optionally halogenated where possible;

each $R_3$ is chosen from $C_{1-3}$ alkyl, $C_{1-3}$ alkoxy, hydroxy, halogen, trifluoromethyl, nitro, nitrile and amino wherein any of the above $R_3$ are optionally halogenated where possible.

6. The compound according to claim 5 wherein:

n is 1 or 2;

m is 0;

$R_1$ is chosen from amino, cyclohexyl, indanyl, indenyl, phenyl, naphthyl, tetrahydronaphthyl, pyridinyl, tetrahydrofuranyl and piperidinyl, each optionally substituted by one to two $R_a$.

7. The compound according to claim 6 wherein: each $R_a$ and $R_b$ are independently chosen from methyl, methoxy, tert-butoxycarbonyl, fluoro, trifluoromethyl and amino; and each $R_3$ is chosen from methyl, methoxy, fluoro, trifluoromethyl and amino.

8. A compound of the formula (II) wherein:

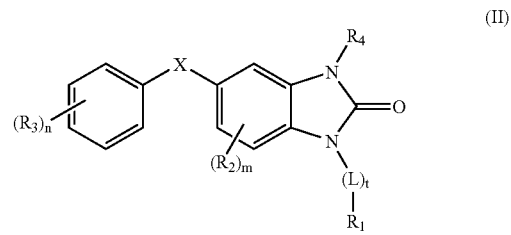

(II)

X is O;

m is 0, 1 or 2;

n is 0, 1 or 2;

t is 0 or 1;

L is —CH$_2$— optionally substituted by methyl;

$R_1$ is chosen from t-butyl, amino, cyclohexyl and phenyl, the phenyl is optionally substituted by one to two $R_a$;

$R_2$ is chosen from mono- or di-$C_{1-5}$ alkyl amino, $C_{1-5}$ alkylthio, $C_{1-5}$ alkoxy, $C_{3-7}$ cycloalkyl, aryl, heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl and heterocyclyl chosen from aziridinyl, pyrrolidinyl, pyrrolinyl, morpholinyl, thiomorpholinyl, tetrahydrofuranyl, dioxalanyl, piperidinyl and piperazinyl, each optionally substituted by one to three $R_b$;

$R_a$ is chosen from methoxy, tert-butoxycarbonyl, fluoro, trifluoromethyl and amino;

$R_b$ is chosen from $C_{1-5}$ alkyl, aryloxy, $C_{1-5}$ alkoxy, $C_{1-5}$ alkylthio, $C_{1-5}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{2-7}$ alkoxycarbonyl;

each R₃ is chosen from methyl, methoxy, fluoro, trifluoromethyl, and amino;
and
R₄ is hydrogen;
or the pharmaceutically acceptable acids and salts or isomers thereof.

9. The compound according to claim 8 wherein:
each R_a is chosen from methoxy, tert-butoxycarbonyl, fluoro, trifluoromethyl and amino;
and
each R₃ is chosen from methyl and fluoro.

10. The compound according to claim 9 wherein:
R₁ is cyclohexyl.

11. The compound according to claim 10 wherein:
R₂ is mono- or di C1–5 alkyl amino further substituted by mono- or di C1–5 alkyl amino.

12. The compound according to claim 10 wherein:
R₂ is chosen from $C_{1-3}$ alkylthio or $C_{1-3}$ alkoxy each further substituted by mono-or di $C_{1-5}$ alkyl amino.

13. A pharmaceutical composition comprising a pharmaceutically effective amount of a compound according to claims 1 or 8 and one or more pharmaceutically acceptable carriers and/or adjuvants.

14. A compound chosen from:
1-Cyclohexylmethyl-5-phenylamino-1,3-dihydro-benzoimidazol-2-one;
1-Cyclohexylmethyl-5-(3,5-dichloro-phenylamino)-1,3-dihydro-benzoimidazol-2-one;
5-(3-Amino-4-methyl-phenylamino)-1-cyclohexylmethyl-1,3-dihydro-benzoimidazol-2-one;
1-Cyclohexylmethyl-5-(2-fluoro-phenylamino)-1,3-dihydro-benzoimidazol-2-one;
1-Cyclohexylmethyl-5-(2-methoxy-phenylamino)-1,3-dihydro-benzoimidazol-2-one;
1-Cyclohexylmethyl-5-(3-trifluoromethyl-phenylamino)-1,3-dihydro-benzoimidazol-2-one;
1-Cyclohexylmethyl-5-(4-fluoro-phenylamino)-1,3-dihydro-benzoimidazol-2-one;
1-Cyclohexylmethyl-5-o-tolylamino-1,3-dihydro-benzoimidazol-2-one;
1-Cyclohexylmethyl-5-(2,4-difluoro-phenylamino)-1,3-dihydro-benzoimidazol-2-one;
1-Cyclohexylmethyl-5-(3-fluoro-phenylamino)-1,3-dihydro-benzoimidazol-2-one;
1-Cyclohexylmethyl-5-(3,4-difluoro-phenylamino)-1,3-dihydro-benzoimidazol-2-one;
1-Phenyl-5-phenylamino-1,3-dihydro-benzoimidazol-2-one;
1-Cyclohexylmethyl-6-(4-methyl-piperazin-1-yl)-5-phenylamino-1,3-dihydro-benzoimidazol-2-one;
1-Cyclohexylmethyl-5-phenylamino-6-piperazin-1-yl-1,3-dihydro-benzoimidazol-2-one;
1-Cyclopentyl-5-(2-fluoro-phenylamino)-6-(4-methyl-piperazin-1-yl)-1,3-dihydro-benzoimidazol-2-one;
1-Cyclohexylmethyl-5-(2-fluoro-phenylamino)-6-piperazin-1-yl-1,3-dihydro-benzoimidazol-2-one;
1-Cyclohexylmethyl-6-(4-methyl-piperazin-1-yl)-5-o-tolylamino-1,3-dihydro-benzoimidazol-2-one;
1-Cyclohexylmethyl-6-[(2-dimethylamino-ethyl)-methyl-amino]-5-o-tolylamino-1,3-dihydro-benzoimidazol-2-one;
1-Cyclohexylmethyl-6-[(3-dimethylamino-propyl)-methyl-amino]-5-o-tolylamino-1,3-dihydro-benzoimidazol-2-one;
5-anilino-1-benzyl-1,3-dihydro-2H-benzimidazol-2-one;
5-anilino-1-(1-phenylethyl)-1,3-dihydro-2H-benzimidazol-2-one;
5-anilino-1-(1,2,3,4-tetrahydronaphthalen-1-yl)-1,3-dihydro-2H-benzimidazol-2-one;
5-anilino-1-(2,3-dihydro-1H-inden-1-yl)-1,3-dihydro-2H-benzimidazol-2-one;
5-anilino-1-(pyridin-3-ylmethyl)-1,3-dihydro-2H-benzimidazol-2-one;
5-anilino-1-(4-chlorobenzyl)-1,3-dihydro-2H-benzimidazol-2-one;
5-anilino-1-(2,6-difluorobenzyl)-1,3-dihydro-2H-benzimidazol-2-one
5-anilino-1-(2,4-dichlorobenzyl)-1,3-dihydro-2H-benzimidazol-2-one;
5-anilino-1-(2,3-dichlorobenzyl)-1,3-dihydro-2H-benzimidazol-2-one;
5-anilino-1-(3-methoxybenzyl)-1,3-dihydro-2H-benzimidazol-2-one;
5-anilino-1-(2,6-dimethoxybenzyl)-1,3-dihydro-2H-benzimidazol-2-one;
5-anilino-1-(3,5-dimethoxybenzyl)-1,3-dihydro-2H-benzimidazol-2-one;
5-anilino-1-(2,4-dimethoxybenzyl)-1,3-dihydro-2H-benzimidazol-2-one;
5-anilino-1-(2,3-dimethoxybenzyl)-1,3-dihydro-2H-benzimidazol-2-one;
5-anilino-1-(2,5-dimethoxybenzyl)-1,3-dihydro-2H-benzimidazol-2-one;
5-anilino-1-(2-methylbenzyl)-1,3-dihydro-2H-benzimidazol-2-one;
5-anilino-1-(3,5-dimethylbenzyl)-1,3-dihydro-2H-benzimidazol-2-one;
5-anilino-1-(3,4-dimethylbenzyl)-1,3-dihydro-2H-benzimidazol-2-one;
5-anilino-1-(2,3-dimethylbenzyl)-1,3-dihydro-2H-benzimidazol-2-one;
5-anilino-1-[2-(trifluoromethyl)benzyl]-1,3-dihydro-2H-benzimidazol-2-one;
5-anilino-1-[3-(trifluoromethyl)benzyl]-1,3-dihydro-2H-benzimidazol-2-one;
5-anilino-1-(2-phenylethyl)-1,3-dihydro-2H-benzimidazol-2-one;
5-anilino-1-(2-pyridin-2-ylethyl)-1,3-dihydro-2H-benzimidazol-2-one;
5-anilino-1-(2-pyridin-3-ylethyl)-1,3-dihydro-2H-benzimidazol-2-one;
5-anilino-1-(2-pyridin-4-ylethyl)-1,3-dihydro-2H-benzimidazol-2-one;
5-anilino-1-(2-thien-2-ylethyl)-1,3-dihydro-2H-benzimidazol-2-one;
5-anilino-1-[3-(1H-imidazol-1-yl)propyl]-1,3-dihydro-2H-benzimidazol-2-one;
5-anilino-1-[3-(2-oxopyrrolidin-1-yl)propyl]-1,3-dihydro-2H-benzimidazol-2-one;
5-anilino-1-(2-methoxyethyl)-1,3-dihydro-2H-benzimidazol-2-one;
5-anilino-1-(tetrahydrofuran-2-ylmethyl)-1,3-dihydro-2H-benzimidazol-2-one;
ethyl 3-(5-anilino-2-oxo-2,3-dihydro-1H-benzimidazol-1-yl)butanoate;
5-anilino-1-tert-butyl-1,3-dihydro-2H-benzimidazol-2-one;
5-anilino-1-(1,2-dimethylpropyl)-1,3-dihydro-2H-benzimidazol-2-one;
5-anilino-1-butyl-1,3-dihydro-2H-benzimidazol-2-one;
5-anilino-1-pentyl-1,3-dihydro-2H-benzimidazol-2-one;
5-anilino-1-hexyl-1,3-dihydro-2H-benzimidazol-2-one;
5-anilino-1-(cyclopropylmethyl)-1,3-dihydro-2H-benzimidazol-2-one;

5-anilino-1-(1-cyclohexylethyl)-1,3-dihydro-2H-benzimidazol-2-one;
5-anilino-1-cyclopentyl-1,3-dihydro-2H-benzimidazol-2-one;
5-anilino-1-(4-methylcyclohexyl)-1,3-dihydro-2H-benzimidazol-2-one;
5-anilino-1-[2-(dimethylamino)ethyl]-1,3-dihydro-2H-benzimidazol-2-one;
5-anilino-1-(2-morpholin-4-ylethyl)-1,3-dihydro-2H-benzimidazol-2-one;
5-anilino-1-(2-pyrrolidin-1-ylethyl)-1,3-dihydro-2H-benzimidazol-2-one;
5-anilino-1-(2-piperidin-1-ylethyl)-1,3-dihydro-2H-benzimidazol-2-one;
tert-butyl 2-(5-anilino-2-oxo-2,3-dihydro-1H-benzimidazol-1-yl)ethylcarbamate;
5-anilino-1-(3-methoxypropyl)-1,3-dihydro-2H-benzimidazol-2-one;
5-anilino-1-[3-(dimethylamino)propyl]-1,3-dihydro-2H-benzimidazol-2-one;
5-anilino-1-[3-(4-methylpiperazin-1-yl)propyl]-1,3-dihydro-2H-benzimidazol-2-one;
5-anilino-1-(3-morpholin-4-ylpropyl)-1,3-dihydro-2H-benzimidazol-2-one;
5-anilino-1-[(1-ethylpyrrolidin-2-yl)methyl]-1,3-dihydro-2H-benzimidazol-2-one;
5-anilino-1-[2-(1-methylpyrrolidin-2-yl)ethyl]-1,3-dihydro-2H-benzimidazol-2-one; and
ethyl 4-(5-anilino-2-oxo-2,3-dihydro-1H-benzimidazol-1-yl)piperidine-1-carboxylate
or the pharmaceutically acceptable acids and salts or isomers thereof.

15. A compound chosen from:
1-Cyclohexylmethyl-5-p-tolylamino-1,3-dihydro-benzoimidazol-2-one;
5-anilino-1-(1-methyl-1-phenylethyl)-1,3-dihydro-2H-benzimidazol-2-one;
5-anilino-1-(1-naphthylmethyl)-1,3-dihydro-2H-benzimidazol-2-one;
5-anilino-1-(pyridin-2-ylmethyl)-1,3-dihydro-2H-benzimidazol-2-one;
5-anilino-1-(pyridin-4-ylmethyl)-1,3-dihydro-2H-benzimidazol-2-one;
5-anilino-1-(2-bromobenzyl)-1,3-dihydro-2H-benzimidazol-2-one;
5-anilino-1-(3-chlorobenzyl)-1,3-dihydro-2H-benzimidazol-2-one;
5-anilino-1-(3,5-dichlorobenzyl)-1,3-dihydro-2H-benzimidazol-2-one;
5-anilino-1-(3,4-dichlorobenzyl)-1,3-dihydro-2H-benzimidazol-2-one;
5-anilino-1-(2,5-dichlorobenzyl)-1,3-dihydro-2H-benzimidazol-2-one;
5-anilino-1-(2-methoxybenzyl)-1,3-dihydro-2H-benzimidazol-2-one;
5-anilino-1-(4-methoxybenzyl)-1,3-dihydro-2H-benzimidazol-2-one;
5-anilino-1-(3,4-dimethoxybenzyl)-1,3-dihydro-2H-benzimidazol-2-one;
5-anilino-1-(3-methylbenzyl)-1,3-dihydro-2H-benzimidazol-2-one;
5-anilino-1-(4-methylbenzyl)-1,3-dihydro-2H-benzimidazol-2-one;
5-anilino-1-(2,4-dimethylbenzyl)-1,3-dihydro-2H-benzimidazol-2-one;
5-anilino-1-(2,5-dimethylbenzyl)-1,3-dihydro-2H-benzimidazol-2-one;
5-anilino-1-[4-(trifluoromethyl)benzyl]-1,3-dihydro-2H-benzimidazol-2-one;
5-anilino-1-(thien-2-ylmethyl)-1,3-dihydro-2H-benzimidazol-2-one;
5-anilino-1-(2-furylmethyl)-1,3-dihydro-2H-benzimidazol-2-one;
5-anilino-1-[4-(methylsulfonyl)benzyl]-1,3-dihydro-2H-benzimidazol-2-one;
4-[(5-anilino-2-oxo-2,3-dihydro-1H-benzimidazol-1-yl)methyl]benzenesulfonamide;
5-anilino-1-[4-(dimethylamino)benzyl]-1,3-dihydro-2H-benzimidazol-2-one;
5-anilino-1-(1,1'-biphenyl-3-ylmethyl)-1,3-dihydro-2H-benzimidazol-2-one;
methyl 4-[(5-anilino-2-oxo-2,3-dihydro-1H-benzimidazol-1-yl)methyl]benzoate;
5-anilino-1-(1H-imidazol-4-ylmethyl)-1,3-dihydro-2H-benzimidazol-2-one;
5-anilino-1-tetrahydrofuran-3-yl-1,3-dihydro-2H-benzimidazol-2-one;
5-anilino-1-(2-oxotetrahydrofuran-3-yl)-1,3-dihydro-2H-benzimidazol-2-one;
methyl 2-(5-anilino-2-oxo-2,3-dihydro-1H-benzimidazol-1-yl)propanoate;
5-anilino-1-isobutyl-1,3-dihydro-2H-benzimidazol-2-one;
5-anilino-1-(3-methylbutyl)-1,3-dihydro-2H-benzimidazol-2-one;
methyl (5-anilino-2-oxo-2,3-dihydro-1H-benzimidazol-1-yl)acetate;
2-(5-anilino-2-oxo-2,3-dihydro-1H-benzimidazol-1-yl)acetamide;
5-anilino-1-(2-oxoazepan-3-yl)-1,3-dihydro-2H-benzimidazol-2-one;
(5-anilino-2-oxo-2,3-dihydro-1H-benzimidazol-1-yl)acetonitrile;
3-(5-anilino-2-oxo-2,3-dihydro-1H-benzimidazol-1-yl)propanenitrile;
5-anilino-1-(2-oxo-2-phenylethyl)-1,3-dihydro-2H-benzimidazol-2-one;
5-anilino-1-[2-(1H-imidazol-4-yl)ethyl]-1,3-dihydro-2H-benzimidazol-2-one;
5-anilino-1-[3-(1H-imidazol-4-yl)propyl]-1,3-dihydro-2H-benzimidazol-2-one;
1-Cyclohexylmethyl-6-[4-(2-oxo-2,3-dihydro-benzoimidazol-1-yl)-piperidin-1-yl]-5-phenylamino-1,3-dihydro-benzoimidazol-2-one;
8-[6-anilino-3-(cyclohexylmethyl)-2-oxo-2,3-dihydro-1H-benzimidazol-5-yl]-1-phenyl-1,3,8-triazaspiro[4.5]decan-4-one;
3-[[6-anilino-3-(cyclohexylmethyl)-2-oxo-2,3-dihydro-1H-benzimidazol-5-yl](methyl)amino]propanenitrile;
5-anilino-1-(cyclohexylmethyl)-6-[4-(piperidin-1-ylmethyl)piperidin-1-yl]-1,3-dihydro-2H-benzimidazol-2-one;
5-anilino-1-(cyclohexylmethyl)-6-[cylohexyl(methyl)amino]-1,3-dihydro-2H-benzimidazol-2-one;
5-anilino-1-(cyclohexylmethyl)-6-(4-cyclohexylpiperazin-1-yl)-1,3-dihydro-2H-benzimidazol-2-one;
5-anilino-1-(cyclohexylmethyl)-6-(1,3-thiazolidin-3-yl)-1,3-dihydro-2H-benzimidazol-2-one;
2-{4-[6-anilino-3-(cyclohexylmethyl)-2-oxo-2,3-dihydro-1H-benzimidazol-5-yl]piperazin-1-yl}-N-isopropylacetamide;
5-anilino-1-(cyclohexylmethyl)-6-pyrrolidin-1-yl-1,3-dihydro-2H-benzimidazol-2-one;

5-anilino-1-(cyclohexylmethyl)-6-(4-phenylpiperazin-1-yl)-1,3-dihydro-2H-benzimidazol-2-one;

5-anilino-1-(cyclohexylmethyl)-6-[4-(2-methoxyphenyl)piperazin-1-yl]-1,3-dihydro-2H-benzimidazol-2-one;

5-anilino-1-(cyclohexylmethyl)-6-(1,4-dioxa-8-azaspiro[4.5]dec-8-yl)-1,3-dihydro-2H-benzimidazol-2-one;

ethyl 4-[6-anilino-3-(cyclohexylmethyl)-2-oxo-2,3-dihydro-1H-benzimidazol-5-yl]piperazine-1-carboxylate;

5-anilino-1-(cyclohexylmethyl)-6-(4-methylpiperazin-1-yl)-1,3-dihydro-2H-benzimidazol-2-one;

5-anilino-1-(cyclohexylmethyl)-6-(4-pyridin-4-ylpiperazin-1-yl)-1,3-dihydro-2H-benzimidazol-2-one;

5-anilino-1-(cyclohexylmethyl)-6-thiomorpholin-4-yl-1,3-dihydro-2H-benzimidazol-2-one;

5-anilino-1-(cyclohexylmethyl)-6-{4-[2-(dimethylamino)ethyl]piperazin-1-yl}-1,3-dihydro-2H-benzimidazol-2-one;

5-anilino-1-(cyclohexylmethyl)-6-piperidin-1-yl-1,3-dihydro-2H-benzimidazol-2-one;

5-anilino-1-(cyclohexylmethyl)-6-{4-[3-(dimethylamino)propyl]piperazin-1-yl}-1,3-dihydro-2H-benzimidazol-2-one;

6-{4-[2-(aminooxy)ethyl]piperazin-1-yl}-5-anilino-1-(cyclohexylmethyl)-1,3-dihydro-2H-benzimidazol-2-one;

5-anilino-1-(cyclohexylmethyl)-6-(2,6-dimethylpiperidin-1-yl)-1,3-dihydro-2H-benzimidazol-2-one;

1-[6-anilino-3-(cyclohexylmethyl)-2-oxo-2,3-dihydro-1H-benzimidazol-5-yl]N,N-diethylpiperidine-3-carboxamide;

ethyl 1-[6-anilino-3-(cyclohexylmethyl)-2-oxo-2,3-dihydro-1H-benzimidazol-5-yl]piperidine-3-carboxylate;

1-[6-anilino-3-(cyclohexylmethyl)-2-oxo-2,3-dihydro-1H-benzimidazol-5-yl]piperidine-3-carboxamide;

5-anilino-1-(cyclohexylmethyl)-6-(3-methylpiperidin-1-yl)-1,3-dihydro-2H-benzimidazol-2-one;

ethyl 1-[6-anilino-3-(cyclohexylmethyl)-2-oxo-2,3-dihydro-1H-benzimidazol-5-yl]piperidine-4-carboxylate;

5-anilino-1-(cyclohexylmethyl)-6-(4-methylpiperidin-1-yl)-1,3-dihydro-2H-benzimidazol-2-one;

5-anilino-1-(cyclohexylmethyl)-6-(4-pyridin-2-ylpiperazin-1-yl)-1,3-dihydro-2H-benzimidazol-2-one;

5-anilino-1-(cyclohexylmethyl)-6-[methyl(2-pyridin-2-ylethyl)amino]-1,3-dihydro-2H-benzimidazol-2-one;

5-anilino-6-(1,4'-bipiperidin-1'-yl)-1-(cyclohexylmethyl)-1,3-dihydro-2H-benzimidazol-2-one;

5-anilino-1-(cyclohexylmethyl)-6-[methyl(1-methylpiperidin-4-yl)amino]-1,3-dihydro-2H-benzimidazol-2-one;

5-anilino-1-(cyclohexylmethyl)-6-(dimethylamino)-1,3-dihydro-2H-benzimidazol-2-one;

6-[allyl(methyl)amino]-5-anilino-1-(cyclohexylmethyl)-1,3-dihydro-2H-benzimidazol-2-one;

5-anilino-1-(cyclohexylmethyl)-6-(2,2-dimethyl-1,3-thiazolidin-3-yl)-1,3-dihydro-2H-benzimidazol-2-one;

5-anilino-1-(cyclohexylmethyl)-6-[[2-(dimethylamino)ethyl](methyl)amino]-1,3-dihydro-2H-benzimidazol-2-one;

5-anilino-1-(cyclohexylmethyl)-6-[methyl(2-pyridin-4-ylethyl)amino]-1,3-dihydro-2H-benzimidazol-2-one;

6-(4-acetylpiperazin-1-yl)-5-anilino-1-(cyclohexylmethyl)-1,3-dihydro-2H-benzimidazol-2-one;

N-{1-[6-anilino-3-(cyclohexylmethyl)-2-oxo-2,3-dihydro-1H-benzimidazol-5-yl]pyrrolidin-3-yl}-N-methylacetamide;

5-anilino-1-(cyclohexylmethyl)-6-[methyl(1-methylpyrrolidin-3-yl)amino]-1,3-dihydro-2H-benzimidazol-2-one;

5-anilino-1-(cyclohexylmethyl)-6-(4-methyl-1,4-diazepan-1-yl)-1,3-dihydro-2H-benzimidazol-2-one;

5-anilino-1-(cyclohexylmethyl)-6-(4-ethylpiperazin-1-yl)-1,3-dihydro-2H-benzimidazol-2-one;

5-anilino-1-(cyclohexylmethyl)-6-[(2R)-2-(methoxymethyl)pyrrolidin-1-yl]-1,3-dihydro-2H-benzimidazol-2-one;

tert-butyl 4-[6-anilino-3-(cyclohexylmethyl)-2-oxo-2,3-dihydro-1H-benzimidazol-5-yl]piperazine-1-carboxylate;

6-[allyl(cyclopentyl)amino]-5-anilino-1-(cyclohexylmethyl)-1,3-dihydro-2H-benzimidazol-2-one;

methyl 1-[6-anilino-3-(cyclohexylmethyl)-2-oxo-2,3-dihydro-1H-benzimidazol-5-yl]piperidine-4-carboxylate;

5-anilino-1-(cyclohexylmethyl)-6-[(3R)-3-(dimethylamino)pyrrolidin-1-yl]-1,3-dihydro-2H-benzimidazol-2-one;

5-anilino-1-(cyclohexylmethyl)-6-[(3S)-3-(dimethylamino)pyrrolidin-1-yl]-1,3-dihydro-2H-benzimidazol-2-one;

1-[6-anilino-3-(cyclohexylmethyl)-2-oxo-2,3-dihydro-1H-benzimidazol-5-yl]-D-prolinamide;

5-anilino-1-(cyclohexylmethyl)-6-[4-(3,5-dichloropyridin-4-yl)piperazin-1-yl]-1,3-dihydro-2H-benzimidazol-2-one;

1-[6-anilino-3-(cyclohexylmethyl)-2-oxo-2,3-dihydro-1H-benzimidazol-5-yl]-1H-pyrrole-2-carbonitrile;

6-(4-acetyl-1,4-diazepan-1-yl)-5-anilino-1-(cyclohexylmethyl)-1,3-dihydro-2H-benzimidazol-2-one;

3-{4-[6-anilino-3-(cyclohexylmethyl)-2-oxo-2,3-dihydro-1H-benzimidazol-5-yl]piperazin-1-yl}pyrazine-2-carbonitrile;

5-anilino-1-(cyclohexylmethyl)-6-(diethylamino)-1,3-dihydro-2H-benzimidazol-2-one;

5-anilino-1-(cyclohexylmethyl)-6-[4-(3-methoxyphenyl)piperazin-1-yl]-1,3-dihydro-2H-benzimidazol-2-one;

5-anilino-1-(cyclohexylmethyl)-6-[4-(4-methoxyphenyl)piperazin-1-yl]-1,3-dihydro-2H-benzimidazol-2-one;

ethyl {4-[6-anilino-3-(cyclohexylmethyl)-2-oxo-2,3-dihydro-1H-benzimidazol-5-yl]piperazin-1-yl}acetate;

5-anilino-6-(4-benzylpiperazin-1-yl)-1-(cyclohexylmethyl)-1,3-dihydro-2H-benzimidazol-2-one;

5-anilino-1-(cyclohexylmethyl)-6-(2-methylpiperidin-1-yl)-1,3-dihydro-2H-benzimidazol-2-one;

5-anilino-1-(cyclohexylmethyl)-6-(2-{[(2S)-1-methylpyrrolidin-2-yl]methyl}piperidin-1-yl)-1,3-dihydro-2H-benzimidazol-2-one;

5-anilino-1-(cyclohexylmethyl)-6-morpholin-4-yl-1,3-dihydro-2H-benzimidazol-2-one;

5-anilino-1-(cyclohexylmethyl)-6-[4-(tetrahydrofuran-2-ylcarbonyl)piperazin-1-yl]-1,3-dihydro-2H-benzimidazol-2-one;

5-anilino-1-(cyclohexylmethyl)-6-(4-hydroxy-4-phenylpiperidin-1-yl)-1,3-dihydro-2H-benzimidazol-2-one;

5-anilino-1-(cyclohexylmethyl)-6-[(cyclopropylmethyl)(propyl)amino]-1,3-dihydro-2H-benzimidazol-2-one;

5-anilino-1-(cyclohexylmethyl)-6-[(2-hydroxyethyl)(pentyl)amino]-1,3-dihydro-2H-benzimidazol-2-one;

5-anilino-6-[butyl(propyl)amino]-1-(cyclohexylmethyl)-1,3-dihydro-2H-benzimidazol-2-one;

5-anilino-6-[bis(2-methoxyethyl)amino]-1-(cyclohexylmethyl)-1,3-dihydro-2H-benzimidazol-2-one;

5-anilino-1-(cyclohexylmethyl)-6-(4-pyrimidin-2-ylpiperazin-1-yl)-1,3-dihydro-2H-benzimidazol-2-one;
tert-butyl 1-[6-anilino-3-(cyclohexylmethyl)-2-oxo-2,3-dihydro-1H-benzimidazol-5-yl]pyrrolidin-3-ylcarbamate;
5-anilino-1-(cyclohexylmethyl)-6-(3,5-dimethylpiperidin-1-yl)-1,3-dihydro-2H-benzimidazol-2-one;
ethyl N-[6-anilino-3-(cyclohexylmethyl)-2-oxo-2,3-dihydro-1H-benzimidazol-5-yl]-N-(2-furylmethyl)-beta-alaninate;
tert-butyl 4-[6-anilino-3-(cyclohexylmethyl)-2-oxo-2,3-dihydro-1H-benzimidazol-5-yl]-1,4-diazepane-1-carboxylate;
5-anilino-1-(cyclohexylmethyl)-6-[methyl(2-phenylethyl)amino]-1,3-dihydro-2H-benzimidazol-2-one;
5-anilino-1-(cyclohexylmethyl)-6-[(2-methoxyethyl)(propyl)amino]-1,3-dihydro-2H-benzimidazol-2-one;
5-anilino-1-(cyclohexylmethyl)-6-[4-(4-nitrophenyl)piperazin-1-yl]-1,3-dihydro-2H-benzimidazo
5-anilino-6-(4-benzyl-1,4-diazepan-1-yl)-1-(cyclohexylmethyl)-1,3-dihydro-2H-benzimidazol-2one;
5-anilino-1-(cyclohexylmethyl)-6-[4-(4-hydroxyphenyl)piperazin-1-yl]-1,3-dihydro-2H-benzimidazol-2-one;
5-anilino-1-(cyclohexylmethyl)-6-[4-(2-hydroxyphenyl)piperazin-1-yl]-1,3-dihydro-2H-benzimidazol-2-one;
6-[allyl(cyclohexyl)amino]-5-anilino-1-(cyclohexylmethyl)-1,3-dihydro-2H-benzimidazol-2-one;
3-[[6-anilino-3-(cyclohexylmethyl)-2-oxo-2,3-dihydro-1H-benzimidazol-5-yl](butyl)amino]propanenitrile;
5-anilino-1-(cyclohexylmethyl)-6-[[2-(dimethylamino)ethyl](ethyl)amino]-1,3-dihydro-2H-benzimidazol-2-one;
1-Cyclohexylmethyl-6-((R)-2-methoxymethyl-pyrrolidin-1-yl)-5-phenylamino-1,3-dihydro-benzoimidazol-2-one;
tert-butyl 1-[6-anilino-3-(cyclohexylmethyl)-2-oxo-2,3-dihydro-1H-benzimidazol-5-yl]pyrrolidin-3-yl(methyl)carbamate;
6-[4-(4-acetylphenyl)piperazin-1-yl]-5-anilino-1-(cyclohexylmethyl)-1,3-dihydro-2H-benzimidazol-2-one;
6-(4-Benzyl-piperazin-1-yl)-1-cyclohexylmethyl-5-phenylamino-1,3-dihydro-benzoimidazol-2-one;
ethyl 1-[6-anilino-3-(cyclohexylmethyl)-2-oxo-2,3-dihydro-1H-benzimidazol-5-yl]-1H-pyrrole-2-carboxylate;
1-[4-(2-Dimethylamino-ethoxy)-benzyl]-5-phenylamino-1,3-dihydro-benzoimidazol-2-one;
5-(2,4-Difluoro-phenylamino)-1-[4-(2-dimethylamino-ethoxy)-benzyl]-1,3-dihydro-benzoimidazol-2-one;
1-(2,6-Difluoro-phenyl)-5-phenylamino-1,3-dihydro-benzoimidazol-2-one;
1-Phenyl-5-phenylamino-1,3-dihydro-benzoimidazol-2-one;
5-(2,4-Difluoro-phenylamino)-1-phenyl-1,3-dihydro-benzoimidazol-2-one;
1-(2,6-Dichloro-phenyl)-5-phenylamino-1,3-dihydro-benzoimidazol-2-one;
1-Cyclohexylmethyl-6-(2-dimethylamino-ethylsulfanyl)-5-phenylamino-1,3-dihydro-benzoimidazol-2-one;
1-Cyclohexylmethyl-5-(2,4-difluoro-phenylamino)-6-(2-dimethylamino-ethylsulfanyl)-1,3-dihydro-benzoimidazol-2-one;
1-Cyclohexylmethyl-6-(2-dimethylamino-ethoxy)-5-phenylamino-1,3-dihydro-benzoimidazol-2-one;
1-Cyclohexylmethyl-5-(2,4-difluoro-phenylamino)-6-(2-dimethylamino-ethoxy)-1,3-dihydro-benzoimidazol-2-one;
1-Cyclohexylmethyl-6-(2-dimethylamino-ethylamino)-5-phenylamino-1,3-dihydro-benzoimidazol-2-one
and
1-Cyclohexylmethyl-5-(2,4-difluoro-phenylamino)-6-(2-dimethylamino-ethylamino)-1,3-dihydro-benzoimidazol-2one
or the pharmaceutically acceptable acids and salts or isomers thereof.

16. A compound chosen from:
1-benzyl-5-phenoxy-1,3-dihydro-benzoimidazol-2-one;
1-Cyclohexylmethyl-5-phenoxy-1,3-dihydro-benzoimidazol-2-one;
1-Benzyl-5-o-tolyloxy-1,3-dihydro-benzoimidazol-2-one;
1-tert-Butyl-5-phenoxy-1,3-dihydro-benzoimidazol-2-one;
1-Cyclopentyl-5-phenoxy-1,3-dihydro-benzoimidazol-2-one;
5-Phenoxy-1-piperidin-4-yl-1,3-dihydro-benzoimidazol-2-one;
5-Phenoxy-1-piperidin-4-ylmethyl-1,3-dihydro-benzoimidazol-2-one;
1-(2-Amino-ethyl)-5-phenoxy-1,3-dihydro-benzoimidazol-2-one;
1-(2-Amino-1,1-dimethyl-ethyl)-5-phenoxy-1,3-dihydro-benzoimidazol-2-one;
1-(2-Amino-2-methyl-propyl)-5-phenoxy-1,3-dihydro-benzoimidazol-2-one;
1-Cyclohexylmethyl-5-phenylsulfanyl-1,3-dihydro-benzoimidazol-2-one;
1-tert-Butyl-5-phenylsulfanyl-1,3-dihydro-benzoimidazol-2-one;
1-Cyclopentyl-5-phenylsulfanyl-1,3-dihydro-benzoimidazol-2-one;
5-Phenylsulfanyl-1-piperidin-4-yl-1,3-dihydro-benzoimidazol-2-one;
5-Phenylsulfanyl-1-piperidin-4-ylmethyl-1,3-dihydro-benzoimidazol-2-one;
1-(2-Amino-ethyl)-5-phenylsulfanyl-1,3-dihydro-benzoimidazol-2-one;
1-(2-Amino-1,1-dimethyl-ethyl)-5-phenylsulfanyl-1,3-dihydro-benzoimidazol-2-one
and
1-(2-Amino-2-methyl-propyl)-5-phenylsulfanyl-1,3-dihydro-benzoimidazol-2-one
or the pharmaceutically acceptable acids and salts or isomers thereof.

* * * * *